US008101187B2

(12) United States Patent
Le Page et al.

(10) Patent No.: US 8,101,187 B2
(45) Date of Patent: Jan. 24, 2012

(54) SECRETED *STREPTOCOCCUS PNEUMONIAE* PROTEINS

(75) Inventors: Richard William Falla Le Page, Bangkok (TH); Daniel Badcock, London (GB); Philip James Holden Sizer, Helsby (GB); Keith Peek, Chester (GB); Jeremy Mark Wells, Norwich (GB); Sean Bosco Hanniffy, Norwich (GB)

(73) Assignee: Sanofi Pasteur Limited, Toronto (CA)

( * ) Notice: Subject to any disclaimer, the term of this patent is extended or adjusted under 35 U.S.C. 154(b) by 93 days.

(21) Appl. No.: 12/180,896

(22) Filed: Jul. 28, 2008

(65) Prior Publication Data

US 2009/0074808 A1 Mar. 19, 2009

Related U.S. Application Data

(63) Continuation of application No. 10/476,460, filed as application No. PCT/GB02/01480 on Mar. 28, 2002, now abandoned.

(30) Foreign Application Priority Data

Mar. 30, 2001 (GB) .................................. 0108079.5

(51) Int. Cl.
*A61K 39/00* (2006.01)
*A61K 39/38* (2006.01)
*A61K 39/02* (2006.01)
*A61K 39/09* (2006.01)
*A61K 39/085* (2006.01)
*A61K 38/00* (2006.01)
*C07K 1/00* (2006.01)
*C07K 14/00* (2006.01)
*C07K 17/00* (2006.01)
*C07K 16/00* (2006.01)

(52) U.S. Cl. ............... 424/190.1; 424/184.1; 424/185.1; 424/234.1; 424/237.1; 424/244.1; 530/300; 530/350

(58) Field of Classification Search ........................ None
See application file for complete search history.

(56) References Cited

U.S. PATENT DOCUMENTS

| | | | |
|---|---|---|---|
| 5,858,375 A | 1/1999 | Furminger et al. | |
| 6,248,329 B1 * | 6/2001 | Chandrashekar et al. | 424/191.1 |
| 6,699,703 B1 | 3/2004 | Doucette-Stamm et al. | |
| 6,800,744 B1 | 10/2004 | Doucette-Stamm et al. | |
| 6,936,252 B2 | 8/2005 | Gilbert et al. | |
| 7,074,415 B2 | 7/2006 | Hamel et al. | |
| 7,074,914 B1 | 7/2006 | Doucette-Stamm et al. | |
| 7,081,530 B1 | 7/2006 | Doucette-Stamm et al. | |
| 7,098,023 B1 | 8/2006 | Doucette-Stamm et al. | |
| 7,098,182 B2 * | 8/2006 | Le Page et al. | 424/237.1 |
| 7,115,731 B1 | 10/2006 | Doucette-Stamm et al. | |
| 7,122,368 B1 | 10/2006 | Doucette-Stamm et al. | |
| 7,128,918 B1 | 10/2006 | Hamel et al. | |
| 7,129,339 B1 | 10/2006 | Doucette-Stamm et al. | |
| 7,129,340 B1 | 10/2006 | Doucette-Stamm et al. | |
| 7,135,560 B1 | 11/2006 | Doucette-Stamm et al. | |
| 7,151,171 B1 | 12/2006 | Doucette-Stamm et al. | |
| 7,153,952 B1 | 12/2006 | Doucette-Stamm et al. | |
| 7,262,024 B2 | 8/2007 | Hamel et al. | |
| 7,326,544 B2 * | 2/2008 | Doucette-Stamm et al. | 435/69.3 |
| 7,335,493 B2 * | 2/2008 | Doucette-Stamm et al. | 435/69.3 |
| 7,335,494 B2 * | 2/2008 | Doucette-Stamm et al. | 435/69.3 |
| 7,338,786 B2 * | 3/2008 | Doucette-Stamm et al. | 435/69.3 |
| 7,384,775 B2 * | 6/2008 | Zagursky et al. | 435/252.3 |
| 7,388,090 B2 * | 6/2008 | Doucette-Stamm et al. | 536/23.7 |
| 7,632,515 B2 * | 12/2009 | Gilbert et al. | 424/244.1 |
| 7,635,482 B2 * | 12/2009 | Hamel et al. | 424/190.1 |
| 7,648,708 B2 * | 1/2010 | Gilbert et al. | 424/244.1 |
| 7,713,534 B2 * | 5/2010 | Gilbert et al. | 424/244.1 |
| 7,722,888 B2 * | 5/2010 | Gilbert et al. | 424/244.1 |
| 7,834,166 B2 * | 11/2010 | Doucette-Stamm et al. | 536/23.7 |
| 7,875,439 B2 * | 1/2011 | Doucette-Stamm et al. | 435/69.3 |
| 7,893,238 B2 * | 2/2011 | Doucette-Stamm et al. | 536/23.7 |
| 8,003,775 B2 * | 8/2011 | Doucette-Stamm et al. | 536/23.7 |
| 2003/0022181 A1 | 1/2003 | Cripps et al. | |
| 2003/0077293 A1 | 4/2003 | Hamel et al. | |
| 2003/0091577 A1 | 5/2003 | Gilbert et al. | |
| 2003/0134407 A1 | 7/2003 | Le Pagé et al. | |
| 2003/0232976 A1 | 12/2003 | Hamel et al. | |
| 2004/0129165 A1 | 7/2004 | Cesaroni | |
| 2004/0265933 A1 * | 12/2004 | Le Page et al. | 435/7.32 |
| 2005/0136404 A1 | 6/2005 | Doucette-Stamm et al. | |
| 2005/0158334 A1 | 7/2005 | Contorni et al. | |
| 2006/0078565 A1 * | 4/2006 | Le Page et al. | 424/190.1 |
| 2006/0263378 A1 * | 11/2006 | Le Page et al. | 424/184.1 |
| 2007/0009900 A1 | 1/2007 | Doucette-Stamm et al. | |

(Continued)

FOREIGN PATENT DOCUMENTS

| | | | |
|---|---|---|---|
| EP | 1624064 A2 * | 2/2006 | |
| EP | 1801218 A2 * | 6/2007 | |
| JP | 2008022856 A * | 2/2008 | |
| WO | WO 00/06736 A2 | 2/2000 | |
| WO | WO 00/06738 A2 | 2/2000 | |
| WO | WO 00/58475 A2 | 10/2000 | |
| WO | WO 01/32882 * | 5/2001 | |
| WO | WO 02/079241 * | 10/2002 | |
| WO | WO 02/079241 A2 | 10/2002 | |
| WO | WO 02/079241 A3 | 8/2003 | |
| WO | WO 2005/065382 * | 7/2005 | |

OTHER PUBLICATIONS

Ellis (Chapter 29 of Vaccines, Plotkin, et al. (eds) WB Saunders, Philadelphia, 1998, especially p. 571, paragraph 2).*
Greenspan et al, Nature Biotechnology, 1999, 7:936-937.*
Blythe et al, Protein Science, 2005, 14:246-248.*
Breiman, R.F., et al., "Pneumococcal Bacteremia in Charleston County, South Carolina," *Arch. Intern Med. 150*:1401-1405, American Medical Association (1990).

(Continued)

*Primary Examiner* — Nita M Minnifield
(74) *Attorney, Agent, or Firm* — Sterne, Kessler, Goldstein & Fox P.L.L.C.

(57) ABSTRACT

Novel proteins from *Streptococcus pneumoniae* are described, together with nucleic acid sequences encoding them. Their use in vaccines and in screening methods is also described.

7 Claims, 11 Drawing Sheets

U.S. PATENT DOCUMENTS

| | | | |
|---|---|---|---|
| 2007/0009901 A1 | 1/2007 | Doucette-Stamm et al. | |
| 2007/0009902 A1 | 1/2007 | Doucette-Stamm et al. | |
| 2007/0009903 A1 | 1/2007 | Doucette-Stamm et al. | |
| 2007/0009904 A1 | 1/2007 | Doucette-Stamm et al. | |
| 2007/0009905 A1 | 1/2007 | Doucette-Stamm et al. | |
| 2007/0009906 A1 | 1/2007 | Doucette-Stamm et al. | |
| 2007/0015255 A1 | 1/2007 | Doucette-Stamm et al. | |
| 2007/0015256 A1 | 1/2007 | Doucette-Stamm et al. | |
| 2007/0243207 A1 | 10/2007 | Doucette-Stamm et al. | |
| 2008/0171053 A1* | 7/2008 | Gigliotti et al. | 424/165.1 |
| 2009/0074808 A1* | 3/2009 | Le Page et al. | 424/190.1 |
| 2010/0143415 A1* | 6/2010 | Cripps et al. | 424/244.1 |
| 2010/0278740 A1* | 11/2010 | Gilbert et al. | 424/9.2 |
| 2010/0278819 A1* | 11/2010 | Bossuyt et al. | 424/133.1 |
| 2011/0091506 A1* | 4/2011 | Gibson et al. | 424/244.1 |

OTHER PUBLICATIONS

Breiman, R.F., et al., "Emergence of Drug-Resistant Pneumococcal Infections in the United States," *J. Am. Med. Assoc.* 271:1831-1835, American Medical Association (1994).

Donnelly, J.J., et al., "DNA Vaccines," *Annu. Rev. Immunol.* 15:617-648, Annual Reviews Inc. (1997).

Dopazo, J., et al., "Annotated Draft Genomic Sequence from a *Streptococcus pneumoniae* Type 19F Clinical Isolate," *Microbial Drug Resist.* 7:99-125, Mary Ann Liebert, Inc. (Jun. 2001).

Dougall, W.C., et al., "Antibody-structure-based design of pharmacological agents," *Trends Biotechnol.* 12:372-379, Elsevier Science Ltd. (1994).

Hoskins, J., et al., "Genome of the Bacterium *Streptococcus pneumoniae* Strain R6," *J. Bacteriol.* 183:5709-5717, American Society for Microbiology (Oct. 2001).

Köhler, G. and Milstein, C., "Continuous cultures of fused cells secreting antibody of predefined specificity," *Nature* 256:495-497, Macmillan Journals Ltd. (1975).

Kolkman, M.A., et al., "The Capsule Polysaccharide Synthesis Locus of *Streptococcus pneumoniae* Serotype 14: Identification of the Glycosyl Transferase Gene *cps14E*," *J. Bacteriol.* 178:3736-3741, American Society for Microbiology (1996).

Kovacevic, S., et al., "Secretion of Staphylococcal Nuclease by *Bacillus subtilis*," *J. Bacteriol.* 162:521-528, American Society for Microbiology (1985).

Le Loir, Y., et al, "Direct Screening of Recombinants in Gram-Positive Bacteria Using the Secreted Staphylcoccal Nuclease as a Reporter," *J. Bacteriol.* 176:5135-5139, American Society for Microbiology (1994).

LeBlanc, D.J., et al., "'Conjugal' transfer of plasmid DNA among oral streptococci," *Proc. Natl. Acad. Sci. USA* 75:3484-3487, National Academy of Sciences (1978).

Li, J., et al., "Inactivation of the α C protein antigen gene, *bca*, by a novel shuttle/suicide vector results in attenuation of virulence and immunity in group B *Streptococcus*," *Proc. Natl. Acad. Sci. USA* 94:13251-13256, National Academy of Sciences (1997).

Liebl, W., et al., "Expression, Secretion, and Processing of Staphylococcal Nuclease by *Corynebacterium glutamicum*," *J. Bacteriol.* 174:1854-1861, American Society for Microbiology (1992).

Marck, C., "'DNA Strider': a 'C' program for the fast analysis of DNA and protein sequences on the Apple Macintosh family of computers," *Nucl. Acids Res.* 16:1829-1836, Academic Press (1988).

Miller, J.R., et al., "Secretion and Processing of Staphylococcal Nuclease by *Bacillus subtilis*," *J. Bacteriol.* 169:3508-3514, American Society for Microbiology (1987).

Morrison, S.L., et al., "Chimeric human antibody molecules: Mouse antigen-binding domains with human constant region domains," *Proc. Natl. Acad. Sci. USA* 81:6851-6855, National Academy of Sciences (1984).

Nord, K., et al., "Binding proteins selected from combinatorial libraries of an α-helical bacterial receptor domain," *Nature Biotechnol.* 15:772-777, Nature America, Inc. (1997).

Oultram, J.D. and Young, M., "Conjugal transfer of plasmid pAMβ1 from *Streptococcus lactis* and *Bacillus subtilis* and *Clostridium acetobutylicum*," *FEMS Microbiol. Lett.* 27:129-134, Elsevier (1985).

Poquet, I., et al., "An Export-Specific Reporter Designed for Gram-Positive Bacteria: Application to *Lactococcus lactis*," *J. Bacteriol.* 180:1904-1912, American Society for Microbiology (1998).

Schappert, S.M., "Office Visits for Otitis Media: United States, 1975-90," *Adv. Data, Vital and Health Statistics of the Centers for Disease Control/National Center for health Statistics*, Advance Data No. 214, pp. 1-19, U.S. Department of Health and Human Services (1992).

Shortle, D., "A genetic system for analysis of staphylococcal nuclease," *Gene* 22:181-189, Elsevier Science Publishers (1983).

Siber, G.R., "Pneumococcal Disease: Prospects for a New Generation of Vaccines," *Science* 265:1385-1387, American Association for the Advancement of Science (1994).

Simon, D. and Chopin, A., "Construction of a vector plasmid family and its use for molecular cloning in *Streptococcus lactis*," *Biochimie* 70:559-566, Editions Scientifiques Elsevier (1988).

Stansfield, S.K., "Acute respiratory infections in the developing world: strategies for prevention, treatment and control," *Pediatr. Infect. Dis. J.* 6:622-629, Williams & Wilkins (1987).

Takeda, S.-i., et al., "Construction of chimaeric processed immunoglobulin genes containing mouse variable and human constant region sequences," *Nature* 314:452-454, Macmillan Journals Ltd. (1985).

Tettelin, H., et al., "Complete Genome Sequence of a Virulent Isolate of *Streptococcus pneumoniae*," *Science* 293:498-506, American Association for the Advancement of Science (Jul. 2001).

Van der Vossen, J.M.B.M., et al., "Construction of Cloning, Promoter-Screening, and Terminator-Screening Shuttle Vectors for *Bacillus subtilis* and *Streptococcus lactis*," *Appl. Environ. Microbiol.* 50:540-542, American Society for Microbiology (1985).

Waterfield, N.R., et al., "The isolation of lactococcal promoters and their use in investigating bacterial luciferase synthesis in *Lactococcus lactis*," *Gene* 165:9-15, Elsevier Science B.V. (1995).

Wells, J.M., et al., "Improved cloning vectors and transformation procedure for *Lactococcus lactis*," *J. Appl. Bacteriol.* 74:629-636, Blackwell Scientific Publications Ltd. (1993).

Wells, J.M. and Schofield, K.M., "Cloning and Expression Vectors for Lactococci," in: *Lactic Acid Bacteria: Current Advances in Metabolism, Genetics and Applications*, Bozoğlu, T.F. and Ray, B., eds., Springer Verlag, Berlin, DE, pp. 37-62 (1996).

Baker, C.J. and Edwards, M.S., "Group B streptococcal conjugate vaccines," *Arch. Dis. Child.* 88:375-378, British Medical Association (May 2003).

Bixler, Jr., G.S. Jr. and Atassi, M.Z., "B Cell Recognition of Protein Antigens—Perspectives from the Submolecular Level," in *Synthetic Vaccines* vol. I, Arnon, R., ed., CRC Press, Boca Raton, Florida, pp. 39-71 (1987).

Bowie, J.U., et al., "Deciphering the Message in Protein Sequences: Tolerance to Amino Acid Substitutions," *Science* 247:1306-1310, Association for the Advancement of Science (1990).

Briles, D.E., et al., "The potential for using protein vaccines to protect against otitis media caused by *Streptococcus pneumoniae*," *Vaccine* 19 (Suppl 1):S87-S95, Elsevier (Dec. 2001).

Burgess, W.H., et al., "Possible dissociation of the heparin-binding and mitogenic activities of heparin-binding (acidic fibroblast) growth factor-1 from its receptor-binding activities by site-directed mutagenesis of a single lysine residue," *J. Cell. Biol.* 111:2129-2138, Liss (1990).

Creighton, T.E., ed., *Protein Structure: a practical approach*, IRL Press, Oxford, England, pp. 184-186 (1989).

Creighton, T.E., ed., *Proteins: Structures and Molecular Properties*, W.H. Freeman and Company, New York, N.Y., pp. 314-315 (1984).

Hanniffy, S.B., et al., "Mucosal Delivery of a Pneumococcal Vaccine Using *Lactococcus lactis* Affords Protection against Respiratory Infection," *J. Infect. Dis.* 195:185-193, University of Chicago Press (Jan. 2007).

Houghten, R.A., et al., "Relative Importance of Position and Individual Amino Acid Residues in Peptide Antigen-Antibody Interactions: Implications in the Mechanism of Antigenic Drift and Antigenic Shift," *Vaccines 86: New Approaches to Immunization*, F. Brown et al., eds., pp. 21-25, Cold Spring Harbor Laboratory Press (1986).

Kumar, V., et al., "Amino acid variations at a single residue in an autoimmune peptide profoundly affect its properties: T-cell activation, major histocompatibility complex binding, and ability to block experimental allergic encephalomyelitis," *Proc. Natl. Acad. Sci. U.S.A.* 87:1337-1341, National Academy of Science (1990) and the retraction of this article by Hood, L., et al., at *Proc. Natl. Acad. Sci. U.S.A.* 88:6899, National Academy of Science (1991).

Lazar, E., et al., "Transforming Growth Factor α: Mutation of Aspartic Acid 47 and Leucine 48 Results in Different Biological Activities," *Mol. Cell. Biol.* 8:1247-1252, American Society for Microbiology (1988).

Nosoh, Y. and Sekiguchi, T., "Chapter 7: Concluding Remarks," in *Protein Stability and Stabilization Through Protein Engineering*, (Ellis Horwood series in biochemistry and biotechnology), Ellis Horwood Limited, Guildford, England, pp. 197-217 (1991).

Roitt, I., et al., "Isolation of Pure Antibodies," in *Immunology, Fourth Edition*, Cook, L., ed., Mosby, London, England, pp. 28.7-28.10 (1996).

Steinhoff, M.C., "Animal models for protein pneumococcal vaccine evaluation: A summary," *Vaccine* 25:2465-2470, Elsevier (Mar. 2007).

Török, E., "Staphylococcal and streptococcal infections," *Medicine* 33:97-100, The Medicine Publishing Company (May 2005).

* cited by examiner

FIG. 1

Conservation of ID304L1 gene across a range of serotypes

Genomic DNA from each strain was digested completely with Hin DIII (Roche) and electrophoresed at 12 Volts for 20 hours in 1.0% agarose, transferred onto Hybond N+ (Amersham) membrane by Southern blot and hybridised with the digoxigenin-labelled LID-304 gene probe. Specifically bound DNA probe was identified using the DIG Nucleic Acid Detection Kit (Boehringer Mannheim).

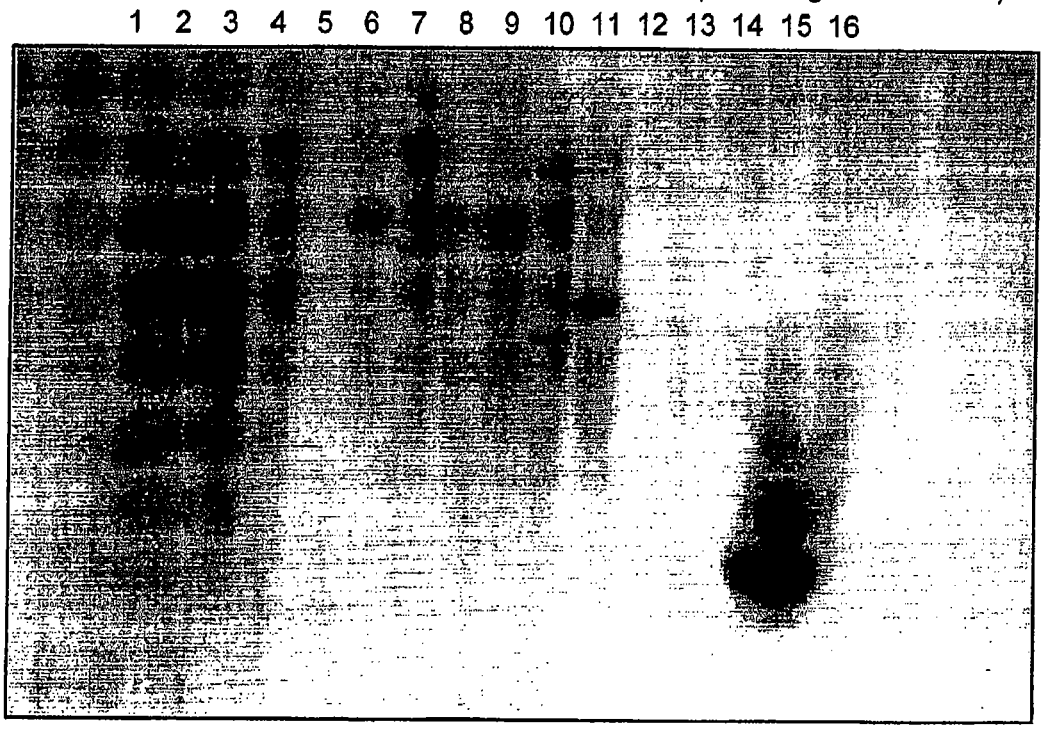

| Lanes: | |
|---|---|
| 1 | S. pneumoniae serotype 5 clinical isolate |
| 2 | S. pneumoniae serotype 18C clinical isolate |
| 3 | S. pneumoniae serotype 23F clinical isolate |
| 4 | S. pneumoniae serotype 7F clinical isolate |
| 5 | S. pneumoniae serotype 1 clinical isolate |
| 6 | S. pneumoniae serotype 6B clinical isolate |
| 7 | S. pneumoniae serotype 4 clinical isolate |
| 8 | S. pneumoniae serotype 3 clinical isolate |
| 9 | S. pneumoniae serotype 19F clinical isolate |
| 10 | S. pneumoniae serotype 9V clinical isolate |
| 11 | S. pneumoniae serotype 14 clinical isolate |
| 12 | S. pneumoniae strain ATCC 49619 (serotype 3) |
| 13 | Moraxella catarrhalis DNA |
| 14 | DIG-labelled markers λHindIII |
| 15 | LID304L1 gene from ATCC49615 |

FIGURE 2 - TABLE 1

| | |
|---|---|
| ID-303A | MAGNSFHLTLTSVSQAGQQTLRHNHSPI (SEQ ID NO:1) |
| ID-303B | ATGGCAGGCAATTCCTTTCACCTAACTCTCACTTCTGTATCTCAGGCAGGA CAACAAACGCTTCGACACAATCACAGTCCTATT (SEQ ID NO:2) |
| ID-305A | MINEEISKEAGQAAQTIISYTIKATKESINLEKEIRKKMNETLEKANGNLK SLMGDEMKIKDLYKKGQLENISIDQIDLKDLKKELNKLGVSFSVMKNKESK NYEIFFQAKDIKVMEYAFKQVIAKENKKEKESILKQIKKYKDLSKNKDKTK EKGKRKVKPNKKDMTREI (SEQ ID NO:3) |
| ID-305B | ATGATAAACGAAGAAATAAGCAAGGAAGCAGGTCAAGCAGCACAAACCATA ATATCATACACAATAAAGGCAACAAAAGAATCAATCAATTTAGAAAAAGAA ATAAGAAAAAAGATGAATGAAACTTTAGAAAAAGCAAATGGAAACTTAAAA AGTCTTATGGGCGATGAAATGAAAATAAAAGACCTCTACAAGAAAGGACAA CTAGAAAATATAAGCATAGATCAAATCGACCTCAAAGACTTAAAAAAAGAA CTAAACAAACTTGGAGTAAGTTTCTCAGTAATGAAAAACAAAGAAAGCAAA AACTATGAAATATTCTTCCAAGCCAAAGACATAAAAGTAATGGAATATGCC TTTAAGCAAGTCATAGCCAAGGAAAATAAAAAAGAAAAAGAAAGTATCCTA AAACAAATAAAGAAATACAAAGACCTATCCAAAAACAAAGATAAGACAAAA GAAAAAGGAAAAAGGAAAGTAAAAGAAAAAGTAAAACCAAACAAAAAAGAT ATGACCAGAGAAATC (SEQ ID NO:4) |
| ID-306A | MKVSKKITLFSLSFAGFVLLTLPQAGKAFELKEDWAFKGGIRYENGKVSK INNGYEVNIKVLDLPSTSAIEWTVRLNGEKQNTNFLAEERTVSKTEDKGR FLHFYIPYGYRGDIVVEAKSGNEVKTWSTKVVDDVYSDSAKSGYFILDGE QILESSWDSVNESYIATLPTVTSGKTVVAWREKGTLNLI (SEQ ID NO:5) |
| ID-306B | ATGAAAGTATCAAAAAAAATTACACTATTTAGTTTGTCTTTTGCAGGTTT TGTTTTATTGACTTTACCTCAAGCAGGAAAGGCTTTTGAACTTAAAGAAG ACTGGGCATTTAAAGGTGGCATTCGATACGAGAATGGGAAAGTCAGCAAA ATTAATAATGGATATGAAGTAAATATTAAAGTGTTAGATTTACCTAGTAC TAGCGCAATCGAATGGACAGTTAGATTGAATGGAGAAAAGCAAAATACTA ACTTCTTAGCGGAGGAAAGAACTGTATCTAAAACTGAAGATAAGGGACGT TTCTTGCACTTTTATATCCCCTATGGATATCGTGGGGATATTGTAGTAGA GGCTAAGAGTGGAAACGAAGTGAAGACTTGGTCTACTAAGGTAGTTGACG ATGTTTATTCAGATTCTGCTAAGAGTGGCTACTTTATTCTCGATGGGGAA CAAATCTTAGAAAGTTCATGGGATTCCGTAAATGAGTCTTATATTGCAAC GCTTCCAACTGTAACATCAGGAAAAACTGTTGTTGCTTGGCGTGAAAAAG GAACTCTTAATTTAATT (SEQ ID NO:6) |
| ID-304L1A | MELVLPNNYVVLEQEEMMYLDGGFSIPRWPVATAINIAFNGVLGGGAISL VRNYIRNYGLRRVTSAIAGAAARYVGVRVANRVAGFALSAINGFAAWMSI GDAITTIWANNDVNRRDPNLNALW (SEQ ID NO:7) |
| ID-304L1B | ATGGAACTCGTATTACCAAATAATTATGTTGTTCTTGAGCAAGAAGAGAT GATGTATCTTGATGGGGGATTTTCTATTCCGAGATGGCCTGTTGCAACAG CCATTAATATAGCTTTTAATGGTGTTTTAGGTGGAGGAGCAATCAGTCTA GTTAGAAATTATATTCGTAATTATGGTTTGCGGCGAGTTACAAGCGCAAT TGCTGGAGCAGCTGCAAGATATGTTGGGGTACGAGTTGCAAATAGAGTGG CAGGATTTGCACTGTCTGCTATTAATGGATTTGCAGCTTGGATGTCAATT GGCGATGCTATTACAACAATCTGGGCCAACAATGATGTAAATAGGAGAGA CCCAAATTTAAACGCCTTGTGGTAA (SEQ ID NO:8) |

FIGURE 3 - TABLE 2

Bracketed residues represent an alternative to the residue immediately preceeding. IUPAC nucleic acid ambiguity codes have been amplied.

ID-204A  MKDTFKNVLSFEFWQKFGKALMVVIAVMPAAGLMISIGKSIVMINPTFAP
LVITGGILEQIGWGVIGNLHILFALAIGGSWAKERAGGAFAAGLAFILIN
RITGTIFGVSGDMLKNPDAMVTTFFGGSIKVADYFISVLEAPALNMGVFV
GIISGFVGATAYNKYYNFRKLPDALSFFNGKRFVPFVVILRSAIAAILLA
AFWPVVQTGINNFGIWIANSQETAPILAPFLYGTLERLLLPFGLHHMLTI
PMNYTALGGTYDILTGAAKGTQVFGQDPLWLAWVTDLVNLKGTDASQYQH
LLDTVHPARFKVGQMIGSFGILMGVIVAIYRNVDADKKHKYKGMMIATAL
ATFLTGVTEPIEYMFMFIATPMYLVYSLVQGAAFAMADVVNLRMHSFGSI
EFLTRTPIAISAGIGMDIVNFVWVTVLFAVIMYFIANFMIQKFNYATPGR
NGNYETAEGSEETSSEVKVAAGSQAVNIINLLGGRVNIVDVDACMTRLRV
TVKDADKVGNAEQWKAEGAMGLVMKGQGVQAIYGPKADILKSDIQDILDS
GEIIPETLPSQMTEAQQNTVHFKDLTEEVYSVADGQVVALEQVKDPVFAQ
KMMGDGFAVEPANGNIVSPVSGTVSSIFPTKHAFGIVTEAGLEVLVHIGL
DTVSLEGKPFTVHVAEGQKVAAGDLLVTADLDAIRAAGRETSTVVVFTNG
DAIKSVKLEKTGSLAAKTAVAKVEL* (SEQ ID NO:9)

ID-204B  GGTAAGGCTTTGATGGTAGTTATCGCGGTTATGCCGGCTGCTGGTTTGATG
ATTTCAATCGGTAAGTCTATCGTGATGATTAACCCAACCTTTGCACCACTT
GTCATCACAGGTGGAATTCTTGAGCAAATCGGTTGGGGGGTTATCGGTAAC
CTTCACATTTTGTTTGCCCTAGCCATTGGAGGAAGCTGGGCTAAAGAACGT
GCTGGTGGTGCTTTCGCCGCTGGTCTTGCCTTCATCTTGATTAACCGTATC
ACTGGTACAATCTTTGGTGTATCAGGCGATATGTTGAAAAATCCAGATGCT
ATGGTAACTACTTTCTTTGGTGGTTCAATCAAAGTTGCTGATTACTTTATC
AGTGTTCTTGAAGCTCCAGCCTTGAACATGGGGGTATTCGTAGGGATTATC
TCAGGTTTTGTAGGGGCAACTGCTTACAACAAATACTACAACTTCCGTAAA
CTTCCTGATGCACTTTCATTCTTCAACGGGAAACGTTTCGTACCATTTGTA
GTTATTCTTCGTTCAGCAATCGCTGCAATTCTACTTGCTGCTTTCTGGCCA
GTAGTTCAAACAGGTATCAATAACTTCGGTATCTGGATTGCCAACTCACAA
GAAACTGCTCCAATTCTTGCACCATTCTTGTATGGTACTTTGGAACGTTTG
CTCTTGCCATTTGGTCTTCACCACATGTTGACTATCCCAATGAACTACACA
GCTCTTGGTGGTACTTATGACATTTTAACTGGTGCAGCTAAAGGTACTCAA
GTATTCGGTCAAGACCCACTATGGCTTGCATGGGTAACAGACCTTGTAAAC
CTTAAAGGTACTGATGCTAGTCAATATCAACACTTGTTAGATACAGTACAT
CCAGCTCGTTTCAAAGTTGGACAAATGATCGGTTCATTCGGTATCTTGATG
GGTGTGATTGTTGCTATCTACCGTAATGTTGATGCTGACAAGAAACATAAA
TACAAAGGTATGATGATTGCAACAGCTCTTGCAACATTCTTGACAGGGGTT
ACTGAACCAATCGAATACATGTTCATGTTCATCGCAACACCTATGTATCTT
GTTTACTCACTTGTTCAAGGTGCTGCCTTCGCTATGGCTGACGTCGTAAAC
CTACGTATGCACTCATTCGGTTCAATCGAGTTCTTGACTCGTACACCTATT
GCAATCAGTGCTGGTATTGGTATGGATATCGTTAACTTCGTTTGGGTAACT
GTTCTCTTTGCTGTAATCATGTACTTTATCGCAAACTTCATGATTCAAAAA
TTCAACTACGCAACTCCAGGGCGCAACGGAAACTACGAAACTGCTGAAGGT
TCAGAAGAAACCAGCAGCGAAGTGAAAGTTGCAGCAGGCTCTCAAGCTGTA

FIGURE 3 - TABLE 2 CONT'D

```
            AACATTATCAACCTTCTTGGTGGACGTGTAAACATCGTTGATGTTGATGCA
            TGTATGACTCGTCTTCGTGTAACTGTTAAAGATGCAGATAAAGTAGGAAAT
            GCAGAGCAATGGAAAGCAGAAGGAGCTATGGGTCTTGTCATGAAAGGACAA
            GGGGTTCAAGCTATCTACGGTCCAAAAGCTGACATTTTGAAATCTGATATC
            CAAGATATCCTTGATTCAGGTGAAATCATTCCTGAAACTCTTCCAAGCCAA
            ATGACTGAAGCACAACAAAACACTGTTCACTTCAAAGATCTTACTGAGGAA
            GTTTACTCAGTAGCAGACGGTCAAGTTGTTGCTTTGGAACAAGTAAAGGAT
            CCAGTATTTGCTCAAAAAATGATGGGTGATGGATTTGCAGTAGAACCTGCA
            AATGGAAACATTGTATCTCCAGTTTCAGGTACTGTGTCAAGCATCTTCCCA
            ACAAAACATGCTTTTGGTATTGTGACGGAAGCAGGTCTTGAAGTATTGGTT
            CACATTGGTTTGGACACAGTAAGTCTTGAAGGTAAACCATTTACAGTTCAT
            GTTGCTGAAGGACAAAAAGTTGCAGCAGGAGATCTCCTTGTCACAGCTGAC
            TTGGATGCTATCCGTGCAGCAGGACGTGAAACTTCAACAGTAGTTGTCTTC
            ACAAATGGTGATGCAATTAAATCAGTTAAGTTAGAAAAAACAGGTTCTCTT
            GCAGCTAAAACAGCAGTTGCTAAAGTAGAATTGTAA (SEQ ID NO:10)
```

ID-212A   MLLQKELIPMIEANLPNMAYAEKDIAKFFLKQQPLNN(D)YSC(S)KALC
          EYLNVSKATLTRFAKKCGFKGFRQFIFKYQEMIHEKEKLALYTEATEKVL
          SDYEEMLRKTYTVLDEVQLERIAEMIETAERVYLYGKGSSVLALQEMKMR
          FMRLGVIGEVLSDEDMILWSSLLLNENCLVIGASISGQTDIVLEGLQKAA
          DKGAKTVLMTTRKFDEEDCFFDELLLLASTDHLSYGNRISPQFPILLITD
          CLFSNYLESPERQYYYNQTIIHKEE* (SEQ ID NO:11)

ID-212B   ATGTTACTGCAAAAAGAACTAATTCCAATGATAGAAGCTAACTTACCAAAT
          ATGGCATATGCTGAAAAAGACATTGCTAAATTCTTCTTAAAACAGCAACCT
          CTGAATRATTATTCATSTAARGCATTGTGCGAATACCTTAATGTATCCAAA
          GCAACATTGACTCGATTTGCGAAAAAATGTGGTTTTAAAGGTTTTAGACAA
          TTCATTTTCAAATACCAAGAGATGATTCATGAGAAAGAAAAGTTGGCATTA
          TATACAGAGGCAACAGAAAAAGTTTTATCCGACTATGAGGAAATGTTGAGA
          AAAACTTACACGGTTCTTGATGAAGTTCAACTTGAGCGTATTGCTGAGATG
          ATAGAAACTGCTGAGCGTGTATATCTCTACGGTAAAGGAAGTTCTGTTCTT
          GCTTTACAAGAAATGAAGATGAGATTTATGCGTCTCGGAGTGATTGGTGAA
          GTATTATCAGACGAGGATATGATTTTGTGGAGTAGCTTACTACTTAATGAA
          AATTGCCTTGTCATTGGAGCATCCATTTCAGGTCAAACTGATATTGTACTA
          GAAGGTCTACAAAAAGCTGCAGATAAAGGCGCTAAAACAGTTTTAATGACT
          ACAAGAAAATTTGACGAAGAAGATTGTTTCTTTGATGAACTATTGTTATTA
          GCTTCGACCGATCATCTCTCGTATGGCAATCGCATATCACCTCAGTTTCCA
          ATACTTTTAATTACAGACTGCTTATTCTCTAATTATCTGGAAAGTCCAGAG
          AGACAATATTATTACAATCAAACTATTATCCATAAGGAGGAATAA (SEQ ID NO:12)

ID-213A   MNKSRLGRGRHGKTRHILLALIGILAISICLLGGFIAFKIYQQKSFEQKI
          ESLKKEKDDQLSEGNQKEHFRQGQAEVIAYYPLQGEKVISSVRELINQDV
          KDKLESKDNLVFYYTEQEESGLKGVVNRNVTKQIYDLVAFKIEETEKTSL
          GKVHLTEDGQPFTLDQLFSDASKAKEQLIKELTSFIEDKKIEQDQSEQIV
          KNFSDQDLSAWNFDYKDSQIILYPSPVVENLEEIALPVSAFFDVIQSSYL
          LEKDAALYQSYFDKKHQKVVALTFDDGPNPATTPQVLETLAKYDIKAFFV
          LGKNVSGNEDLVKRIKSEGHVVGNHSWSHPILSQLSLDEAKKQITDTEDV
          LTKVLGSSSKLMRPPYGAITDDIRNSLDLSFIMWDVDSLDWKSKNEASIL
          TEIQYQVANGSIVLMHDIHSPTVNALPRVIEYLKNQGYTFVTIPEMLNTR
          LKAHELYYSRDE* (SEQ ID NO:13)

FIGURE 3 - TABLE 2 CONT'D

ID-213B    ATGAATAAAAGTAGACTAGGACGTGGCAGACACGGGAAAACGAGACATRT
           ATTATTGGCTTTGATTGGTATTTTAGCAATTTCTATTTGCCTATTAGGCG
           GATTTATTGCTTTTAAGATCTACCAGCAAAAAAGTTTTGAGCAAAAGATT
           GAATCGCTCAAAAAAGAGAAAGATGATCAATTGAGTGAGGGAAATCAGAA
           GGAGCATTTTCGTCAGGGGCAAGCCGAAGTGATTGCCTATTATCCTCTCC
           AAGGGGAGAAAGTGATTTCCTCTGTTAGGGAGT(C)TGATAAATCAAGAT
           GTTAAGGACAAGCTAGAAAGTAAGGACAATCTTGTTTTCTACTATACAGA
           GCAAGAAGAGTCAGGTTTAAAGGGAGTCGTTAATCGTAATGTGACCAAAC
           AAATCTATGATTTAGTTGCTTTTAAGATTGAAGAGACTGAAAAGACCAGT
           CTAGGAAAGGTTCACTTAACAGAAGATGGGCAACCTTTTACACTTGACCA
           ACTGTTTTCAGATGCTAGTAAGGCTAAGGAACAGCTGATAAAAGAGTTGA
           CCTCCTTCATAGAGGATAAAAAAAATAGAGCAAGACCAGAGTGAGCAGATT
           GTAAAAAACTTCTCTGACCAAGACTTGTCTGCATGGAATTTTGATTACAA
           GGATAGTCAGATTATCCTTTATCCAAGTCCTGTGGTTGAAAATTTAGAAG
           AGATAGCCTTGCCAGTATCTGCTTTCTTTGATGTTATCCAATCTTCGTAC
           TTACTCGAAAAAGATGCGGCCTTGTACCAATCTTACTTTGATAAGAAACA
           TCAAAAAGTTGTCGCTCTAACCTTTGATGATGGTCCAAATCCAGCAACGA
           CCCCGCAGGTATTAGAGACCCTAGCTAAATATGATATTAAAGCGA(_)C
           (_)T(_)TTCTTTGTGCTTGGGAAAAATGTTTCTGGGAATGAGGACTTGG
           TGAAGAGGATAAAATCTGAAGGTCATGTTGTTGGAAACCATAGCTGGAGC
           CATCCGATTCTCTCGCAACTCTCTCTTGATGAAGCTAAAAAGCAGATTAC
           TGATACTGAGGATGTGCTAACTAAAGTGCTGGGTTCTAGTTCTAAACTCA
           TGCGTCCACCTTATGGTGCTATTACAGATGATATTCGCAATAGCTTGGAT
           TTGAGCTTTATCATGTGGGATGTGGATAGTCTGGACTGGAAGAGTAAAAA
           TGAAGCATCTATTTTGACAGAAATTCAGTATCAAGTAGCTAATGGCTCTA
           TCGTTTTGATGCATGATATTCACAGTCCGACAGTCAATGCCTTGCCAAGG
           GTCATTGAGTATTTGAAAAATCAAGGTTATACCTTTGTGACCATACCAGA
           GATGCTCAATACTCGCCTAAAAGCTCATGAGCTGTACTATAGTCGTGATG
           AATAA (SEQ ID NO:14)

ID-214A    MFVKKGDKVRVIAGKDKGTEAVVLTALPKVNKVIVEGVNIVKKHQRPTNE
           LPQGGIIEKEAAIHVSNVQVLDKNGVAGRVGYKFVDGKKVRYNKKSGEVL
           D* (SEQ ID NO:15)

ID-214B    ATGTTTGTAAAAAAAGGCGACAAAGTTCGCGTAATCGCTGGTAAAGATAAG
           GGAACAGAAGCTGTTGTCCTTACTGCCCTTCCAAAAGTAAACAAAGTTATC
           GTTGAAGGTGTTAACATTGTTAAGAAACACCAACGTCCAACTAACGAGCTT
           CCTCAAGGTGGTATCATCGAGAAAGAAGCAGCTATCCACGTATCAAACGTT
           CAAGTTTTGGACAAAAATGGTGTAGCTGGTCGTGTTGGATACAAATTTGTA
           GACGGTAAAAAAGTTCGCTACAACAAAAAATCAGGCGAAGTGCTTGATTAA (SEQ ID NO:16)

ID-215A    MKKISNFCMLLLLLLCTTFFVFNVNYTREVVRIQEMGKTVDSLDLYLKDIN
           EPAASVLRFFEDVSKEYKVSIIKTDSGDEVVKSGVFDKDTFPYQEFGISS
           LDFTTDGEGVYSNKEISNKLGTIPTFLKAKPIQLMTFQTYIKDTSRSLNG
           RYTITSTQEMDKDRIVQKWSDFFKIDQATLLEPTYKSAVEVINRDLLLSA
           IVFVLAILLLVLVTVYQPMMEMKRVGVQKLLGFQDRAVLADVVKGNLYLL
           LGGALVINLGVFFLLDYKPKDLFPMLWLSHFLLLQLYLFISWLTYLLIQK
           MTISSLLKGFSSFKFGLIFNYVMKIGTTILLTALLIGVGRSLEQENKELA
           YQQQWVSQGNYLTLETFKLNDNLWQEELAGSGKSTDYFYRFYQDLVEKTQ
           AGYVQSSSLPVKNFVQSEQIQQYQLTDTVDVYYANRNFLKSKGFKLPNTG
           IKKVILMPASTKGEEDKNQLLGKLIAFHSMKYEEQQKRTIEEMDVEIAYY
           EGDWSFFPYSDKRKENLSNPIISLVNDSDMMWDEKASLSTTGLNNPIKIE
           NTVQHQKEITELVEKLSDGNYLKFSSIQAIQQEKVDSYRDAVRNFNLLFA
           LFGLLSMMISYFLLVTTFLLKRRDIITKKFMGWKLVDRYRPLLVLLLLGY
           SFPLLVLIFFAHAFLPLLLFAGFTCLDILFVLGLASRMEKRSLVELLKGG
           IL* (SEQ ID NO:17)

FIGURE 3 - TABLE 2 CONT'D

ID-215B  ATGAAAAAAATCAGTAATTTCTGTATGTTACTCCTGCTTCTGTGTACCACT
TTTTTTGTTTTTAATGTAAACTATACACGAGAAGTGGTTCGGATTCAAGAA
ATGGGAAAGACTGTAGATTCTTTGGATTTGTATTTGAAAGATATTAACGAA
CCTGCAGCGTCTGTTCTTCGATTTTTTGAGGATGTATCAAAGGAGTATAAA
GTCTCCATCATCAAAACAGACAGTGGTGATGAGGTGGTCAAGTCTGGTGTT
TTTGATAAAGATACCTTCCCCTACCAAGAGTTTGGGATTTCTTCTCTTGAT
TTTACCACAGATGGTGAAGGAGTCTATAGTAATAAAGAAATTTCCAATAAA
CTTGGTACGATTCCGACCTTTCTAAAAGCCAAACCTATTCAGCTTATGACT
TTTCAAACCTATATCAAGGATACATCTCGTAGTTTAAATGGTCGCTATACG
ATAACTTCTACACAAGAGATGGACAAGGATAGGATTGTACAGAAATGGAGC
GATTTTTTCAAGATAGACCAGGCTACCTTGCTAGAGCCGACCTACAAAAGT
GCAGTGGAAGTCATAAATCGAGATTTGCTTTTATCTGCCATTGTTTTGTC
TTGGCTATTTTGCTTCTTGTGTTAGTGACAGTGTATCAACCGATGATGGAG
ATGAAAAGAGTTGGGGTACAAAAATTACTTGGTTTTCAAGATAGGGCTGTT
TTAGCTGATGTTGTAAAAGGCAACCTTTACCTCCTCCTAGGTGGGGCTCTT
GTGATCAATCTAGGCGTGTTTTTCTTGCTTGATTATAAGCCAAAAGATTTG
TTTCCTATGCTGTGGTTGTCTCATTTTTTGCTGTTGCAGCTTTATCTCTTT
ATCAGTTGGTTGACTTACCTCTTAATCCAAAAAATGACAATCAGCTCTCTG
CTGAAAGGTTTTTCATCTTTCAAATTTGGTCTTATCTTCAATTATGTGATG
AAAATAGGGACAACTATTTTACTGACGGCCTTACTGATTGGGGTGGGCAGA
AGTTTAGAACAAGAAAACAAAGAACTTGCTTATCAGCAACAGTGGGTAAGT
CAAGGTAATTACCTGACCTTAGAAACCTTCAAACTCAATGATAATCTGTGG
CAAGAAGAGCTAGCAGGGTCAGGGAAATCTACAGATTATTTCTATCGATTT
TATCAGGATTTGGTAGAAAAAACGCAGGCGGGCTATGTGCAGAGTAGCAGT
CTTCCTGTAAAAAATTTTGTCCAATCAGAACAGATTCAGCAATATCAGTTA
ACAGATACGGTGGATGTTTACTATGCCAATCGCAATTTTCTAAAGAGCAAG
GGATTCAAGCTACCAAATACCGGTATTAAAAAAGTTATTTTGATGCCAGCA
AGTACGAAAGGTGAAGAAGATAAAAATCAGCTCTTGGGGAAGTTAATTGCC
TTTCATTCGATGAAGTATGAAGAGCAGCAAAAACGAACGATAGAGGAGATG
GATGTCGAGATTGCCTATTATGAAGGAGATTGGTCATTTTTCCCATATAGT
GATAAGCGAAAGGAAAATCTCTCCAATCCAATTATTAGCTTGGTCAATGAT
TCTGATATGATGTGGGATGAGAAAGCCTCCCTGTCAACAACTGGCTTAAAT
AATCCGATTAAAATTGAAAATACGGTTCAACATCAAAAAGAGATTACAGAG
TTAGTTGAGAAATTGTCAGATGGAAATTATTTAAAATTTTCATCTATTCAA
GCCATTCAACAAGAGAAAGTGGATTCTTATCGAGATGCTGTTCGGAATTTT
AACCTACTCTTTGCTTTGTTTGGTCTCCTTAGCATGATGATTTCCTACTTC
TTACTAGTAACAACTTTCTTATTGAAGCGCAGGGATATCATTACCAAGAAG
TTTATGGGGTGGAAACTGGTCGATCGCTACCGTCCTCTCCTCGTTCTGCTC
TTGCTGGGCTATAGTTTCCCTCTTCTAGTCTTGATTTTCTTTGCCCATGCG
TTCTTACCACTTCTACTGTTTGCAGGTTTTACATGTCTGGATATACTATTT
GTGCTAGGCTTAGCTTCTAGGATGGAGAAAAGAAGTCTAGTAGAGTTATTG
AAAGGGGGCATCTTATGA (SEQ ID NO:18)

ID-216A  MPITAADIRREVKEKNVTFIRLMFSDILGTMKNVEIPATDEQLDKVLSNK
VMFDGSSIEGFVRINESDMYLYPDLDTWTVFPWGDENGSVAGLICDVYTT
EGEPFAGDPRGNLKRALRHMEEVGFKSFNLGPEPEFFLFKLDENGDPTLE
VNDKGGYFDLAPTDLADNTRREIVNVLTKMGFEVEASHHEVAVGQHEIDF
KYDEVLRACDKIQIFKLVVKTIARKHGLYATFMAKPKFGIAGSGMHCNMS
LFDAEGNNAFFDPNDPKGMQLSETAYHFLGGLIKHAYNYTAIMNPTVNSY
KRLVPGYEAPVYIAWAGRNRSPLVRVPASRGMGTRLELRSVDPMANPYVA
MAVLLEVGLYGIENKIEAPAPIEENIYIMTAEERKEAGITDLPSTLHNAL
KALTEDEVVKAALGDHIYTSFLEAKRIEWASYATFVSQWEIDNYLDLY* (SEQ ID NO:19)

FIGURE 3 - TABLE 2 CONT'D

ID-216B ATGCCAATCACAGCTGCAGATATTCGTCGTGAAGTCAAGGAAAAAAATGTT
ACCTTTATTCGTCTTATGTTCTCAGATATTTTGGGAACCATGAAAAACGTC
GAAATTCCTGCTACAGATGAACAGTTAGATAAGGTCTTGTCGAACAAGGTT
ATGTTTGATGGATCTTCTATTGAAGGTTTTGTACGTATCAATGAGTCGGAT
ATGTACTTGTACCCGGACTTGGATACATGGACAGTCTTCCCTTGGGGAGAT
GAAAATGGAAGTGTTGCAGGTCTGATCTGTGATGTT(C)TATACAACAGAA
GGTGAACCATTTGCGGGTGACCCTCGTGGTAATTTGAAACGAGCTCTTCGT
CACATGGAAGAAGTTGGATTCAAATCCTTCAACCTTGGTCCAGAGCCAGAA
TTCTTCCTATTTAAGTTGGATGAAAATGGGGACCCAACACTTGAAGTGAAT
GACAAGGGTGGCTACTTTGACTTGGCACCTACTGACCTTGCGGACAACACA
CGTCGTGAGATTGTGAATGTCTTGACCAAAATGGGATTTGAAGTAGAAGCG
AGTCACCACGAGGTTGCGGTTGGACAGCATGAGATTGACTTTAAGTACGAT
GAAGTTCTCCGTGCTTGTGATAAGATTCAAATCTTTAAGCTTGTTGTTAAA
ACCATTGCTCGCAAACACGGACTTTACGCAACATTTATGGCGAAGCCAAAA
TTTGGTATTGCTGGATCAGGTATGCACTGTAATATGTCCTTGTTTGATGCA
GAAGGAAATAACGCCTTCTTTGATCCAAATGATCCAAAAGGAATGCAGTTG
TCAGAAACAGCTTACCATTTCCTAGGCGGTTTGATCAAGCATGCTTACAAC
TATACTGCCATCATGAACCCAACAGTTAACTCATACAAACGTTTGGTTCCA
GGTTATGAAGCGCCTGTTTACATTGCTTGGGCTGGTCGTAACCGTTCGCCA
CTTGTGCGCGTACCTGCTTCACGTGGTATGGGAACTCGTCTTGAGTTGCGT
TCAGTGGATCCAATGGCGAACCCTTACGTTGCTATGGCTGTTCTTTTGGAA
GTTGGTTTGTATGGTATTGAAAATAAAATCGAAGCACCAGCTCCTATCGAA
GAAAATATCTACATCATGACAGCAGAAGAGCGCAAGGAAGCTGGTATTACA
GACCTTCCATCAACTCTTCACAACGCTTTGAAAGCTTTGACAGAAGATGAA
GTGGTTAAAGCTGCTCTCGGAGATCACATCTATACTAGCTTCCTTGAAGCC
AAACGAATCGAATGGGCAAGTTATGCAACCTTCGTTTCACAATGGGAAATT
GATAATTATTTAGACCTTTACTAA (SEQ ID NO:20)

ID-217A MVYLVLGILLLLLYVFATPESIKGTVNIVAMVCILVALLILLVLSFLKIF
QLPTEIFLAIAMLILAYFSVRDITLMPVKKSKRR* (SEQ ID NO:21)

ID-217B ATGGTCTATTTAGTCCTAGGAATTTTACTGCTCCTACTCTATGTATTTGCG
ACACCAGAAAGCATTAAAGGGACTGTCAATATCGTCGCTATGGTATGTATT
TTAGTGGCACTCTTGATTTTATTGGTTCTATCTTTTCTGAAAATTTTTCAA
TTACCAACAGAAATATTCCTAGCAATAGCCATGTTGATCCTAGCTTACTTT
AGTGTTAGAGACATCACACTCATGCCAGTCAAAAAAAGTAAAAGAAGATAA (SEQ ID NO:22)

ID-219A SGLGLNFYALSSYYLGSFLAPLVYFFDLTNMPDAIYLTTLLKFGLIGLST
FFSLNKLFQSIPQILKLALSTSYALMSFTVSQLEIKTWLDVFILIPLIIT
GLHLLITEKKLLLYFTSLSILFIQNYYFGYMTVLFLIFWYLCQISWDFKT
RKSSVLDFIVISFLAGMASLIMTLPTLFDLQTHGEKLTEVTKFQTESSWY
LDLFAKQFIGSFDTTKYGAIPMIFVGLFPFILTILFFTLKSIKFHVKLIY
VIFFAFLIASFYIEALDLFWQGMHTPNMFLHRYAWIFSTLLIYTAAEVLK
RLKELKVWNFLVSLFLVVAGFLATIYLKSHYSLTDLNILLTLEFLVVYSL
LLLAVIKKFISVNLFAILISLFILVEMSLNASSQMDGIAKEWGFASRSAY
SRDIPAMESFSTYIGNQFTRTEKLQTQTGNDSMKFNYNGISQFSSVRNRS
SSSTLDKLGFKSSGTNLNLRYANNSILADSLFGIQYNISDSPIDKYGFKD
IYQKDNLTLYENQYSLPIAVASQSVYNDVKFNEHTLDNQASFLNQLANVN
FDYFSPIPYEKTEKIENTNDLISVTSSSNEDAAIQYQIEVPENSQVYLSF
INLHFSNDKQKKVDILVNGEKKTFTTDNVFSFFNLGYTKEKKTFNINVSF
FGNSQVSFESPTFYRLDTKTFTEAIQKIKEQPVTVSTSKNKVFATYDVQQ
DTSIFFTIPYDKGWSAYQDGKKIEIKQAQTGFMKVDIPKGKGTITLSFIP
NGFITGAICSFTSLLLFGIYNHRRKSSKA* (SEQ ID NO:23)

FIGURE 3 - TABLE 2 CONT'D

ID-219B AGTGGTCTAGGGCTAAACTTCTATGCCCTATCTAGTTATTACTTGGGTAGT
TTTCTCGCGCCTCTGGTTTACTTTTTTGATCTAACGAATATGCCAGATGCT
ATCTATCTGACAACTCTCTTAAAATTTGGATTGATTGGTCTGTCAACCTTT
TTTAGTTTGAATAAATTGTTTCAATCTATCCCTCAGATTTTAAAACTAGCC
TTATCTACTTCCTATGCTCTGATGAGTTTCACTGTCAGTCAATTAGAGATA
AAAACCTGGCTAGATGTTTTTATCTTGATTCCTTTAATTATAACTGGTTTA
CATCTACTGATAACTGAAAAGAAACTCCTATTGTACTTTACAAGTCTGTCA
ATCTTATTTATTCAAAATTATTATTTTGGATATATGACAGTATTGTTTCTT
ATTTTCTGGTATCTCTGTCAAATTTCGTGGGACTTTAAGACTCGAAAATCA
TCTGTTCTTGATTTCATAGTTATCTCCTTTTTAGCTGGTATGGCTAGTTTG
ATTATGACTCTTCCCACTCTATTTGATTTACAGACACATGGGGAAAAATTG
ACTGAAGTTACAAAGTTTCAAACTGAAAGTAGCTGGTATCTTGATCTCTTT
GCTAAGCAATTCATTGGTTCCTTTGACACAACAAAGTATGGGGCCATCCCA
ATGATTTTGTTGGACTATTTCCCTTTATTTTGACCATTTTATTTTTTACG
CTGAAATCTATTAAGTTTCACGTGAAACTCATATATGTAATATTCTTTGCA
TTTCTAATTGCAAGCTTTTACATAGAAGCTCTTGACTTATTTTGGCAAGGC
ATGCATACTCCAAACATGTTTTTACATCGCTATGCTTGGATTTTCTCTACC
TTGTTAATTTACACAGCAGCAGAAGTCTTAAAGCGTCTGAAAGAACTTAAA
GTCTGGAATTTTTTAGTTTCGCTTTTTCTTGTAGTAGCAGGATTTTTAGCT
ACCATCTATCTAAAATCGCATTATTCTTTTTAACAGATTTGAATATTCTG
CTTACTCTTGAATTTTTGGTTGTCTATTCTCTTTTACTCCTTGCAGTTATC
AAAAAGTTTATATCTGTGAATCTATTTGCCATTCTAATCTCTTTATTTATA
CTGGTTGAAATGAGTTTAAATGCTTCATCTCAAATGGACGGAATTGCTAAG
GAATGGGGATTTGCTTCTCGAAGTGCTTATAGTCGAGATATCCCAGCTATG
GAATCTTTCTCAACATATATTGGAAATCAATTTACTCGTACTGAAAAACTA
CAAACTCAGACAGGAAATGACAGTATGAAATTCAACTACAATGGAATCTCT
CAATTTTCATCTGTTCGAAATCGTTCATCAAGCTCTACTTTAGATAAACTT
GGTTTTAAATCCTCTGGGACTAATCTCAATCTCCGATATGCAAATAATAGT
ATTTTGGCTGATAGTTTATTTGGTATCCAGTACAATATCTCAGACAGTCCT
ATTGATAAGTATGGCTTTAAAGATATCTATCAAAAAGATAATCTTACCCTA
TATGAAAATCAATACTCTCTTCCGATTGCAGTTGCGAGTCAATCTGTTTAC
AATGATGTCAAGTTCAATGAACATACCTTGGATAATCAGGCCTCATTTTTA
AATCAACTTGCTAACGTCAATTTTGATTATTTTCTCCAATACCTTATGAA
AAAACAGAAAAAATAGAAAATACTAATGATTTGATTAGTGTCACAAGTTCT
TCAAATGAAGATGCAGCAATCCAGTATCAAATTGAAGTTCCAGAAAACAGC
CAAGTTTATCTCTCTTTCATAAACCTTCACTTTTCTAACGATAAACAAAAG
AAGGTTGACATCCTTGTAAATGGTGAAAAAAAGACTTTTACAACTGATAAT
GTCTTCTCCTTCTTTAATCTAGGATATACTAAAGAGAAAAAAACTTTCAAT
ATCAATGTTAGTTTCCCTGGAAATTCACAAGTATCATTTGAATCTCCTACC
TTCTATCGTTTAGATACCAAAACTTTCACCGAGGCAATTCAAAAAATTAAA
GAACAACCTGTCACAGTATCAACTTCTAAAAACAAGGTTTTTGCTACATAT
GATGTCCAACAAGATACATCTATTTTCTTCACCATTCCTTATGACAAAGGT
TGGTCTGCCTACCAAGATGGTAAGAAAATAGAAATTAAACAAGCTCAAACT
GGATTTATGAAAGTTGACATTCCCAAGGGGAAAGGAACTATTACACTTTCC
TTCATTCCCAATGGTTTTATTACTGGAGCAATCTGTTCCTTTACTTCTCTC
TTACTATTTGGAATCTATAATCACAGACGAAAGTCATCTAAGGCATAA (SEQ ID NO:24)

ID-220A MNEKVFRDPVHNYIHVNNQIIYDLINP(T)Q(K)EFQRLRRIKQLGTSSY
TFHGGEHSRFSHCLGVYEIARRITEIFEEKYPEEWNPAESLLTMTAALLH
DLGHGAYSHTFEHLFDTDHEAITQEIIQNPETEIHQVLLQVAPDFPEKVA
SVIDHTYPNKQVVQLISSQIDADRMDYLLRDSYFTGASYGEFDLTRILRV
IRPIENGIAFQRNGMHAIEDYVLSRYQMYMQVYFHPATRAMEVLLQNLLK
RAKELYPEDKDFFARTSPHLLPFFEKNVTLTDYLALDDGVMNTYFQLWMT
SPDKILADLSHRFVNRKVFKSITFSQEDQDQLTSMRKLVEDIGFDPDYYT
AIHKNFDLPYDIYRPESENPRTQIEILQKNGELAELSSLSPIVQSLAGSR
HGDNRFYFPKEMLDQNSIFASITQQFLHL* (SEQ ID NO:25)

FIGURE 3 - TABLE 2 CONT'D

ID-220B   ATGAACGAAAAAGTATTCCGTGACCCTGTTCACAACTACATCCATGTCAAT
AATCAAATCATCTATGACTTGATTAATMCAMAAGAATTTCAGCGTTTGCGC
CGGATCAAACAACTGGGAACTTCCAGTTATACCTTCCACGGTGGAGAACAC
AGTCGCTTCTCTCACTGTCTAGGAGTCTATGAAATTGCACGACGCATCACA
GAGATTTTCGAAGAAAAATATCCTGAGGAATGGAATCCTGCCGAGTCTCTC
TTGACCATGACCGCTGCTCTCCTACACGACCTTGGGCATGGTGCCTACTCC
CATACTTTTGAACATCTCTTTGATACAGACCATGAAGCCATTACTCAGGAG
ATTATTCAAAATCCTGAGACAGAGATTCACCAAGTCCTGCTACAAGTGGCA
CCTGATTTCCCAGAAAAGGTGGCCAGTGTCATTGACCATACCTATCCTAAT
AAGCAGGTCGTGCAGCTCATTTCTAGTCAGATTGACGCAGATCGCATGGAC
TATCTCTTGCGCGACTCCTATTTTACAGGAGCATCCTATGGGGAATTTGAC
CTGACTCGAATCCTCCGAGTCATTCGTCCTATCGAAAATGGTATCGCCTTT
CAGCGCAATGGCATGCACGCCATCGAAGACTACGTCCTCAGTCGCTACCAG
ATGTACATGCAGGTTTATTTCCACCCCGCAACACGCGCCATGGAAGTTCTC
CTACAGAATCTTCTCAAACGCGCCAAGGAACTCTATCCTGAGGACAAGGAT
TTCTTTGCCCGAACTTCTCCACACCTCCTGCCTTTCTTCGAAAAAAATGTG
ACCTTGACTGACTATCTGGCTCTGGATGATGGCGTGATGAATACCTACTTC
CAGCTTTGGATGACCAGTCCTGACAAGATTCTTGCAGATTTATCGCATCGC
TTTGTCAACCGCAAGGTCTTTAAATCCATTACCTTTTCACAAGAGGACCAA
GATCAACTTACTAGCATGAGAAAATTGGTTGAGGATATCGGCTTTGATCCC
GACTACTACACTGCCATTCATAAGAACTTTGACCTCCCTTATGATATCTAT
CGTCCCGAATCTGAAAACCCACGGACACAGATTGAGATTTTACAAAAAAAT
GGAGAACTGGCCGAACTCTCTAGCCTGTCTCCTATCGTCCAATCCCTTGCT
GGCAGTCGCCACGGAGATAATCGCTTTTATTTTCCAAAAGAAATGTTGGAC
CAAAACAGCATCTTTGCAAGCATTACCCAGCAATTTTTACACTTGA (SEQ ID NO:26)

ID-225A   MNPSLEDINATIATGYSSDTAIKESIDFFQNRTQTFLTNNHAHLEHTTKE
VRC*(SEQ ID NO:27)

ID-225B   ATGAATCCCAGCTTGGAGGATATCAATGCAACCATAGCCACTGGATACAGC
TCGGACACGGCCATCAAAGAGAGCATTGATTTCTTCCAAAACCGAACTCAA
ACGTTCCTCACCAACAACCATGCTCATCTTGAGCACACCACCAAAGAGGTC
AGATGTTAA (SEQ ID NO:28)

ID-301A   MLHLKLVKQEIEAEKPASVEAWIISVKFKKGCYRHI*(SEQ ID NO:29)

ID-301B   ATGCTACACTTAAAATTAGTAAAACAAGAAATAGAAGCTGAAAAGCCAGCA
TCTGTAGAAGCTTGGATCATTTCCGTCAAATTTAAAAAAGGTTGCTACCGA
CATATATAG (SEQ ID NO:30)

ID-304TA  MELVLPNNYVALEQEEMMYLDGGGVGRNWWNSRGSFATVLDVDLAIYSGGA
TIYSAYAIKKAISANRGAITRTLRSLIIKHVGSAAGHLVNTALNVALTVTG
FSLGGAIAYGADWADGSLDGYIFA*(SEQ ID NO:31)

ID-304TB  ATGGAACTCGTATTACCAAATAATTATGTTGCTCTTGAGCAAGAAGAGATG
ATGTATCTTGATGGGGGTGGTGGTGGTCGTAACTGGTGGAATAGTAGAGGT
AGTTTTGCAACAGTTCTGGATGTAGATTTGGCCATCTATAGTGGTGGTGCA
ACAATTTATTCTGCTTATGCGATAAAAAAAGCTATCTCAGCTAATAGAGGG
GCTATTACGAGAACATTACGTAGTTTAATAATTAAACATGTAGGTAGTGCA
GCTGGCCATTTAGTCAATACTGCACTAAACGTTGCACTAACTGTTACTGGA
TTTTCACTAGGTGGAGCAATCGCATATGGGGCTGAGTGGGCTGACGGTAGC
TTAGATGGTTATATTTTTGCTTAA(SEQ ID NO:32)

FIGURE 4 - TABLE 3

ID-304L2A
MELVLPNNYVALEQEEMMYLDGGFSILRWPVATAINIAFNGVLGGGAISLVRNYIRN
YGLGRVTSAIAGAAARYVGVRVANRVAGFALSAINGFAAWMSIGDAITTIWANNDVN
RRDPNLNALW (SEQ ID NO:33)

ID-304L2B
ATGGAACTCGTATTACCAAATAATTATGTTGCTCTTGAGCAAGAAGAGATGATGTAT
CTTGATGGGGGATTTTCTATTCTGAGATGGCCTGTTGCAACAGCCATTAATATAGCT
TTTAATGGTGTTTTAGGTGGAGGAGCAATCAGTCTAGTTAGAAATTATATTCGTAAT
TATGGTTTGGGGCGAGTTACAAGCGCAATTGCTGGAGCAGCTGCAAGATATGTTGGG
GTACGAGTTGCAAATAGAGTGGCAGGATTTGCACTGTCTGCTATTAATGGATTTGCA
GCTTGGATGTCAATTGGCGATGCTATTACAACAATCTGGGCCAACAATGATGTAAAT
AGGAGAGACCCAAATTTAAACGCCTTGTGGTAA (SEQ ID NO:34)

ID-304L3A
MELVLPNNYVVIDEEEMMYLDGGAYLSKRACQGICAALAMSPGTFIALAGAAVLTKK
LINYIKVGGLGGWLIGAAAGVLAGAAGRIAYCIGYGALNRGCDISGNPYPWDGFISA
TVR (SEQ ID NO:35)

ID-304L3B
ATGGAACTTGTATTACCAAATAATTATGTTGTGATTGATGAAGAAGAGATGATGTAC
CTTGATGGGGGAGCTTATTTAAGCAAGCGTGCTTGTCAAGGAATTTGCGCAGCTTTA
GCTATGAGTCCAGGAACTTTTATAGCATTAGCTGGAGCTGCAGTTTTAACCAAAAAA
CTAATAAACTATATTAAAGTTGGAGGCCTTGGAGGTTGGCTTATTGGTGCAGCAGCA
GGTGTATTGGCTGGGGCGGCAGGAAGAATAGCTTACTGTATTGGATATGGTGCTCTT
AATAGAGGTTGTGATATTAGCGGGAACCCTTATCCTTGGGATGGATTCATATCTGCG
ACAGTAAGATGA (SEQ ID NO:36)

ID-304L4A
MELVLPNNYVVIDEEEMMYLDGEAYLSKRACQGICAALAMSSGTFIALAGAAVLTKK
LINYIKVGGLGGWLIGAAAGVLATAAGKIAYYIGYGVLNRGCDINGNPYPWDGFISA
TVR (SEQ ID NO:37)

ID-304L4B
ATGGAACTTGTATTACCAAATAATTATGTTGTGATTGATGAAGAAGAAATGATGTAT
CTTGATGGGGAAGCTTATTTAAGCAAGCGTGCTTGTCAAGGAATTTGCGCAGCTTTA
GCTATGAGTTCAGGCACTTTTATAGCATTAGCTGGAGCTGCAGTTTTAACCAAAAAA
CTAATAAACTATATTAAGGTTGGAGGTCTTGGAGGCTGGCTTATTGGTGCAGCAGCA
GGTGTATTGGCTACAGCAGCAGGGAAAATAGCTTACTATATTGGATATGGTGTTCTT
AATAGAGGTTGTGATATTAACGGGAACCCTTATCCTTGGGATGGATTCATATCTGCG
ACAGTAAGATGAGTAATGTAG (SEQ ID NO:38)

FIGURE 4 - TABLE 3 CONT'D

ID-304L5A
MKQFQLRRRKQMELVLPNNYVVIDEEEMMYLDGGAYLSKRACQGICVALAMSPGIFI
ALAGAAVLTKKLINYIKVGGLGGWLIGAAAGVLATAAGKIAYCIGYGALNRGCDISG
NPYPWDGFISATVR (SEQ ID NO:39)

ID-304L5B
ATGGAACTTGTATTACCAAATAATTATGTTGTGATTGATGAAGAAGAAATGATGTAT
CTTGATGGGGGAGCTTATTTAAGCAAGCGTGCTTGTCAAGGAATTTGCGTAGCTTTA
GCTATGAGTCCAGGAATTTTTATAGCATTAGCTGGAGCTGCAGTTTTAACCAAAAAA
CTAATAAACTATATTAAGGTTGGAGGTCTTGGAGGCTGGCTTATTGGTGCAGCAGCA
GGTGTATTGGCTACAGCAGCAGGAAAAATAGCTTACTGTATTGGATATGGTGCTCTT
AATAGAGGTTGTGATATTAGCGGGAACCCTTATCCTTGGGATGGATTCATATCTGCG
ACAGTAAGATGA (SEQ ID NO:40)

ID-304L6A
MELVLPNNYVVIDEEEMMYLDGGAIYIPRWAITGAITGAAYAALAAAGGGGLQLVLA
SYGLRSALVAGIVKGLGVLGIHIGNAFANTVIRSIASAGIGAGADWIFTNIIDGWDG
RRDNQLRIG (SEQ ID NO:41)

ID-304L6B
ATGGAACTTGTATTACCAAATAATTATGTTGTGATTGATGAAGAAGAGATGATGTAC
CTTGATGGGGGGGCTATATATATACCCAGGTGGGCAATTACAGGAGCCATTACTGGT
GCAGCATATGCAGCATTAGCAGCAGCAGGAGGTGGAGGCCTTCAACTAGTTCTTGCA
TCTTATGGATTACGCTCCGCACTGGTAGCTGGGATTGTTAAAGGTTTAGGAGTATTA
GGAATTCATATTGGAAATGCTTTTGCAAATACTGTTATTAGAAGTATTGCATCTGCT
GGAATTGGTGCTGGAGCTGATTGGATTTTTACCAATATTATTGATGGCTGGGATGGG
CGACGTGATAATCAATTGAGAATAGGTTAA (SEQ ID NO:42)

ID-304L7A
MELVLPNNYVDLEQEEMMYLDGGGVGRNWWNSRGSFATVLDVGLAIYSGGATIYSAY
AIKKAISANRGAITRTLRSLIIKHVGSAAGHLVNTALNVALTVTGFSLGGAIAYGAD
WADGSLDGYIFA (SEQ ID NO:43)

ID-304L7B
ATGGAACTCGTATTACCAAATAATTATGTTGATCTTGAGCAAGAAGAGATGATGTAT
CTTGATGGGGGTGGTGTTGGTCGTAACTGGTGGAATAGTAGAGGTAGTTTTGCAACA
GTTCTGGATGTAGGTTTGGCCATCTATAGTGGTGGTGCAACAATTTATTCTGCTTAT
GCGATAAAAAAAGCTATCTCAGCTAATAGAGGGGCTATTACGAGAACATTACGTAGT
TTAATAATTAAACATGTAGGTAGTGCAGCTGGCCATTTAGTCAATACTGCACTAAAC
GTTGCACTAACTGTTACTGGATTTTCACTAGGTGGAGCAATCGCATATGGGGCTGAT
TGGGCTGACGGTAGCTTAGATGGTTATATTTTTGCTTAA (SEQ ID NO:44)

SECRETED *STREPTOCOCCUS PNEUMONIAE* PROTEINS

FIELD OF THE INVENTION

The present invention relates to proteins derived from *Streptococcus pneumoniae*, nucleic acid molecules encoding such proteins, the use of the nucleic acid and/or proteins as antigens/immunogens and in detection/diagnosis, as well as methods for screening the proteins/nucleic acid sequences as potential anti-microbial targets.

BACKGROUND OF THE INVENTION

*Streptococcus pneumoniae*, commonly referred to as the pneumococcus, is an important pathogenic organism. The continuing significance of *Streptococcus pneumoniae* infections in relation to human disease in developing and developed countries has been authoritatively reviewed (Fiber, G. R., *Science*, 265:1385-1387 (1994)). That indicates that on a global scale this organism is believed to be the most common bacterial cause of acute respiratory infections, and is estimated to result in one million childhood deaths each year, mostly in developing countries (Stansfield, S. K., *Pediatr. Infect. Dis.*, 6:622 (1987)). In the USA it has been suggested (Breiman et al, *Arch. Intern. Med.*, 150:1401 (1990)) that the pneumococcus is still the most common cause of bacterial pneumonia, and that disease rates are particularly high in young children, in the elderly, and in patients with predisposing conditions such as asplenia, heart, lung and kidney disease, diabetes, alcoholism, or with immunosupressive disorders, especially AIDS. These groups are at higher risk of pneumococcal septicaemia and hence meningitis and therefore have a greater risk of dying from pneumococcal infection. Over 50,000 cases of invasive pneumococcal disease (meningitis and bacteraemia) are believed to occur annually in the United States. The pneumococcus is also the leading cause of otitis media and sinusitis, which remain prevalent infections in children in developed countries, and which incur substantial costs. *S. pneumoniae* is responsible for approximately seven million cases of middle ear infections in children under two years of age in the United States alone.

The need for effective preventative strategies against pneumococcal infection is highlighted by the recent emergence of penicillin-resistant pneumococci. It has been reported that 6.6% of pneumoccal isolates in 13 US hospitals in 12 states were found to be resistant to penicillin and some isolates were also resistant to other antibiotics including third generation cyclosporins (Schappert, S. M., *Vital and Health Statistics of the Centres for Disease Control/National Centre for Health Statistics*, 214:1 (1992)). The rates of penicillin resistance can be higher (up to 20%) in some hospitals (Breiman et al, *J. Am. Med. Assoc.*, 271:1831 (1994)). Since the development of penicillin resistance among pneumococci is both recent and sudden, coming after decades during which penicillin remained an effective treatment, these findings are regarded as alarming.

For the reasons given above, there are therefore compelling grounds for considering improvements in the means of preventing, controlling, diagnosing or treating pneumococcal diseases.

Various approaches have been taken in order to provide vaccines for the prevention of pneumococcal infections. Difficulties arise for instance in view of the variety of serotypes (at least 90) based on the structure of the polysaccharide capsule surrounding the organism. Vaccines against individual serotypes are not effective against other serotypes and this means that vaccines must include polysaccharide antigens from a whole range of serotypes in order to be effective in a majority of cases. An additional problem arises because it has been found that the capsular polysaccharides (each of which determines the serotype and is the major protective antigen) when purified and used as a vaccine do not reliably induce protective antibody responses in children under two years of age, the age group which suffers the highest incidence of invasive pneumococcal infection and meningitis.

A modification of the approach using capsule antigens relies on conjugating the polysaccharide to a protein in order to derive an enhanced immune response, particularly by giving the response T-cell dependent characteristics. This approach has been used in the development of a vaccine against *Haemophilus influenzae*, for instance. There are, however, issues of cost concerning both the multi-polysaccharide vaccines and those based on conjugates. In addition, the composition of the conjugate vaccines preferably requires to be varied to accommodate different geographical and demographical populations as the serotype coverage that they offer is limited. There may also be problems with conjugate carrier-induced suppression or overload due to the relatively large total dose of carrier protein administered.

A third approach is to look for other antigenic components which offer the potential to be vaccine candidates. This is the basis of the present invention. Using a specially developed bacterial expression system, we have been able to identify a group of protein antigens from pneomococcus which are associated with the bacterial envelope or which are secreted.

BRIEF DESCRIPTION OF THE DRAWINGS

FIG. 1: Conservation of the ID304L1 gene across a range of serotypes. Genomic DNA from each strain was digested completely with Hind III (Roche) and electrophoresed at 12 volts for 20 hours in 1.0% agarose, transferred onto HYBOND™ N+ (Amersham) membrane by Southern blot and hybridised with the digoxigenin-labelled LID-304 gene probe. Specifically bound DNA probe was identified using the DIG Nucleic Acid Detection Kit (Boehringer Mannheim). Lane 1: *S. pneumoniae* serotype 5 clinical isolate; Lane 2: *S. pneumoniae* serotype 18C clinical isolate; Lane 3: *S. pneumoniae* serotype 23F clinical isolate; Lane 4: *S. pneumoniae* serotype 7F clinical isolate; Lane 5: *S. pneumoniae* serotype 1 clinical isolate; Lane 6: *S. pneumoniae* serotype 6B clinical isolate; Lane 7 :*S. pneumoniae* serotype 4 clinical isolate; Lane 8: *S. pneumoniae* serotype 3 clinical isolate; Lane 9: *S. pneumoniae* serotype 19F clinical isolate; Lane 10: *S. pneumoniae* serotype 9V clinical isolate; Lane 11: *S. pneumoniae* serotype 14 clinical isolate; Lane 12: *S. pneumoniae* strain ATCC 49619 (serotype 3); Lane 13: *Moraxella catarrhalis* DNA; Lane 14: DIG-labelled markers λHindIII; Lane 15: LID304L1 gene from ATCC49615.

FIG. 2: The sequences of Table 1: The sequences are ID-303A, ID-303B, ID-305A, ID-305B, ID-306A, ID-306B, ID-304L1A and ID304L1B.

FIG. 3: The sequences of Table 2. Bracketed residues represent an alternative to the residue immediately preceeding. IUPAC nucleic acid ambiguity codes have been amplied. The sequences are: 1D-204A, 1D-204B, 1D-212A, 1D-212B, 1D-213A, 1D-213B, 1D-214A, 1D-214B, 1D-215A, 1D-215B, 1D-216A, 1D-216B, 1D-217A, 1D-217B, 1D-219A, 1D-219B, 1D-220A, 10-220B, 1D-225A, 10-225B, 1D-301A, 10-301B, 10-304TA and 1D-304TB.

FIG. 4: The sequences of Table 3. The sequences are: 1D-304L2A, ID-304L2B, ID-304L3A, ID-304L3B, ID-304L4A, ID-304L4B, ID-304L5A, ID-304L5B, ID-304L6A, ID-304L6B, ID-304L7A and ID-304L7B.

DETAILED DESCRIPTION OF THE INVENTION

Thus, in a first aspect the present invention provides a *Streptococcus pneumoniae* protein or polypeptide having a sequence selected from those shown in Table 1.

A protein or polypeptide of the present invention may be provided in substantially pure form. For example, it may be provided in a form which is substantially free of other proteins.

As discussed herein, the proteins and polypeptides of the invention are useful as antigenic material. Such material can be "antigenic" and/or "immunogenic". Generally, "antigenic" is taken to mean that the protein or polypeptide is capable of being used to raise antibodies or indeed is capable of inducing an antibody response in a subject. "Immunogenic" is taken to mean that the protein or polypeptide is capable of eliciting a protective immune response in a subject. Thus, in the latter case, the protein or polypeptide may be capable of not only generating an antibody response but, in addition, a non-antibody based immune response.

The skilled person will appreciate that homologues or derivatives of the proteins or polypeptides of the invention will also find use in the context of the present invention, ie as antigenic/immunogenic material. Thus, for instance proteins or polypeptides which include one or more additions, deletions, substitutions or the like are encompassed by the present invention. In addition, it may be possible to replace one amino acid with another of similar "type". For instance replacing one hydrophobic amino acid with another.

One can use a program such as the CLUSTAL™ program to compare amino acid sequences. This program compares amino acid sequences and finds the optimal alignment by inserting spaces in either sequence as appropriate. It is possible to calculate amino acid identity or similarity (identity plus conservation of amino acid type) for an optimal alignment. A program like BLASTx will align the longest stretch of similar sequences and assign a value to the fit. It is thus possible to obtain a comparison where several regions of similarity are found, each having a different score. Both types of identity analysis are contemplated in the present invention.

In the case of homologues and derivatives, the degree of identity with a protein or polypeptide as described herein is less important than that the homologue or derivative should retain the antigenicity or immunogenicity of the original protein or polypeptide. However, suitably, homologues or derivatives having at least 60% similarity (as discussed above) with the proteins or polypeptides described herein are provided. Preferably, homologues or derivatives having at least 70% similarity, more preferably at least 80% similarity are provided. Most preferably, homologues or derivatives having at least 90% or even 95% similarity are provided.

In an alternative approach, the homologues or derivatives could be fusion proteins, incorporating moieties which render purification easier, for example by effectively tagging the desired protein or polypeptide. It may be necessary to remove the "tag" or it may be the case that the fusion protein itself retains sufficient antigenicity to be useful.

In an additional aspect of the invention there are provided antigenic/immunogenic fragments of the proteins or polypeptides of the invention, or of homologues or derivatives thereof.

For fragments of the proteins or polypeptides described herein, or of homologues or derivatives thereof, the situation is slightly different. It is well known that is possible to screen an antigenic protein or polypeptide to identify epitopic regions, ie those regions which are responsible for the protein or polypeptide's antigenicity or immunogenicity. Methods for carrying out such screening are well known in the art. Thus, the fragments of the present invention should include one or more such epitopic regions or be sufficiently similar to such regions to retain their antigenic/immunogenic properties. Thus, for fragments according to the present invention the degree of identity is perhaps irrelevant, since they may be 100% identical to a particular part of a protein or polypeptide, homologue or derivative as described herein. The key issue, once again, is that the fragment retains the antigenic/immunogenic properties.

Thus, what is important for homologues, derivatives and fragments is that they possess at least a degree of the antigenicity/immunogenicity of the protein or polypeptide from which they are derived.

Gene cloning techniques may be used to provide a protein of the invention in substantially pure form. These techniques are disclosed, for example, in J. Sambrook et al *Molecular Cloning* 2nd Edition, Cold Spring Harbor Laboratory Press (1989). Thus, in a second aspect, the present invention provides a nucleic acid molecule comprising or consisting of a sequence which is:

(i) any of the DNA sequences set out in Table 1 or their RNA equivalents;

(ii) a sequence which is complementary to any of the sequences of (i);

(iii) a sequence which codes for the same protein or polypeptide, as those sequences of (i) or (ii);

(iv) a sequence which has substantial identity with any of those of (i), (ii) and (iii);

(v) a sequence which codes for a homologue, derivative or fragment of a protein as defined in Table 1.

The nucleic acid molecules of the invention may include a plurality of such sequences, and/or fragments. The skilled person will appreciate that the present invention can include novel variants of those particular novel nucleic acid molecules which are exemplified herein. Such variants are encompassed by the present invention. These may occur in nature, for example because of strain variation. For example, additions, substitutions and/or deletions are included. In addition, and particularly when utilising microbial expression systems, one may wish to engineer the nucleic acid sequence by making use of known preferred codon usage in the particular organism being used for expression. Thus, synthetic or non-naturally occurring variants are also included within the scope of the invention.

The term "RNA equivalent" when used above indicates that a given RNA molecule has a sequence which is complementary to that of a given DNA molecule (allowing for the fact that in RNA "U" replaces "T" in the genetic code).

When comparing nucleic acid sequences for the purposes of determining the degree of homology or identity one can use programs such as BESTFIT and GAP (both from the Wisconsin Genetics Computer Group (GCG) software package) BESTFIT, for example, compares two sequences and produces an optimal alignment of the most similar segments. GAP enables sequences to be aligned along their whole length and finds the optimal alignment by inserting spaces in either sequence as appropriate. Suitably, in the context of the present invention when discussing identity of nucleic acid sequences, the comparison is made by alignment of the sequences along their whole length.

Preferably, sequences which have substantial identity have at least 50% sequence identity, desirably at least 75% sequence identity and more desirably at least 90 or at least 95% sequence identity with said sequences. In some cases the sequence identity may be 99% or above.

Desirably, the term "substantial identity" indicates that said sequence has a greater degree of identity with any of the sequences described herein than with prior art nucleic acid sequences.

It should however be noted that where a nucleic acid sequence of the present invention codes for at least part of a novel gene product the present invention includes within its scope all possible sequence coding for the gene product or for a novel part thereof.

The nucleic acid molecule may be in isolated or recombinant form. It may be incorporated into a vector and the vector may be incorporated into a host. Such vectors and suitable hosts form yet further aspects of the present invention.

Therefore, for example, by using probes based upon the nucleic acid sequences provided herein, genes in *Streptococcus pneumoniae* can be identified. They can then be excised using restriction enzymes and cloned into a vector. The vector can be introduced into a suitable host for expression.

Nucleic acid molecules of the present invention may be obtained from *S. pneumoniae* by the use of appropriate probes complementary to part of the sequences of the nucleic acid molecules. Restriction enzymes or sonication techniques can be used to obtain appropriately sized fragments for probing.

Alternatively PCR techniques may be used to amplify a desired nucleic acid sequence. Thus the sequence data provided herein can be used to design two primers for use in PCR so that a desired sequence, including whole genes or fragments thereof, can be targeted and then amplified to a high degree.

Typically primers will be at least 15-25 nucleotides long.

As a further alternative chemical synthesis may be used. This may be automated. Relatively short sequences may be chemically synthesised and ligated together to provide a longer sequence.

There is another group of proteins from *S. pneumoniae* which have been identified using the bacterial expression system described herein. These are known proteins from *S. pneumoniae*, which have not previously been identified as antigenic proteins. The amino acid sequences of this group of proteins, together with DNA sequences coding for them are shown in Table 2. These proteins, or homologues, derivatives and/or fragments thereof also find use as antigens/immunogens.

A further group of proteins have been identified from recently published *S. pnuemoniae* genomes that have a degree of homology with ID-304L1 which all possess the following highly conserved sequence of 23 amino acids either at or near the N-terminus:

MELVLPNNYVV(D,A)I(L)D(E)E(Q)EEMMYLDGG (E) (SEQ ID NO:45) where the bracketed residues represent alternatives to the preceding amino acid. Amino acid sequences for these homologues, and the DNA sequences encoding them are given in Table 3.

Thus, in a further aspect the present invention provides a *Streptococcus pneumoniae* protein which has the N terminal sequence MELVLPNNYVV(D,A)I(L)D(E)E(Q)EEMMYLDGG (E) (SEQ ID NO:45) or fragment or homologue or derivative thereof.

In another aspect the present invention provides the use of a protein or polypeptide having a sequence selected from those shown in Tables 1 to 3, or homologues, derivatives and/or fragments thereof, as an immunogen/antigen.

In yet a further aspect the present invention provides an immunogenic/antigenic composition comprising one or more proteins or polypeptides selected from those whose sequences are shown in Tables 1 to 3, or homologues or derivatives thereof, and/or fragments of any of these. In preferred embodiments, the immunogenic/antigenic composition is a vaccine or is for use in a diagnostic assay.

In the case of vaccines, suitable additional excipients, diluents, adjuvants or the like may be included. Numerous examples of these are well known in the art.

It is also possible to utilise the nucleic acid sequences shown in Tables 1 and 2 in the preparation of so-called DNA vaccines. Thus, the invention also provides a vaccine composition comprising one or more nucleic acid sequences as defined herein. DNA vaccines are described in the art (see for instance, Donnelly et al, *Ann. Rev. Immunol.*, 15:617-648 (1997)) and the skilled person can use such art described techniques to produce and use DNA vaccines according to the present invention.

As already discussed herein the proteins or polypeptides described herein, their homologues or derivatives, and/or fragments of any of these, can be used in methods of detecting/diagnosing *S. pneumoniae*. Such methods can be based on the detection of antibodies against such proteins which may be present in a subject. Therefore the present invention provides a method for the detection/diagnosis of *S. pneumoniae* which comprises the step of bringing into contact a sample to be tested with at least one protein, or homologue, derivative or fragment thereof, as described herein. Suitably, the sample is a biological sample, such as a tissue sample or a sample of blood or saliva obtained from a subject to be tested.

In an alternative approach, the proteins described herein, or homologues, derivatives and/or fragments thereof, can be used to raise antibodies, which in turn can be used to detect the antigens, and hence *S. pneumoniae*. Such antibodies form another aspect of the invention. Antibodies within the scope of the present invention may be monoclonal or polyclonal.

Polyclonal antibodies can be raised by stimulating their production in a suitable animal host (e.g. a mouse, rat, guinea pig, rabbit, sheep, goat or monkey) when a protein as described herein, or a homologue, derivative or fragment thereof, is injected into the animal. If desired, an adjuvant may be administered together with the protein. Well-known adjuvants include Freund's adjuvant (complete and incomplete) and aluminium hydroxide. The antibodies can then be purified by virtue of their binding to a protein as described herein.

Monoclonal antibodies can be produced from hybridomas. These can be formed by fusing myeloma cells and spleen cells which produce the desired antibody in order to form an immortal cell line. Thus the well-known Kohler & Milstein technique (*Nature* 256 (1975)) or subsequent variations upon this technique can be used.

Techniques for producing monoclonal and polyclonal antibodies that bind to a particular polypeptide/protein are now well developed in the art. They are discussed in standard immunology textbooks, for example in Roitt et al, *Immunology* second edition (1989), Churchill Livingstone, London.

In addition to whole antibodies, the present invention includes derivatives thereof which are capable of binding to proteins etc as described herein. Thus the present invention includes antibody fragments and synthetic constructs. Examples of antibody fragments and synthetic constructs are given by Dougall et al in *Tibtec*, 12:372-379 (September 1994).

Antibody fragments include, for example, Fab, F(ab')$_2$ and Fv fragments. Fab fragments are discussed in Roitt et al [supra]. Fv fragments can be modified to produce a synthetic construct known as a single chain Fv (scFv) molecule. This includes a peptide linker covalently joining $V_h$ and $V_l$ regions, which contributes to the stability of the molecule. Other synthetic constructs that can be used include Complementarity Determining Regions (CDR) peptides. These are synthetic peptides comprising antigen-binding determinants. Peptide mimetics may also be used. These molecules are usually conformationally restricted organic rings that mimic the structure of a CDR loop and that include antigen-interactive side chains.

Synthetic constructs include chimaeric molecules. Thus, for example, humanised (or primatised) antibodies or derivatives thereof are within the scope of the present invention. An example of a humanised antibody is an antibody having human framework regions, but rodent hypervariable regions. Ways of producing chimaeric antibodies are discussed for example by Morrison et al in PNAS, 81:6851-6855 (1984) and by Takeda et al in Nature. 314:452-454 (1985).

Synthetic constructs also include molecules comprising an additional moiety that provides the molecule with some desirable property in addition to antigen binding. For example the moiety may be a label (e.g. a fluorescent or radioactive label). Alternatively, it may be a pharmaceutically active agent.

Antibodies, or derivatives thereof, find use in detection/diagnosis of S. pneumoniae. Thus, in another aspect the present invention provides a method for the detection/diagnosis of S. pneumoniae which comprises the step of bringing into contact a sample to be tested and antibodies capable of binding to one or more proteins described herein, or to homologues, derivatives and/or fragments thereof.

In addition, so-called "Affibodies" may be utilised. These are binding proteins selected from combinatorial libraries of an alpha-helical bacterial receptor domain (Nord et al in Nature Biotechnology, 15:772-7 (1997)). Thus, small protein domains, capable of specific binding to different target proteins can be selected using combinatorial approaches.

It will also be clear that the nucleic acid sequences described herein may be used to detect/diagnose S. pneumoniae. Thus, in yet a further aspect, the present invention provides a method for the detection/diagnosis of S. pneumoniae which comprises the step of bringing into contact a sample to be tested with at least one nucleic acid sequence as described herein. Suitably, the sample is a biological sample, such as a tissue sample or a sample of blood or saliva obtained from a subject to be tested. Such samples may be pre-treated before being used in the methods of the invention. Thus, for example, a sample may be treated to extract DNA. Then, DNA probes based on the nucleic acid sequences described herein (ie usually fragments of such sequences) may be used to detect nucleic acid from S. pneumoniae.

In additional aspects, the present invention provides:

(a) a method of vaccinating a subject against S. pneumoniae which comprises the step of administering to a subject a protein or polypeptide of the invention, or a derivative, homologue or fragment thereof, or an immunogenic composition of the invention;

(b) a method of vaccinating a subject against S. pneumoniae which comprises the step of administering to a subject a nucleic acid molecule as defined herein;

(c) a method for the prophylaxis or treatment of S. pneumoniae infection which comprises the step of administering to a subject a protein or polypeptide of the invention, or a derivative, homologue or fragment thereof, or an immunogenic composition of the invention;

(d) a method for the prophylaxis or treatment of S. pneumoniae infection which comprises the step of administering to a subject a nucleic acid molecule as defined herein;

(e) a kit for use in detecting/diagnosing S. pneumoniae infection comprising one or more proteins or polypeptides of the invention, or homologues, derivatives or fragments thereof, or an antigenic composition of the invention; and (f) a kit for use in detecting/diagnosing S. pneumoniae infection comprising one or more nucleic acid molecules as defined herein.

Given that we have identified a group of important proteins, such proteins are potential targets for anti-microbial therapy. It is necessary, however, to determine whether each individual protein is essential for the organism's viability. Thus, the present invention also provides a method of determining whether a protein or polypeptide as described herein represents a potential anti-microbial target which comprises antagonising, inhibiting or otherwise interfering with the function or expression of said protein and determining whether S. pneumoniae is still viable.

A suitable method for inactivating the protein is to effect selected gene knockouts, ie prevent expression of the protein and determine whether this results in a lethal change. Suitable methods for carrying out such gene knockouts are described in Li et al, P.N.A.S., 94:13251-13256 (1997) and Kolkman et al, J. Bacteriol., 178:3736-3741 (1996).

In a final aspect the present invention provides the use of an agent capable of antagonising, inhibiting or otherwise interfering with the function or expression of a protein or polypeptide of the invention in the manufacture of a medicament for use in the treatment or prophylaxis of S. pneumoniae infection.

As mentioned above, we have used a bacterial expression system as a means of identifying those proteins which are surface associated, secreted or exported and thus, would find use as antigens or antimicrobial targets.

The information necessary for the secretion/export of proteins has been extensively studied in bacteria. In the majority of cases, protein export requires a signal peptide to be present at the N-terminus of the precursor protein so that it becomes directed to the translocation machinery on the cytoplasmic membrane. During or after translocation, the signal peptide is removed by a membrane associated signal peptidase. Ultimately the localization of the protein (i.e. whether it be secreted, an integral membrane protein or attached to the cell wall) is determined by sequences other than the leader peptide itself.

We are specifically interested in surface located or exported proteins as these are likely to be antigens for use in vaccines, as diagnostic reagents or as targets for therapy with novel chemical entities. We have therefore developed a screening vector-system in Lactococcus lactis that permits genes encoding exported proteins to be identified and isolated. We provide below a representative example showing how given novel surface associated proteins from Streptococcus pneumoniae have been identified and characterized. The screening vector incorporates the staphylococcal nuclease gene nuc lacking its own export signal as a secretion reporter. Staphylococcal nuclease is a naturally secreted heat-stable, monomeric enzyme which has been efficiently expressed and secreted in a range of Gram positive bacteria (Shortle, Gene, 22:181-189 (1983); Kovacevic et al., J. Bacteriol., 162:521-528 (1985); Miller et al., J. Bacteriol., 169:3508-3514 (1987); Liebl et al., J. Bacteriol., 174:1854-1861 (1992); Le Loir et al., J. Bacteriol., 176:5135-5139 (1994); Poquet et al., J. Bacteriol., 180:1904-1912 (1998)).

Recently, Poquet et al. ((1998), supra) have described a screening vector incorporating the nuc gene lacking its own signal leader as a reporter to identify exported proteins in Gram positive bacteria, and have applied it to L. lactis. This vector (PFUN) contains the PAMβ1 replicon which functions in a broad host range of Gram-positive bacteria in addition to the ColE1 replicon that promotes replication in *Escherichia coli* and certain other Gram negative bacteria. Unique cloning sites present in the vector can be used to generate transcriptional and translational fusions between cloned genomic DNA fragments and the open reading frame of the truncated nuc gene devoid of its own signal secretion leader. The nuc gene makes an ideal reporter gene because the secretion of nuclease can readily be detected using a simple and sensitive plate test; recombinant colonies secreting the nuclease develop a pink halo whereas control colonies remain white (Shortle, (1983), supra; Le Loir et al., (1994), supra).

Thus, the invention will now be described with reference to the following representative example, which provides details of how the proteins, polypeptides and nucleic acid sequences described herein identified as antigenic targets.

We describe herein the construction of three reporter vectors and their use in *L. lactis* to identify and isolate genomic DNA fragments from *Streptococcus pneumoniae* encoding secreted or surface associated proteins. Furthermore, Southern blot hybridisation experiments have been conducted to demonstrate the presence of a vaccine candidate gene in a range of *Streptococcus pneumoniae* strains. The invention will now be described with reference to the examples, which should not be construed as in any way limiting the invention.

EXAMPLES

Example 1

(i) Construction of the pTREP1-nuc Series of Reporter Vectors
(a) Construction of Expression Plasmid pTREP1

The pTREPI plasmid is a high-copy number (40-80 per cell) theta-replicating gram positive plasmid, which is a derivative of the pTREX plasmid which is itself a derivative of the previously published pIL253 plasmid. pIL253 incorporates the broad Gram-positive host range replicon of pAMβ1 (Simon and Chopin, *Biochimie,* 70:559-567 (1988)) and is non-mobilisable by the *L. lactis* sex-factor. pIL253 also lacks the tra function which is necessary for transfer or efficient mobilisation by conjugative parent plasmids exemplified by pIL501. The Enterococcal pAMβ1 replicon has previously been transferred to various species including *Streptococcus, Lactobacillus* and *Bacillus* species as well as *Clostridium acetobutylicum*, (Oultram and Klaenhammer, *FEMS Microbiological Letters,* 27:129-134 (1985); Gibson et al., (1979); LeBlanc et al., *Proceedings of the National Academy of Science USA,* 75:3484-3487 (1978)) indicating the potential broad host range utility. The pTREP1 plasmid represents a constitutive transcription vector.

The pTREX vector was constructed as follows. An artificial DNA fragment containing a putative RNA stabilising sequence, a translation initiation region (TIR), a multiple cloning site for insertion of the target genes and a transcription terminator was created by annealing two complementary oligonucleotides and extending with Tfl DNA polymerase. The sense and anti-sense oligonucleotides contained the recognition sites for NheI and BamHI at their 5' ends respectively to facilitate cloning. This fragment was cloned between the XbaI and BamHI sites in pUC19NT7, a derivative of pUC19 which contains the T7 expression cassette from pLET1 (Wells et al, *J. Appl. Bacteriol.,* 74:629-636 (1993)) cloned between the EcoRI and HindIII sites. The resulting construct was designated pUCLEX. The complete expression cassette of pUCLEX was then removed by cutting with Hin-dIII and blunting followed by cutting with EcoRI before cloning into EcoRI and SacI (blunted) sites of pIL253 to generate the vector pTREX (Wells and Schofield, In *Current advances in metabolism, genetics and applications-NATO ASI Series,* H 98:37-62 (1996)). The putative RNA stabilising sequence and TIR are derived from the *Escherichia coli* T7 bacteriophage sequence and modified at one nucleotide position to enhance the complementarity of the Shine Dalgarno (SD) motif to the ribosomal 16s RNA of *Lactococcus lactis* (Schofield et al. pers. coms. University of Cambridge Dept. Pathology).

A *Lactococcus lactis* MG1363 chromosomal DNA fragment exhibiting promoter activity which was subsequently designated P7 was cloned between the EcoRI and BglII sites present in the expression cassette, creating pTREX7. This active promoter region had been previously isolated using the promoter probe vector pSB292 (Waterfield et al, Gene, 165: 9-15 (1995)). The promoter fragment was amplified by PCR using the Vent DNA polymerase according to the manufacturer.

The pTREPI vector was then constructed as follows. An artificial DNA fragment which included a transcription terminator, the forward pUC sequencing primer, a promoter multiple-cloning site region and a universal translation stop sequence was created by annealing two overlapping partially complementary synthetic oligonucleotides together and extending with sequenase according to the manufacturer's instructions. The sense and anti-sense (pTREP$_F$ and pTREP$_R$) oligonucleotides contained the recognition sites for EcoRV and BamHI at their 5' ends respectively to facilitate cloning into pTREX7. The transcription terminator was that of the *Bacillus penicillinase* gene, which has been shown to be effective in *Lactococcus* (Jos et al., *Applied and Environmental Microbiology,* 50:540-542 (1985)). This was considered necessary as expression of target genes in the pTREX vectors was observed to be leaky and is thought to be the result of cryptic promoter activity in the origin region (Schofield et al. pers. coms. University of Cambridge Dept. Pathology). The forward pUC primer sequencing was included to enable direct sequencing of cloned DNA fragments. The translation stop sequence which encodes a stop codon in 3 different frames was included to prevent translational fusions between vector genes and cloned DNA fragments. The pTREX7 vector was first digested with EcoRI and blunted using the 5'-3' polymerase activity of T4 DNA polymerase (NEB) according to manufacturer's instructions. The EcoRI digested and blunt ended pTREX7 vector was then digested with Bgl II thus removing the P7 promoter. The artificial DNA fragment derived from the annealed synthetic oligonucleotides was then digested with EcoRV and Bam HI and cloned into the EcoRI (blunted)-Bgl II digested pTREX7 vector to generate pTREP. A *Lactococcus lactis* MG1363 chromosomal promoter designated P1 was then cloned between the EcoRI and BglII sites present in the pTREP expression cassette forming pTREP1. This promoter was also isolated using the promoter probe vector pSB292 and characterised by Waterfield et al., (1995), supra. The P1 promoter fragment was originally amplified by PCR using VENT® DNA polymerase according to the manufacturer's instructions and cloned into the pTREX as an EcoRI-BglII DNA fragment. The EcoRI-BglII P1 promoter containing fragment was removed from pTREX1 by restriction enzyme digestion and used for cloning into pTREP (Schofield et al. pers. coms. University of Cambridge, Dept. Pathology).

(b) PCR Amplification of the *S. aureus* nuc Gene.

The nucleotide sequence of the *S. aureus* nuc gene (EMBL database accession number V01281) was used to design synthetic oligonucleotide primers for PCR amplification. The primers were designed to amplify the mature form of the nuc gene designated nucA which is generated by proteolytic cleavage of the N-terminal 19 to 21 amino acids of the secreted propeptide designated Snase B (Shortle, (1983), supra). Three sense primers (nucS1, nucS2 and nucS3, Appendix 1) were designed, each one having a blunt-ended restriction endonuclease cleavage site for EcoRV or SmaI in a different reading frame with respect to the nuc gene. Additionally BglII and BamHI were incorporated at the 5' ends of the sense and anti-sense primers respectively to facilitate cloning into BamHI and BglII cut pTREP1. The sequences of all the primers are given in Appendix 1. Three nuc gene DNA fragments encoding the mature form of the nuclease gene (NucA) were amplified by PCR using each of the sense primers combined with the anti-sense primer described above. The nuc gene fragments were amplified by PCR using S. aureus genomic DNA template, VENT® DNA Polymerase (NEB) and the conditions recommended by the manufacturer. An initial denaturation step at 93° C. for 2 min was followed by 30 cycles of denaturation at 93° C. for 45 sec, annealing at 50° C. for 45 seconds, and extension at 73° C. for 1 minute and then a final 5 min extension step at 73° C. The PCR amplified products were purified using a Wizard® clean up column (Promega) to remove unincorporated nucleotides and primers.

(c) Construction of the pTREPI -nuc Vectors

The purified nuc gene fragments described in section (b) were digested with Bgl II and BamHI using standard conditions and ligated to BamHI and BglII cut and dephosphorylated pTREPI to generate the pTREP1-nuc1, pTREPI-nuc2 and pTREP1-nuc3 series of reporter vectors. General molecular biology techniques were carried out using the reagents and buffer supplied by the manufacturer or using standard conditions (Sambrook and Maniatis, (1989), supra). In each of the pTREP1-nuc vectors the expression cassette comprises a transcription terminator, lactococcal promoter P1, unique cloning sites (BglII, EcoRV or SmaI) followed by the mature form of the nuc gene and a second transcription terminator. Note that the sequences required for translation and secretion of the nuc gene were deliberately excluded in this construction. Such elements can only be provided by appropriately digested foreign DNA fragments (representing the target bacterium) which can be cloned into the unique restriction sites present immediately upstream of the nuc gene.

In possessing a promoter, the pTREPI-nuc vectors differ from the pFUN vector described by Poquet et al. (1998), supra, which was used to identify L. lactis exported proteins by screening directly for Nuc activity directly in L. lactis. As the pFUN vector does not contain a promoter upstream of the nuc open reading frame the cloned genomic DNA fragment must also provide the signals for transcription in addition to those elements required for translation initiation and secretion of Nuc. This limitation may prevent the isolation of genes that are distant from a promoter, for example genes which are within polycistronic operons. Additionally there can be no guarantee that promoters derived from other species of bacteria will be recognised and functional in L. lactis. Certain promoters may be under stringent regulation in the natural host but not in L. lactis. In contrast, the presence of the P1 promoter in the pTREP1-nuc series of vectors ensures that promoterless DNA fragments (or DNA fragments containing promoter sequences not active in L. lactis) will still be transcribed.

(ii) Screening for S. pneumoniae Secreted Proteins

Genomic DNA isolated from S. pneumoniae was digested with the restriction enzyme Tru9I. This enzyme which recognises the sequence 5'-TTAA-3' was used because it cuts A/T rich genomes efficiently and can generate random genomic DNA fragments within the preferred size range (usually averaging 0.5-1.0 kb). This size range was preferred because there is an increased probability that the P1 promoter can be utilised to transcribe a novel gene sequence. However, the P1 promoter may not be necessary in all cases as it is possible that many Streptococcal promoters are recognised in L. lactis. DNA fragments of different size ranges were purified from partial Tru9I digests of S. pneumoniae genomic DNA. As the Tru9I restriction enzyme generates staggered ends the DNA fragments had to be made blunt ended before ligation to the EcoRV or SmaI cut pTREP1-nuc vectors. This was achieved by the partial fill-in enzyme reaction using the 5'-3' polymerase activity of Klenow enzyme. Briefly Tru9I digested DNA was dissolved in a solution (usually between 10-20 μl in total) supplemented with T4 DNA ligase buffer (New England Biolabs; NEB) (1×) and 33 μM of each of the required dNTPs, in this case dATP and dTTP. Klenow enzyme was added (1 unit Klenow enzyme (NEB) per μg of DNA) and the reaction incubated at 25° C. for 15 minutes. The reaction was stopped by incubating the mix at 75° C. for 20 minutes. EcoRV or SmaI digested pTREP-nuc plasmid DNA was then added (usually between 200-400 ng). The mix was then supplemented with 400 units of T4 DNA ligase (NEB) and T4 DNA ligase buffer (1×) and incubated overnight at 16° C. The ligation mix was precipitated directly in 100% Ethanol and 1/10 volume of 3M sodium acetate (pH 5.2) and used to transform L. lactis MG1363 (Gasson, 1983). Alternatively, the gene cloning site of the pTREP-nuc vectors also contains a BglII site which can be used to clone for example Sau3AI digested genomic DNA fragments.

L. lactis transformant colonies were grown on brain heart infusion agar and nuclease secreting (Nuc+) clones were detected by a toluidine blue-DNA-agar overlay (0.05 M Tris pH 9.0, 10 g of agar per liter, 10 g of NaCl per liter, 0.1 mM $CaCl_2$, 0.03% wt/vol. salmon sperm DNA and 90 mg of Toluidine blue O dye) essentially as described by Shortle, 1983, supra and Le Loir et al., 1994, supra). The plates were then incubated at 37° C. for up to 2 hours. Nuclease secreting clones develop an easily identifiable pink halo. Plasmid DNA was isolated from Nuc+ recombinant L. lactis clones and DNA inserts were sequenced on one strand using the NucSeq sequencing primer described in Appendix 1, which sequences directly through the DNA insert.

(iii) Isolation of Genes Encoding Exported Proteins from S. pneumoniae

A large number of gene sequences putatively encoding exported proteins in S. pneumoniae have been identified using the nuclease screening system. These have now been further analysed to remove artifacts. The sequences identified using the screening system have been analysed using a number of parameters.

1. All putative surface proteins were analysed for leader/signal peptide sequences using the software programs SEQUENCHER™ (Gene Codes Corporation) and DNA Strider (Marck, Nucleic Acids Res., 16:1829-1836 (1988)). Bacterial signal peptide sequences share a common design. They are characterised by a short positively charged N-terminus (N region) immediately preceding a stretch of hydrophobic residues (central portion-h region) followed by a more polar C-terminal portion which contains the cleavage site (c-region). Computer software is available which allows hydropathy profiling of putative proteins and which can readily identify the very distinctive hydrophobic portion (h-region) typical of leader peptide sequences. In addition, the sequences were checked for the presence of or absence of a potential ribosomal binding site (Shine-Dalgarno motif) required for translation initiation of the putative nuc reporter fusion protein.

2. All putative surface protein sequences were also matched with all of the protein/DNA sequences using the publicly available databases [OWL-proteins inclusive of SwissProt and GenBank translations]. This allows us to identify sequences similar to known genes or homologues of genes for which some function has been ascribed. Hence it has been possible to predict a function for some of the genes identified using the LEEP system and to unequivocally establish that the system can be used to identify and isolate gene sequences of surface associated proteins. We should also be able to confirm that these proteins are indeed surface related and not artifacts. The LEEP system has been used to identify novel gene targets for vaccine and therapy.

3. Some of the genes identified proteins did not possess a typical leader peptide sequence and did not show homology with any DNA/protein sequences in the database. Indeed these proteins may indicate the primary advantage of our screening method, i.e. the isolation of atypical surface-related proteins, which may have been missed in all previously described screening protocols or approaches based on sequence homology searches.

In all cases, only partial gene sequences were initially obtained. Full length genes given in Table 2 were obtained in all cases by reference to the TIGR *S. pneumoniae* database (www.tigr.org). Thus, by matching the originally obtained partial sequences with the database, we were able to identify the full length gene sequences. Hence, as described herein, two groups of genes were clearly identified, ie a group of genes encoding previously unidentified *S. pneumoniae* proteins (Table 1), and a second group which encoded known *S. pneumoniae* proteins, which were, however, not known as antigens (Table 2).

Two further *S. pneumoniae* genomes have been recently sequenced and the information published and subsequently made available on the NCBI database. The "Annotated Draft Genomic Sequence from a *Streptococcus pneumoniae* Type 19F Clinical Isolate" was published in July 2001 by Dopazo et al. (Microbial Drug Resistance, Volume 7, pp 99-125). The "Genome of the Bacterium *Streptococcus pneumoniae* Strain R6 was published in October 2001 by Hoskins et al. (Journal of Bacteriology, Volume 183, pp 5709-5717). Through BLAST analysis, homologues of ID-304L1 have been identified in these genomes which all possess a highly conserved sequence of 23 amino acids either at or near their N-terminus:

MELVLPNNYVV(D,A)I(L)D(E)E(Q)EEMMYLDGG (E), (SEQ ID NO:45), where the bracketed residues represent alternatives to the preceding amino acid. Sequences for these homologues are given in Table 3.

Example 2

Conservation and Variability of ID-304L Variants Among Different Isolates of *Streptococcus pneumoniae*

The presence of genes ID304L1 and ID305 in the *S. pneumoniae* serotype 3 strain ATCC 49619 was investigated. Oligonucleotide primers were designed based upon the known nucleic acid sequences given in Table 1 and these gene targets were amplified by PCR.

(i) Amplification and Labelling of Specific Target Genes as DNA Probes for Southern Blot Analysis Oligonucleotide primers were designed to amplify corresponding gene-specific DNA probes (Appendix 2). Specific gene targets (ID304L1 and ID305) were amplified by PCR using PFUTURBO® DNA polymerase (Stratagene) according to the manufacturer's instructions. Typical reactions were carried out in a 50 µl volume containing 100 ng of template DNA, a one tenth volume of enzyme reaction buffer, 100 ng of each primer, 200 µM of each dNTP and 1.25 Units of PFUTURBO® DNA polymerase. A typical reaction contained an initial 3 minute denaturation at 95 C, followed by a single 60 second cycle at 94 C, followed by 30 cycles at 50 C for 60 seconds. A single cycle of 2 minutes at 72 C was then followed with a final extension period of 10 minutes at 72 C.

All PCR amplified products were purified using the QIAquick™ PCR Purification Kit (Qiagen). The presence of homologues to ID304L1 and ID305 in strain ATCC49619 was thereby confirmed.

For use as DNA probes, purified amplified gene DNA fragments from ID304L1 were labelled with digoxygenin using the DIG Nucleic Acid High Prime Labelling Kit (Roche) according to the manufacturer's instructions.

(ii) Southern Blot Hybridisation Analysis of Group B Streptococcal Genomic DNA

A Southern blot analysis was carried out to determine cross-serotype conservation of novel *Streptococcus pneumoniae* genes isolated using the LEEP system. The *Streptococcus pneumoniae* strains used in this analysis are given in the legend to FIG. 1.

Genomic DNA isolated from strains of *Streptococcus pneumoniae* were investigated for conservation of ID 304L1 derived gene targets. Appropriate DNA concentrations were digested using HindIII restriction enzymes (Roche) according to the manufacturer's instructions and analysed by agarose gel electrophoresis. Following agarose gel electrophoresis of DNA samples, the gel was denatured in 0.5M NaOH-1.5M NaCl for 20 minutes, neutralised in 0.5M Tris HCl (pH 7.5)-1.5M NaCl for 40 minutes and DNA was transferred onto Hybond™ N+ membrane (Amersham) by overnight capillary blotting. The method is essentially as described in "The DIG System User's Guide for Filter Hybridization" (Boehringer Mannheim, 1995) using Whatman 3MM wicks on a platform over a reservoir of 20×SSC (salt sodium citrate). After transfer, the filter was washed briefly in 2×SSC and stored at −20 C.

Filters were pre-hybridised, hybridised with the digoxygenin labelled DNA probes and washed using conditions recommended by Boehringer Mannheim when using their DIG Nucleic Acid Detection Kit. Filters were pre-hybridised at 42 C for one hour in DIG "EasyHyb". The digoxygenin labelled DNA probe was denatured at 100 C for 10 minutes and chilled on ice before being added to the hybridisation buffer (DIG"EasyHyb"). Hybridisation was allowed to proceed overnight in a rotating Hybaid tube in a Hybaid Mini-hybridisation oven. Unbound probe was removed by washing the filter twice with 2×SSC-0.1% SDS for 5 minutes at room temperature. For increased stringency, filters were then washed twice with 0.5×SSC-0.1% SDS for 15 minutes at 68 C. The DIG Nucleic Acid Detection Kit (Roche) was used to detect specifically bound digoxygenin labelled DNA probes immunologically.

The Southern blot hybridisation demonstrates the presence of an ID-304L1 homologue in the majority of the strains analysed. Lane 12, from which the probe was amplified, has only a very faint band, but this is due to a low level of DNA being applied to the gel in this case. This may also explain the absence of a band in Lane 5, where the background is significantly fainter than for the other lanes. In some strains two bands are observed which suggests that there may be more than one homologue present (as found in the G54 and R6 strains). The presence of genes for this protein in a wide number of clinically relevant strains indicates that this is a conserved protein that is a good vaccine candidate.

Appendix I—Oligonucleotide Primers for LEEP Screening nucS1
      Bgl II  Eco RV
5'- cgagatctgatatctcacaaacagataacggcgtaaatag -3' nucS2
      Bgl II  Sma I
5'- gaagatcttccccgggatcacaaacagataacggcgtaaat ag -3' nucS3
      Bgl II  EcoRV
5'- cgagatctgatatccatcacaaacagataacggcgtaaatag -3' nucR
      Bam HI
5'- cgggatccttatggacctgaatcagcgttgtc -3'

NucSeq
5'- ggatgctttgtttcaggtgtatc -3' pTREP$_F$
5'- catgatatcggtacctcaagctcatatcattgtccggcaatggtgt gggcttttttttgtttagcggataacaatttcacac -3' pTREP$_R$
5'- gcggatccccgggcttaattaatgtttaaacactagtcgaagatc tcgcgaattctcctgtgtgaaattgttatccgcta -3' pUC$_F$
5'- cgccagggttttcccagtcacgac -3'

V$_R$
5'- tcagggggcggagcctatg -3'

V$_1$
5'- tcgtatgttgtgtggaattgtg -3'

V$_2$
5'- tccggctcgtatgttgtgtggaattg -3'

Appendix 2—Oligonucleotide Primers for PCR Analysis and Southern Blotting

The primers were engineered to provide restriction enzyme sites for later use in cloning (given in bold type below). GGC clamps allowing the restriction enzymes greater binding capacity are underlined.

ID 305 Bam5'
GGC GGATCC ATA AAC GAA GAA ATA AGC AAG GAA GC

ID 305 Hind3'
GGC AAGCTT TTA GAT TTC TCT GGT CAT ATC

ID 304 L1 Bam5'
GGC GGATCC AAA CAA TTT CAA CTA AGG AGG

LID 304 L1 Hind3'
GGC AAGCTT TCA TCT TAC TGT CGC AGA TAT G

---

The invention claimed is:

1. A composition that comprises a *Streptococcus pneumoniae* protein or polypeptide, wherein said protein or polypeptide comprises one of the sequences selected from the group consisting of: SEQ ID NO:1, SEQ ID NO:3, and SEQ ID NO:5, and wherein said composition is substantially free of other *Streptococcus pneumoniae* proteins.

2. A composition that comprises a *Streptococcus pneumoniae* protein or polypeptide wherein said protein or polypeptide comprises a sequence that has at least 80% sequence identity to one of the sequences selected from the group consisting of: SEQ ID NO: 1, SEQ ID NO:3, and SEQ ID NO:5, and wherein said composition is substantially free of other *Streptococcus pneumoniae* proteins.

3. A method for eliciting an anti-Streptococcal immune response in a subject comprising administering to the subject an antigenic composition, said composition comprising a protein or polypeptide comprising one of the sequences selected from the group consisting of: SEQ ID NO:1, SEQ ID NO:3, and SEQ ID NO:5, as an antigen.

4. An antigenic composition comprising one or more proteins or polypeptides that comprise one or more of the sequences selected from the group consisting of: SEQ ID NO:1, SEQ ID NO:3, and SEQ ID NO:5, wherein said composition is substantially free of other *Streptococcus pneumoniae* proteins.

5. The composition of claim 4, wherein said composition comprises one or more additional components selected from excipients, diluents or adjuvants.

6. The composition of claim 2, wherein said identity is at least 90%.

7. The composition of claim 6, wherein said identity is at least 95%.

* * * * *

SEQUENCE LISTING

<160> NUMBER OF SEQ ID NOS: 60

<210> SEQ ID NO 1
<211> LENGTH: 28
<212> TYPE: PRT
<213> ORGANISM: Streptococcus pneumoniae

<400> SEQUENCE: 1

Met Ala Gly Asn Ser Phe His Leu Thr Leu Thr Ser Val Ser Gln Ala
1              5                   10                  15

Gly Gln Gln Thr Leu Arg His Asn His Ser Pro Ile
        20                   25

<210> SEQ ID NO 2
<211> LENGTH: 84
<212> TYPE: DNA
<213> ORGANISM: Streptococcus pneumoniae

<400> SEQUENCE: 2
atggcaggca attcctttca cctaactctc acttctgtat ctcaggcagg acaacaaacg     60
cttcgacaca atcacagtcc tatt     84

<210> SEQ ID NO 3
<211> LENGTH: 171
<212> TYPE: PRT
<213> ORGANISM: Streptococcus pneumoniae

<400> SEQUENCE: 3

Met Ile Asn Glu Glu Ile Ser Lys Glu Ala Gly Gln Ala Ala Gln Thr
1              5                   10                  15

Ile Ile Ser Tyr Thr Ile Lys Ala Thr Lys Glu Ser Ile Asn Leu Glu
        20                   25                  30

```
Lys Glu Ile Arg Lys Lys Met Asn Glu Thr Leu Glu Lys Ala Asn Gly
                35                  40                  45

Asn Leu Lys Ser Leu Met Gly Asp Glu Met Lys Ile Lys Asp Leu Tyr
 50                  55                  60

Lys Lys Gly Gln Leu Glu Asn Ile Ser Ile Asp Gln Ile Asp Leu Lys
 65                  70                  75                  80

Asp Leu Lys Lys Glu Leu Asn Lys Leu Gly Val Ser Phe Ser Val Met
                 85                  90                  95

Lys Asn Lys Glu Ser Lys Asn Tyr Glu Ile Phe Phe Gln Ala Lys Asp
                100                 105                 110

Ile Lys Val Met Glu Tyr Ala Phe Lys Gln Val Ile Ala Lys Glu Asn
                115                 120                 125

Lys Lys Glu Lys Glu Ser Ile Leu Lys Gln Ile Lys Lys Tyr Lys Asp
                130                 135                 140

Leu Ser Lys Asn Lys Asp Lys Thr Lys Glu Leu Gly Lys Arg Lys Val
145                 150                 155                 160

Lys Pro Asn Lys Lys Asp Met Thr Arg Glu Ile
                165                 170

<210> SEQ ID NO 4
<211> LENGTH: 525
<212> TYPE: DNA
<213> ORGANISM: Streptococcus pneumoniae

<400> SEQUENCE: 4
atgataaacg aagaaataag caaggaagca ggtcaagcag cacaaaccat aatatcatac      60
acaataaagg caacaaaaga atcaatcaat ttagaaaaag aaataagaaa aagatgaat     120 gaaactttag aaaaagcaaa tggaaactta aaaagtctta tgggcgatga atgaaaata    180 aaagacctct acaagaaagg acaactagaa atataagca tagatcaaat cgacctcaaa     240
gacttaaaaa agaactaaa caaacttgga gtaagtttct cagtaatgaa aaacaaagaa     300
agcaaaaact atgaaatatt cttccaagcc aaagacataa agtaatgga atatgccttt     360 aagcaagtca tagccaagga aaataaaaaa gaaaagaaa gtatcctaaa acaaataaag     420
aaatacaaag acctatccaa aaacaaagat aagacaaaag aaaaggaaa aggaaagta     480 aaagaaaaag taaaaccaaa caaaaaagat atgaccagag aaatc                   525

<210> SEQ ID NO 5
<211> LENGTH: 189
<212> TYPE: PRT
<213> ORGANISM: Streptococcus pneumoniae

<400> SEQUENCE: 5

Met Lys Val Ser Lys Lys Ile Thr Leu Phe Ser Leu Ser Phe Ala Gly
 1               5                  10                  15

Phe Val Leu Leu Thr Leu Pro Gln Ala Gly Lys Ala Phe Glu Leu Lys
                 20                  25                  30

Glu Asp Trp Ala Phe Lys Gly Gly Ile Arg Tyr Glu Asn Gly Lys Val
                 35                  40                  45

Ser Lys Ile Asn Asn Gly Tyr Glu Val Asn Ile Lys Val Leu Asp Leu
 50                  55                  60

Pro Ser Thr Ser Ala Ile Glu Trp Thr Val Arg Leu Asn Gly Glu Lys
 65                  70                  75                  80

Gln Asn Thr Asn Phe Leu Ala Glu Glu Arg Thr Val Ser Lys Thr Glu
                 85                  90                  95
```

Asp Lys Gly Arg Phe Leu His Phe Tyr Ile Pro Tyr Gly Tyr Arg Gly
                100                 105                 110

Asp Ile Val Val Glu Ala Lys Ser Gly Asn Glu Val Lys Thr Trp Ser
            115                 120                 125

Thr Lys Val Val Asp Asp Val Tyr Ser Asp Ser Ala Lys Ser Gly Tyr
130                 135                 140

Phe Ile Leu Asp Gly Glu Gln Ile Leu Glu Ser Ser Trp Asp Ser Val
145                 150                 155                 160

Asn Glu Ser Tyr Ile Ala Thr Leu Pro Thr Val Thr Ser Gly Lys Thr
                165                 170                 175

Val Val Ala Trp Arg Glu Lys Gly Thr Leu Asn Leu Ile
            180                 185

<210> SEQ ID NO 6
<211> LENGTH: 567
<212> TYPE: DNA
<213> ORGANISM: Streptococcus pneumoniae

<400> SEQUENCE: 6
atgaaagtat caaaaaaaat tacactattt agtttgtctt ttgcaggttt tgttttattg      60 actttaccctc aagcaggaaa ggcttttgaa cttaaagaag actgggcatt taaaggtggc    120
attcgatacg agaatgggaa agtcagcaaa attaataatg gatatgaagt aaatattaaa    180
gtgttagatt tacctagtac tagcgcaatc gaatggacag ttagattgaa tggagaaaag    240
caaaatacta acttcttagc ggaggaaaga actgtatcta aaactgaaga taagggacgt    300
ttcttgcact tttatatccc ctatggatat cgtggggata ttgtagtaga ggctaagagt    360
ggaaacgaag tgaagacttg gtctactaag gtagttgacg atgtttattc agattctgct    420
aagagtggct actttattct cgatggggaa caaatcttag aaagttcatg ggattccgta    480
aatgagtctt atattgcaac gcttccaact gtaacatcag gaaaaactgt tgttgcttgg    540
cgtgaaaaag gaactcttaa tttaatt                                        567

<210> SEQ ID NO 7
<211> LENGTH: 124
<212> TYPE: PRT
<213> ORGANISM: Streptococcus pneumoniae

<400> SEQUENCE: 7

Met Glu Leu Val Leu Pro Asn Asn Tyr Val Val Leu Glu Gln Glu Glu
1               5                   10                  15

Met Met Tyr Leu Asp Gly Gly Phe Ser Ile Pro Arg Trp Pro Val Ala
            20                  25                  30

Thr Ala Ile Asn Ile Ala Phe Asn Gly Val Leu Gly Gly Gly Ala Ile
            35                  40                  45

Ser Leu Val Arg Asn Tyr Ile Arg Asn Tyr Gly Leu Arg Arg Val Thr
    50                  55                  60

Ser Ala Ile Ala Gly Ala Ala Arg Tyr Val Gly Val Arg Val Ala
65                  70                  75                  80

Asn Arg Val Ala Gly Phe Ala Leu Ser Ala Ile Asn Gly Phe Ala Ala
                85                  90                  95

Trp Met Ser Ile Gly Asp Ala Ile Thr Thr Ile Trp Ala Asn Asn Asp
            100                 105                 110

Val Asn Arg Arg Asp Pro Asn Leu Asn Ala Leu Trp
            115                 120

<210> SEQ ID NO 8
<211> LENGTH: 375
<212> TYPE: DNA
<213> ORGANISM: Streptococcus pneumoniae

<400> SEQUENCE: 8

```
atggaactcg tattaccaaa taattatgtt gttcttgagc aagaagagat gatgtatctt      60
gatggggat tttctattcc gagatggcct gttgcaacag ccattaatat agctttaat      120
ggtgttttag gtggaggagc aatcagtcta gttagaaatt atattcgtaa ttatggtttg     180
cggcgagtta caagcgcaat tgctggagca gctgcaagat atgttggggt acgagttgca     240
aatagagtgg caggatttgc actgtctgct attaatggat ttgcagcttg gatgtcaatt     300
ggcgatgcta ttacaacaat ctgggccaac aatgatgtaa ataggagaga cccaaatta      360
aacgccttgt ggtaa                                                      375
```

<210> SEQ ID NO 9
<211> LENGTH: 725
<212> TYPE: PRT
<213> ORGANISM: Streptococcus pneumoniae

<400> SEQUENCE: 9

```
Met Lys Asp Thr Phe Lys Asn Val Leu Ser Phe Glu Phe Trp Gln Lys
1               5                   10                  15

Phe Gly Lys Ala Leu Met Val Val Ile Ala Val Met Pro Ala Ala Gly
            20                  25                  30

Leu Met Ile Ser Ile Gly Lys Ser Ile Val Met Ile Asn Pro Thr Phe
        35                  40                  45

Ala Pro Leu Val Ile Thr Gly Gly Ile Leu Glu Gln Ile Gly Trp Gly
    50                  55                  60

Val Ile Gly Asn Leu His Ile Leu Phe Ala Leu Ala Ile Gly Gly Ser
65                  70                  75                  80

Trp Ala Lys Glu Arg Ala Gly Gly Ala Phe Ala Ala Gly Leu Ala Phe
                85                  90                  95

Ile Leu Ile Asn Arg Ile Thr Gly Thr Ile Phe Gly Val Ser Gly Asp
            100                 105                 110

Met Leu Lys Asn Pro Asp Ala Met Val Thr Thr Phe Phe Gly Gly Ser
        115                 120                 125

Ile Lys Val Ala Asp Tyr Phe Ile Ser Val Leu Glu Ala Pro Ala Leu
    130                 135                 140

Asn Met Gly Val Phe Val Gly Ile Ile Ser Gly Phe Val Gly Ala Thr
145                 150                 155                 160

Ala Tyr Asn Lys Tyr Tyr Asn Phe Arg Lys Leu Pro Asp Ala Leu Ser
                165                 170                 175

Phe Phe Asn Gly Lys Arg Phe Val Pro Phe Val Ile Leu Arg Ser
            180                 185                 190

Ala Ile Ala Ala Ile Leu Leu Ala Ala Phe Trp Pro Val Val Gln Thr
        195                 200                 205

Gly Ile Asn Asn Phe Gly Ile Trp Ile Ala Asn Ser Gln Glu Thr Ala
    210                 215                 220

Pro Ile Leu Ala Pro Phe Leu Tyr Gly Thr Leu Glu Arg Leu Leu
225                 230                 235                 240

Pro Phe Gly Leu His His Met Leu Thr Ile Pro Met Asn Tyr Thr Ala
                245                 250                 255

Leu Gly Gly Thr Tyr Asp Ile Leu Thr Gly Ala Ala Lys Gly Thr Gln
            260                 265                 270
```

-continued

Val Phe Gly Gln Asp Pro Leu Trp Leu Ala Trp Val Thr Asp Leu Val
    275                 280                 285

Asn Leu Lys Gly Thr Asp Ala Ser Gln Tyr Gln His Leu Leu Asp Thr
290                 295                 300

Val His Pro Ala Arg Phe Lys Val Gly Gln Met Ile Gly Ser Phe Gly
305                 310                 315                 320

Ile Leu Met Gly Val Ile Val Ala Ile Tyr Arg Asn Val Asp Ala Asp
                325                 330                 335

Lys Lys His Lys Tyr Lys Gly Met Met Ile Ala Thr Ala Leu Ala Thr
                340                 345                 350

Phe Leu Thr Gly Val Thr Glu Pro Ile Glu Tyr Met Phe Met Phe Ile
    355                 360                 365

Ala Thr Pro Met Tyr Leu Val Tyr Ser Leu Val Gln Gly Ala Ala Phe
    370                 375                 380

Ala Met Ala Asp Val Val Asn Leu Arg Met His Ser Phe Gly Ser Ile
385                 390                 395                 400

Glu Phe Leu Thr Arg Thr Pro Ile Ala Ile Ser Ala Gly Ile Gly Met
                405                 410                 415

Asp Ile Val Asn Phe Val Trp Val Thr Val Leu Phe Ala Val Ile Met
                420                 425                 430

Tyr Phe Ile Ala Asn Phe Met Ile Gln Lys Phe Asn Tyr Ala Thr Pro
    435                 440                 445

Gly Arg Asn Gly Asn Tyr Glu Thr Ala Glu Gly Ser Glu Glu Thr Ser
    450                 455                 460

Ser Glu Val Lys Val Ala Ala Gly Ser Gln Ala Val Asn Ile Ile Asn
465                 470                 475                 480

Leu Leu Gly Gly Arg Val Asn Ile Val Asp Val Asp Ala Cys Met Thr
                485                 490                 495

Arg Leu Arg Val Thr Val Lys Asp Ala Asp Lys Val Gly Asn Ala Glu
                500                 505                 510

Gln Trp Lys Ala Glu Gly Ala Met Gly Leu Val Met Lys Gly Gln Gly
    515                 520                 525

Val Gln Ala Ile Tyr Gly Pro Lys Ala Asp Ile Leu Lys Ser Asp Ile
    530                 535                 540

Gln Asp Ile Leu Asp Ser Gly Glu Ile Pro Glu Thr Leu Pro Ser
545                 550                 555                 560

Gln Met Thr Glu Ala Gln Gln Asn Thr Val His Phe Lys Asp Leu Thr
                565                 570                 575

Glu Glu Val Tyr Ser Val Ala Asp Gly Gln Val Ala Leu Glu Gln
                580                 585                 590

Val Lys Asp Pro Val Phe Ala Gln Lys Met Met Gly Asp Gly Phe Ala
    595                 600                 605

Val Glu Pro Ala Asn Gly Asn Ile Val Ser Pro Val Ser Gly Thr Val
    610                 615                 620

Ser Ser Ile Phe Pro Thr Lys His Ala Phe Gly Ile Val Thr Glu Ala
625                 630                 635                 640

Gly Leu Glu Val Leu Val His Ile Gly Leu Asp Thr Val Ser Leu Glu
                645                 650                 655

Gly Lys Pro Phe Thr Val His Val Ala Glu Gly Gln Lys Val Ala Ala
                660                 665                 670

Gly Asp Leu Leu Val Thr Ala Asp Leu Asp Ala Ile Arg Ala Ala Gly
    675                 680                 685

Arg Glu Thr Ser Thr Val Val Val Phe Thr Asn Gly Asp Ala Ile Lys
    690                 695                 700

-continued

Ser Val Lys Leu Glu Lys Thr Gly Ser Leu Ala Ala Lys Thr Ala Val
705                 710                 715                 720

Ala Lys Val Glu Leu
            725

<210> SEQ ID NO 10
<211> LENGTH: 2127
<212> TYPE: DNA
<213> ORGANISM: Streptococcus pneumoniae

<400> SEQUENCE: 10

| | | | | | |
|---|---|---|---|---|---|
| ggtaaggctt | tgatggtagt | tatcgcggtt | atgccggctg | ctggtttgat | gatttcaatc      60 |
| ggtaagtcta | tcgtgatgat | taacccaacc | tttgcaccac | ttgtcatcac | aggtggaatt     120 |
| cttgagcaaa | tcggttgggg | ggttatcggt | aaccttcaca | ttttgtttgc | cctagccatt     180 |
| ggaggaagct | gggctaaaga | acgtgctggt | ggtgcttttcg | ccgctggtct | tgccttcatc     240 |
| ttgattaacc | gtatcactgg | tacaatcttt | ggtgtatcag | gcgatatgtt | gaaaaatcca     300 |
| gatgctatgg | taactacttt | ctttggtggt | tcaatcaaag | ttgctgatta | ctttatcagt     360 |
| gttcttgaag | ctccagcctt | gaacatgggg | gtattcgtag | ggattatctc | aggttttgta     420 |
| ggggcaactg | cttacaacaa | atactacaac | ttccgtaaac | ttcctgatgc | actttcattc     480 |
| ttcaacggga | acgtttcgt | accatttgta | gttattcttc | gttcagcaat | cgctgcaatt     540 |
| ctacttgctg | ctttctggcc | agtagttcaa | acaggtatca | taacttcgg | tatctggatt     600 |
| gccaactcac | aagaaactgc | tccaattctt | gcaccattct | gtatggtac | tttggaacgt     660 |
| ttgctcttgc | catttggtct | tcaccacatg | ttgactatcc | caatgaacta | cacagctctt     720 |
| ggtggtactt | atgacatttt | aactggtgca | gctaaaggta | ctcaagtatt | cggtcaagac     780 |
| ccactatggc | ttgcatgggt | aacagacctt | gtaaacctta | aggtactga | tgctagtcaa     840 |
| tatcaacact | tgttagatac | agtacatcca | gctcgtttca | aagttggaca | aatgatcggt     900 |
| tcattcggta | tcttgatggg | tgtgattgtt | gctatctacc | gtaatgttga | tgctgacaag     960 |
| aaacataaat | acaaaggtat | gatgattgca | acagctcttg | caacattctt | gacaggggtt    1020 |
| actgaaccaa | tcgaatacat | gttcatgttc | atcgcaacac | ctatgtatct | tgtttactca    1080 |
| cttgttcaag | gtgctgcctt | cgctatggct | gacgtcgtaa | acctacgtat | gcactcattc    1140 |
| ggttcaatcg | agttcttgac | tcgtacacct | attgcaatca | gtgctggtat | tggtatggat    1200 |
| atcgttaact | tcgtttgggt | aactgttctc | tttgctgtaa | tcatgtactt | tatcgcaaac    1260 |
| ttcatgattc | aaaaattcaa | ctacgcaact | ccagggcgca | acggaaacta | cgaaactgct    1320 |
| gaaggttcag | aagaaaccag | cagcgaagtg | aaagttgcag | caggctctca | agctgtaaac    1380 |
| attatcaacc | ttcttggtgg | acgtgtaaac | atcgttgatg | ttgatgcatg | tatgactcgt    1440 |
| cttcgtgtaa | ctgttaaaga | tgcagataaa | gtaggaaatg | cagagcaatg | gaaagcagaa    1500 |
| ggagctatgg | gtcttgtcat | gaaaggacaa | ggggttcaag | ctatctacgg | tccaaaagct    1560 |
| gacattttga | atctgatat | ccaagatatc | cttgattcag | gtgaaatcat | tcctgaaact    1620 |
| cttccaagcc | aaatgactga | agcacaacaa | aacactgttc | acttcaaaga | tcttactgag    1680 |
| gaagtttact | cagtagcaga | cggtcaagtt | gttgctttgg | aacaagtaaa | ggatccagta    1740 |
| tttgctcaaa | aaatgatggg | tgatggatttt | gcagtagaac | ctgcaaatgg | aaacattgta    1800 |
| tctccagttt | caggtactgt | gtcaagcatc | ttcccaacaa | acatgctttt | tggtattgtg    1860 |
| acggaagcag | gtcttgaagt | attggttcac | attggtttgg | acacagtaag | tcttgaaggt    1920 |
| aaaccattta | cagttcatgt | tgctgaagga | caaaaagttg | cagcaggaga | tctccttgtc    1980 |

```
acagctgact tggatgctat ccgtgcagca ggacgtgaaa cttcaacagt agttgtcttc    2040
acaaatggtg atgcaattaa atcagttaag ttagaaaaaa caggttctct tgcagctaaa    2100
acagcagttg ctaaagtaga attgtaa                                        2127
```

<210> SEQ ID NO 11
<211> LENGTH: 269
<212> TYPE: PRT
<213> ORGANISM: Streptococcus pneumoniae
<220> FEATURE:
<221> NAME/KEY: misc_feature
<222> LOCATION: (37)..(37)
<223> OTHER INFORMATION: X is Asn or Asp
<220> FEATURE:
<221> NAME/KEY: misc_feature
<222> LOCATION: (40)..(40)
<223> OTHER INFORMATION: X is Cys or Ser

<400> SEQUENCE: 11

```
Met Leu Leu Gln Lys Glu Leu Ile Pro Met Ile Glu Ala Asn Leu Pro
1               5                   10                  15

Asn Met Ala Tyr Ala Glu Lys Asp Ile Ala Lys Phe Phe Leu Lys Gln
            20                  25                  30

Gln Pro Leu Asn Xaa Tyr Ser Xaa Lys Ala Leu Cys Glu Tyr Leu Asn
        35                  40                  45

Val Ser Lys Ala Thr Leu Thr Arg Phe Ala Lys Cys Gly Phe Lys
50                  55                  60

Gly Phe Arg Gln Phe Ile Phe Lys Tyr Gln Glu Met Ile His Glu Lys
65                  70                  75                  80

Glu Lys Leu Ala Leu Tyr Thr Glu Ala Thr Glu Lys Val Leu Ser Asp
                85                  90                  95

Tyr Glu Glu Met Leu Arg Lys Thr Tyr Thr Val Leu Asp Glu Val Gln
            100                 105                 110

Leu Glu Arg Ile Ala Glu Met Ile Glu Thr Ala Glu Arg Val Tyr Leu
        115                 120                 125

Tyr Gly Lys Gly Ser Ser Val Leu Ala Leu Gln Glu Met Lys Met Arg
130                 135                 140

Phe Met Arg Leu Gly Val Ile Gly Glu Val Leu Ser Asp Glu Asp Met
145                 150                 155                 160

Ile Leu Trp Ser Ser Leu Leu Leu Asn Glu Asn Cys Leu Val Ile Gly
                165                 170                 175

Ala Ser Ile Ser Gly Gln Thr Asp Ile Val Leu Glu Gly Leu Gln Lys
            180                 185                 190

Ala Ala Asp Lys Gly Ala Lys Thr Val Leu Met Thr Thr Arg Lys Phe
        195                 200                 205

Asp Glu Glu Asp Cys Phe Phe Asp Glu Leu Leu Leu Ala Ser Thr
210                 215                 220

Asp His Leu Ser Tyr Gly Asn Arg Ile Ser Pro Gln Phe Pro Ile Leu
225                 230                 235                 240

Leu Ile Thr Asp Cys Leu Phe Ser Asn Tyr Leu Glu Ser Pro Glu Arg
                245                 250                 255

Gln Tyr Tyr Tyr Asn Gln Thr Ile Ile His Lys Glu Glu
            260                 265
```

<210> SEQ ID NO 12
<211> LENGTH: 810
<212> TYPE: DNA
<213> ORGANISM: Streptococcus pneumoniae

<400> SEQUENCE: 12

```
atgttactgc aaaagaact aattccaatg atagaagcta acttaccaaa tatggcatat      60
gctgaaaaag acattgctaa attcttctta aaacagcaac ctctgaatra ttattcatst    120
aargcattgt gcaatacct taatgtatcc aaagcaacat tgactcgatt tgcgaaaaaa    180
tgtggtttta aaggttttag acaattcatt ttcaaatacc aagagatgat tcatgagaaa    240
gaaaagttgg cattatatac agaggcaaca gaaaagttt tatccgacta tgaggaaatg     300
ttgagaaaaa cttacacggt tcttgatgaa gttcaacttg agcgtattgc tgagatgata    360
gaaactgctg agcgtgtata tctctacggt aaaggaagtt ctgttcttgc tttacaagaa    420
atgaagatga gatttatgcg tctcggagtg attggtgaag tattatcaga cgaggatatg    480
attttgtgga gtagcttact acttaatgaa aattgccttg tcattggagc atccatttca    540
ggtcaaactg atattgtact agaaggtcta caaaaagctg cagataaagg cgctaaaaca    600
gtttaatga ctacaagaaa atttgacgaa gaagattgtt tctttgatga actattgtta     660
ttagcttcga ccgatcatct ctcgtatggc aatcgcatat cacctcagtt tccaatactt    720
ttaattacag actgcttatt ctctaattat ctggaaagtc cagagagaca atattattac    780
aatcaaacta ttatccataa ggaggaataa                                     810
```

<210> SEQ ID NO 13
<211> LENGTH: 462
<212> TYPE: PRT
<213> ORGANISM: Streptococcus pneumoniae

<400> SEQUENCE: 13

```
Met Asn Lys Ser Arg Leu Gly Arg Gly Arg His Gly Lys Thr Arg His
1               5                   10                  15

Ile Leu Leu Ala Leu Ile Gly Ile Leu Ala Ile Ser Ile Cys Leu Leu
            20                  25                  30

Gly Gly Phe Ile Ala Phe Lys Ile Tyr Gln Gln Lys Ser Phe Glu Gln
        35                  40                  45

Lys Ile Glu Ser Leu Lys Lys Glu Lys Asp Asp Gln Leu Ser Glu Gly
    50                  55                  60

Asn Gln Lys Glu His Phe Arg Gln Gly Gln Ala Glu Val Ile Ala Tyr
65                  70                  75                  80

Tyr Pro Leu Gln Gly Glu Lys Val Ile Ser Val Arg Glu Leu Ile
                85                  90                  95

Asn Gln Asp Val Lys Asp Lys Leu Glu Ser Lys Asp Asn Leu Val Phe
            100                 105                 110

Tyr Tyr Thr Glu Gln Glu Glu Ser Gly Leu Lys Gly Val Val Asn Arg
        115                 120                 125

Asn Val Thr Lys Gln Ile Tyr Asp Leu Val Ala Phe Lys Ile Glu Glu
    130                 135                 140

Thr Glu Lys Thr Ser Leu Gly Lys Val His Leu Thr Glu Asp Gly Gln
145                 150                 155                 160

Pro Phe Thr Leu Asp Gln Leu Phe Ser Asp Ala Ser Lys Ala Lys Glu
                165                 170                 175

Gln Leu Ile Lys Glu Leu Thr Ser Phe Ile Glu Asp Lys Lys Ile Glu
            180                 185                 190

Gln Asp Gln Ser Glu Gln Ile Val Lys Asn Phe Ser Asp Gln Asp Leu
        195                 200                 205

Ser Ala Trp Asn Phe Asp Tyr Lys Asp Ser Gln Ile Ile Leu Tyr Pro
    210                 215                 220
```

```
Ser Pro Val Val Glu Asn Leu Glu Glu Ile Ala Leu Pro Val Ser Ala
225                 230                 235                 240

Phe Phe Asp Val Ile Gln Ser Ser Tyr Leu Leu Glu Lys Asp Ala Ala
            245                 250                 255

Leu Tyr Gln Ser Tyr Phe Asp Lys Lys His Gln Lys Val Ala Leu
        260                 265                 270

Thr Phe Asp Asp Gly Pro Asn Pro Ala Thr Thr Pro Gln Val Leu Glu
    275                 280                 285

Thr Leu Ala Lys Tyr Asp Ile Lys Ala Phe Phe Val Leu Gly Lys Asn
        290                 295                 300

Val Ser Gly Asn Glu Asp Leu Val Lys Arg Ile Lys Ser Glu Gly His
305                 310                 315                 320

Val Val Gly Asn His Ser Trp Ser His Pro Ile Leu Ser Gln Leu Ser
            325                 330                 335

Leu Asp Glu Ala Lys Lys Gln Ile Thr Asp Thr Glu Asp Val Leu Thr
        340                 345                 350

Lys Val Leu Gly Ser Ser Ser Lys Leu Met Arg Pro Pro Tyr Gly Ala
        355                 360                 365

Ile Thr Asp Asp Ile Arg Asn Ser Leu Asp Leu Ser Phe Ile Met Trp
    370                 375                 380

Asp Val Asp Ser Leu Asp Trp Lys Ser Lys Asn Glu Ala Ser Ile Leu
385                 390                 395                 400

Thr Glu Ile Gln Tyr Gln Val Ala Asn Gly Ser Ile Val Leu Met His
            405                 410                 415

Asp Ile His Ser Pro Thr Val Asn Ala Leu Pro Arg Val Ile Glu Tyr
        420                 425                 430

Leu Lys Asn Gln Gly Tyr Thr Phe Val Thr Ile Pro Glu Met Leu Asn
        435                 440                 445

Thr Arg Leu Lys Ala His Glu Leu Tyr Tyr Ser Arg Asp Glu
    450                 455                 460

<210> SEQ ID NO 14
<211> LENGTH: 1392
<212> TYPE: DNA
<213> ORGANISM: Streptococcus pneumoniae
<220> FEATURE:
<221> NAME/KEY: misc_feature
<222> LOCATION: (892)..(892)
<223> OTHER INFORMATION: n is A or no nucleotide
<220> FEATURE:
<221> NAME/KEY: misc_feature
<222> LOCATION: (893)..(893)
<223> OTHER INFORMATION: n is C or no nucleotide
<220> FEATURE:
<221> NAME/KEY: misc_feature
<222> LOCATION: (894)..(894)
<223> OTHER INFORMATION: n is T or no nucleotide

<400> SEQUENCE: 14
atgaataaaa gtagactagg acgtggcaga cacgggaaaa cgagacatrt attattggct    60
ttgattggta ttttagcaat ttctatttgc ctattaggcg gatttattgc ttttaagatc   120
taccagcaaa aaagttttga gcaaaagatt gaatcgctca aaaaagagaa agatgatcaa   180
ttgagtgagg gaaatcagaa ggagcatttt cgtcagggc aagccgaagt gattgcctat   240
tatcctctcc aaggggagaa agtgatttcc tctgttaggg agytgataaa tcaagatgtt   300
aaggacaagc tagaaagtaa ggacaatctt gttttctact atacagagca agaagagtca   360
ggtttaaagg gagtcgttaa tcgtaatgtg accaaacaaa tctatgattt agttgctttt   420
aagattgaag agactgaaaa gaccagtcta ggaaaggttc acttaacaga gatgggcaa    480
```

```
cctttttacac ttgaccaact gttttcagat gctagtaagg ctaaggaaca gctgataaaa      540
gagttgacct ccttcataga ggataaaaaa atagagcaag accagagtga gcagattgta      600
aaaaacttct ctgaccaaga cttgtctgca tggaattttg attacaagga tagtcagatt      660
atcctttatc caagtcctgt ggttgaaaat ttagaagaga tagccttgcc agtatctgct      720
ttctttgatg ttatccaatc ttcgtactta ctcgaaaaag atgcggcctt gtaccaatct      780
tactttgata gaaacatca aaaagttgtc gctctaacct tgatgatgg tccaaatcca        840 gcaacgaccc cgcaggtatt agagaccta gctaaatatg atattaaagc gnnnttcttt       900
gtgcttggga aaaatgtttc tgggaatgag acttggtga agaggataaa atctgaaggt       960
catgttgttg gaaaccatag ctggagccat ccgattctct cgcaactctc tcttgatgaa     1020
gctaaaaagc agattactga tactgaggat gtgctaacta agtgctggg ttctagttct      1080 aaactcatgc gtccaccta tggtgctatt acagatgata ttcgcaatag cttggattg      1140 agctttatca tgtgggatgt ggatagtctg gactggaaga gtaaaaatga agcatctatt     1200
ttgacagaaa ttcagtatca agtagctaat ggctctatcg ttttgatgca tgatattcac     1260
agtccgacag tcaatgcctt gccaagggtc attgagtatt tgaaaaatca aggttatacc     1320
tttgtgacca taccagagat gctcaatact cgcctaaaag ctcatgagct gtactatagt     1380
cgtgatgaat aa                                                        1392

<210> SEQ ID NO 15
<211> LENGTH: 101
<212> TYPE: PRT
<213> ORGANISM: Streptococcus pneumoniae

<400> SEQUENCE: 15

Met Phe Val Lys Lys Gly Asp Lys Val Arg Val Ile Ala Gly Lys Asp
1               5                   10                  15

Lys Gly Thr Glu Ala Val Val Leu Thr Ala Leu Pro Lys Val Asn Lys
            20                  25                  30

Val Ile Val Glu Gly Val Asn Ile Val Lys Lys His Gln Arg Pro Thr
        35                  40                  45

Asn Glu Leu Pro Gln Gly Gly Ile Ile Glu Lys Glu Ala Ala Ile His
    50                  55                  60

Val Ser Asn Val Gln Val Leu Asp Lys Asn Gly Val Ala Gly Arg Val
65                  70                  75                  80

Gly Tyr Lys Phe Val Asp Gly Lys Lys Val Arg Tyr Asn Lys Lys Ser
                85                  90                  95

Gly Glu Val Leu Asp
            100

<210> SEQ ID NO 16
<211> LENGTH: 306
<212> TYPE: DNA
<213> ORGANISM: Streptococcus pneumoniae

<400> SEQUENCE: 16
atgtttgtaa aaaaaggcga caaagttcgc gtaatcgctg gtaaagataa gggaacagaa       60
gctgttgtcc ttactgccct tccaaaagta aacaaagtta tcgttgaagg tgttaacatt      120
gttaagaaac accaacgtcc aactaacgag cttcctcaag gtggtatcat cgagaaagaa      180
gcagctatcc acgtatcaaa cgttcaagtt ttggacaaaa atggtgtagc tggtcgtgtt      240
ggatacaaat ttgtagacgg taaaaagtt cgctacaaca aaaatcagg cgaagtgctt       300 gattaa                                                               306
```

<210> SEQ ID NO 17
<211> LENGTH: 702
<212> TYPE: PRT
<213> ORGANISM: Streptococcus pneumoniae

<400> SEQUENCE: 17

```
Met Lys Lys Ile Ser Asn Phe Cys Met Leu Leu Leu Leu Cys Thr
1               5                   10                  15

Thr Phe Phe Val Phe Asn Val Asn Tyr Thr Arg Glu Val Val Arg Ile
                20                  25                  30

Gln Glu Met Gly Lys Thr Val Asp Ser Leu Asp Leu Tyr Leu Lys Asp
            35                  40                  45

Ile Asn Glu Pro Ala Ala Ser Val Leu Arg Phe Phe Glu Asp Val Ser
50                  55                  60

Lys Glu Tyr Lys Val Ser Ile Ile Lys Thr Asp Ser Gly Asp Glu Val
65                  70                  75                  80

Val Lys Ser Gly Val Phe Asp Lys Asp Thr Phe Pro Tyr Gln Glu Phe
                85                  90                  95

Gly Ile Ser Ser Leu Asp Phe Thr Thr Asp Gly Glu Gly Val Tyr Ser
            100                 105                 110

Asn Lys Glu Ile Ser Asn Lys Leu Gly Thr Ile Pro Thr Phe Leu Lys
        115                 120                 125

Ala Lys Pro Ile Gln Leu Met Thr Phe Gln Thr Tyr Ile Lys Asp Thr
    130                 135                 140

Ser Arg Ser Leu Asn Gly Arg Tyr Thr Ile Thr Ser Thr Gln Glu Met
145                 150                 155                 160

Asp Lys Asp Arg Ile Val Gln Lys Trp Ser Asp Phe Phe Lys Ile Asp
                165                 170                 175

Gln Ala Thr Leu Leu Glu Pro Thr Tyr Lys Ser Ala Val Glu Val Ile
            180                 185                 190

Asn Arg Asp Leu Leu Leu Ser Ala Ile Val Phe Val Leu Ala Ile Leu
        195                 200                 205

Leu Leu Val Leu Val Thr Val Tyr Gln Pro Met Met Glu Met Lys Arg
    210                 215                 220

Val Gly Val Gln Lys Leu Leu Gly Phe Gln Asp Arg Ala Val Leu Ala
225                 230                 235                 240

Asp Val Val Lys Gly Asn Leu Tyr Leu Leu Gly Gly Ala Leu Val
                245                 250                 255

Ile Asn Leu Gly Val Phe Phe Leu Leu Asp Tyr Lys Pro Lys Asp Leu
            260                 265                 270

Phe Pro Met Leu Trp Leu Ser His Phe Leu Leu Gln Leu Tyr Leu
        275                 280                 285

Phe Ile Ser Trp Leu Thr Tyr Leu Leu Ile Gln Lys Met Thr Ile Ser
    290                 295                 300

Ser Leu Leu Lys Gly Phe Ser Ser Phe Lys Phe Gly Leu Ile Phe Asn
305                 310                 315                 320

Tyr Val Met Lys Ile Gly Thr Thr Ile Leu Leu Thr Ala Leu Leu Ile
                325                 330                 335

Gly Val Gly Arg Ser Leu Glu Gln Glu Asn Lys Glu Leu Ala Tyr Gln
            340                 345                 350

Gln Gln Trp Val Ser Gln Gly Asn Tyr Leu Leu Glu Thr Phe Lys
        355                 360                 365

Leu Asn Asp Asn Leu Trp Gln Glu Glu Leu Ala Gly Ser Gly Lys Ser
    370                 375                 380
```

```
Thr Asp Tyr Phe Tyr Arg Phe Tyr Gln Asp Leu Val Glu Lys Thr Gln
385                 390                 395                 400

Ala Gly Tyr Val Gln Ser Ser Ser Leu Pro Val Lys Asn Phe Val Gln
                405                 410                 415

Ser Glu Gln Ile Gln Gln Tyr Gln Leu Thr Asp Thr Val Asp Val Tyr
            420                 425                 430

Tyr Ala Asn Arg Asn Phe Leu Lys Ser Lys Gly Phe Lys Leu Pro Asn
        435                 440                 445

Thr Gly Ile Lys Lys Val Ile Leu Met Pro Ala Ser Thr Lys Gly Glu
450                 455                 460

Glu Asp Lys Asn Gln Leu Leu Gly Lys Leu Ile Ala Phe His Ser Met
465                 470                 475                 480

Lys Tyr Glu Glu Gln Gln Lys Arg Thr Ile Glu Glu Met Asp Val Glu
                485                 490                 495

Ile Ala Tyr Tyr Glu Gly Asp Trp Ser Phe Phe Pro Tyr Ser Asp Lys
            500                 505                 510

Arg Lys Glu Asn Leu Ser Asn Pro Ile Ile Ser Leu Val Asn Asp Ser
        515                 520                 525

Asp Met Met Trp Asp Glu Lys Ala Ser Leu Ser Thr Thr Gly Leu Asn
530                 535                 540

Asn Pro Ile Lys Ile Glu Asn Thr Val Gln His Gln Lys Glu Ile Thr
545                 550                 555                 560

Glu Leu Val Glu Lys Leu Ser Asp Gly Asn Tyr Leu Lys Phe Ser Ser
                565                 570                 575

Ile Gln Ala Ile Gln Gln Glu Lys Val Asp Ser Tyr Arg Asp Ala Val
            580                 585                 590

Arg Asn Phe Asn Leu Leu Phe Ala Leu Phe Gly Leu Leu Ser Met Met
        595                 600                 605

Ile Ser Tyr Phe Leu Leu Val Thr Thr Phe Leu Leu Lys Arg Arg Asp
610                 615                 620

Ile Ile Thr Lys Lys Phe Met Gly Trp Lys Leu Val Asp Arg Tyr Arg
625                 630                 635                 640

Pro Leu Leu Val Leu Leu Leu Gly Tyr Ser Phe Pro Leu Leu Val
                645                 650                 655

Leu Ile Phe Phe Ala His Ala Phe Leu Pro Leu Leu Leu Phe Ala Gly
            660                 665                 670

Phe Thr Cys Leu Asp Ile Leu Phe Val Leu Gly Leu Ala Ser Arg Met
        675                 680                 685

Glu Lys Arg Ser Leu Val Glu Leu Leu Lys Gly Gly Ile Leu
690                 695                 700
```

<210> SEQ ID NO 18
<211> LENGTH: 2109
<212> TYPE: DNA
<213> ORGANISM: Streptococcus pneumoniae

<400> SEQUENCE: 18

```
atgaaaaaaa tcagtaattt ctgtatgtta ctcctgcttc tgtgtaccac ttttttttgtt      60
tttaatgtaa actatacacg agaagtggtt cggattcaag aaatgggaaa gactgtagat     120
tctttggatt tgtatttgaa agatattaac gaacctgcag cgtctgttct tcgattttt      180
gaggatgtat caaggagta taaagtctcc atcatcaaaa cagacagtgg tgatgaggtg     240
gtcaagtctg tgtttttga taaagatacc ttccccctacc aagagtttgg gatttcttct     300
cttgatttta ccacagatgg tgaaggagtc tatagtaata agaaatttc caataaactt     360
```

```
ggtacgattc cgacctttct aaaagccaaa cctattcagc ttatgacttt tcaaacctat    420
atcaaggata catctcgtag tttaaatggt cgctatacga taacttctac acaagagatg    480
gacaaggata ggattgtaca gaaatggagc gatttttttca agatagacca ggctaccttg   540
ctagagccga cctacaaaag tgcagtggaa gtcataaatc gagatttgct tttatctgcc    600 attgttttg tcttggctat tttgcttctt gtgttagtga cagtgtatca accgatgatg    660
gagatgaaaa gagttggggt acaaaaatta cttggttttc aagatagggc tgttttagct   720
gatgttgtaa aaggcaacct ttacctcctc ctaggtgggg ctcttgtgat caatctaggc   780 gtgttttttct tgcttgatta taagccaaaa gatttgtttc ctatgctgtg gttgtctcat   840
tttttgctgt tgcagcttta tctctttatc agttggttga cttacctctt aatccaaaaa   900
atgacaatca gctctctgct gaaaggtttt tcatctttca aatttggtct tatcttcaat   960
tatgtgatga aaatagggac aactatttta ctgacggcct tactgattgg ggtgggcaga   1020
agtttagaac aagaaaacaa agaacttgct tatcagcaac agtgggtaag tcaaggtaat   1080
tacctgacct tagaaaacctt caaactcaat gataatctgt ggcaagaaga gctagcaggg   1140
tcagggaaat ctacagatta tttctatcga ttttatcagg atttggtaga aaaaacgcag   1200
gcgggctatg tgcagagtag cagtcttcct gtaaaaaatt ttgtccaatc agaacagatt   1260
cagcaatatc agttaacaga tacggtggat gtttactatg ccaatcgcaa ttttctaaag   1320
agcaagggat tcaagctacc aaataccggt attaaaaaag ttatttttgat gccagcaagt   1380 acgaaaggtg aagaagataa aaatcagctc ttggggaagt taattgcctt tcattcgatg   1440
aagtatgaag agcagcaaaa acgaacgata gaggagatgg atgtcgagat tgcctattat   1500
gaaggagatt ggtcattttt cccatatagt gataagcgaa aggaaaatct ctccaatcca   1560
attattagct tggtcaatga ttctgatatg atgtgggatg agaaagcctc cctgtcaaca   1620
actggcttaa ataatccgat taaaattgaa aatacggttc aacatcaaaa agagattaca   1680
gagttagttg agaaattgtc agatggaaat tatttaaaat tttcatctat tcaagccatt   1740
caacaagaga aagtggattc ttatcgagat gctgttcgga attttaacct actctttgct   1800
ttgtttggtc tccttagcat gatgatttcc tacttcttac tagtaacaac tttcttattg   1860
aagcgcaggg atatcattac caagaagttt atggggtgga aactggtcga tcgctaccgt   1920
cctctcctcg ttctgctctt gctgggctat agtttccctc ttctagtctt gattttcttt   1980
gcccatgcgt tcttaccact tctactgttt gcaggtttta catgtctgga tatactattt   2040
gtgctaggct tagcttctag gatggagaaa agaagtctag tagagttatt gaaaggggc    2100 atcttatga                                                           2109
```

<210> SEQ ID NO 19
<211> LENGTH: 448
<212> TYPE: PRT
<213> ORGANISM: Streptococcus pneumoniae

<400> SEQUENCE: 19

```
Met Pro Ile Thr Ala Ala Asp Ile Arg Arg Glu Val Lys Glu Lys Asn
1               5                   10                  15

Val Thr Phe Ile Arg Leu Met Phe Ser Asp Ile Leu Gly Thr Met Lys
            20                  25                  30

Asn Val Glu Ile Pro Ala Thr Asp Glu Gln Leu Asp Lys Val Leu Ser
        35                  40                  45

Asn Lys Val Met Phe Asp Gly Ser Ser Ile Glu Gly Phe Val Arg Ile
    50                  55                  60
```

-continued

Asn Glu Ser Asp Met Tyr Leu Tyr Pro Asp Leu Asp Thr Trp Thr Val
 65                  70                  75                  80

Phe Pro Trp Gly Asp Glu Asn Gly Ser Val Ala Gly Leu Ile Cys Asp
             85                  90                  95

Val Tyr Thr Thr Glu Gly Glu Pro Phe Ala Gly Asp Pro Arg Gly Asn
            100                 105                 110

Leu Lys Arg Ala Leu Arg His Met Glu Glu Val Gly Phe Lys Ser Phe
        115                 120                 125

Asn Leu Gly Pro Glu Pro Glu Phe Phe Leu Phe Lys Leu Asp Glu Asn
    130                 135                 140

Gly Asp Pro Thr Leu Glu Val Asn Asp Lys Gly Tyr Phe Asp Leu
145                 150                 155                 160

Ala Pro Thr Asp Leu Ala Asp Asn Thr Arg Arg Glu Ile Val Asn Val
                165                 170                 175

Leu Thr Lys Met Gly Phe Glu Val Glu Ala Ser His His Glu Val Ala
            180                 185                 190

Val Gly Gln His Glu Ile Asp Phe Lys Tyr Asp Glu Val Leu Arg Ala
        195                 200                 205

Cys Asp Lys Ile Gln Ile Phe Lys Leu Val Val Lys Thr Ile Ala Arg
    210                 215                 220

Lys His Gly Leu Tyr Ala Thr Phe Met Ala Lys Pro Lys Phe Gly Ile
225                 230                 235                 240

Ala Gly Ser Gly Met His Cys Asn Met Ser Leu Phe Asp Ala Glu Gly
                245                 250                 255

Asn Asn Ala Phe Phe Asp Pro Asn Asp Pro Lys Gly Met Gln Leu Ser
            260                 265                 270

Glu Thr Ala Tyr His Phe Leu Gly Gly Leu Ile Lys His Ala Tyr Asn
        275                 280                 285

Tyr Thr Ala Ile Met Asn Pro Thr Val Asn Ser Tyr Lys Arg Leu Val
    290                 295                 300

Pro Gly Tyr Glu Ala Pro Val Tyr Ile Ala Trp Ala Gly Arg Asn Arg
305                 310                 315                 320

Ser Pro Leu Val Arg Val Pro Ala Ser Arg Gly Met Gly Thr Arg Leu
                325                 330                 335

Glu Leu Arg Ser Val Asp Pro Met Ala Asn Pro Tyr Val Ala Met Ala
            340                 345                 350

Val Leu Leu Glu Val Gly Leu Tyr Gly Ile Glu Asn Lys Ile Glu Ala
        355                 360                 365

Pro Ala Pro Ile Glu Glu Asn Ile Tyr Ile Met Thr Ala Glu Glu Arg
    370                 375                 380

Lys Glu Ala Gly Ile Thr Asp Leu Pro Ser Thr Leu His Asn Ala Leu
385                 390                 395                 400

Lys Ala Leu Thr Glu Asp Glu Val Val Lys Ala Ala Leu Gly Asp His
                405                 410                 415

Ile Tyr Thr Ser Phe Leu Glu Ala Lys Arg Ile Glu Trp Ala Ser Tyr
            420                 425                 430

Ala Thr Phe Val Ser Gln Trp Glu Ile Asp Asn Tyr Leu Asp Leu Tyr
        435                 440                 445

<210> SEQ ID NO 20
<211> LENGTH: 1347
<212> TYPE: DNA
<213> ORGANISM: Streptococcus pneumoniae

```
<400> SEQUENCE: 20
atgccaatca cagctgcaga tattcgtcgt gaagtcaagg aaaaaaatgt tacctttatt    60
cgtcttatgt tctcagatat tttgggaacc atgaaaaacg tcgaaattcc tgctacagat   120
gaacagttag ataaggtctt gtcgaacaag gttatgtttg atggatcttc tattgaaggt   180
tttgtacgta tcaatgagtc ggatatgtac ttgtacccgg acttggatac atggacagtc   240
ttcccttggg gagatgaaaa tggaagtgtt gcaggtctga tctgtgatgt ytatacaaca   300
gaaggtgaac catttgcggg tgaccctcgt ggtaatttga acgagctct cgtcacatg    360
gaagaagttg gattcaaatc cttcaacctt ggtccagagc cagaattctt cctatttaag   420
ttggatgaaa tgggggaccc aacacttgaa gtgaatgaca agggtggcta ctttgacttg   480
gcacctactg accttgcgga caacacacgt cgtgagattg tgaatgtctt gaccaaaatg   540
ggatttgaag tagaagcgag tcaccacgag gttgcggttg acagcatga gattgacttt    600
aagtacgatg aagttctccg tgcttgtgat aagattcaaa tctttaagct tgttgttaaa   660
accattgctc gcaaacacgg actttacgca acatttatgg cgaagccaaa atttggtatt   720
gctggatcag gtatgcactg taatatgtcc ttgtttgatg cagaaggaaa taacgccttc   780
tttgatccaa atgatccaaa aggaatgcag ttgtcagaaa cagcttacca tttcctaggc   840
ggtttgatca gcatgctta caactatact gccatcatga cccaacagt taactcatac    900
aaacgtttgg ttccaggtta tgaagcgcct gtttacattg cttgggctgg tcgtaaccgt   960
tcgccacttg tgcgcgtacc tgcttcacgt ggtatgggaa ctcgtcttga gttgcgttca  1020
gtggatccaa tggcgaaccc ttacgttgct atggctgttc ttttggaagt tggtttgtat  1080
ggtattgaaa ataaaatcga agcaccagct cctatcgaag aaaatatcta catcatgaca  1140
gcagaagagc gcaaggaagc tggtattaca gaccttccat caactcttca aacgctttg  1200
aaagctttga cagaagatga agtggttaaa gctgctctcg gagatcacat ctatactagc  1260
ttccttgaag ccaaacgaat cgaatgggca agttatgcaa ccttcgtttc acaatgggaa  1320
attgataatt atttagacct ttactaa                                    1347

<210> SEQ ID NO 21
<211> LENGTH: 84
<212> TYPE: PRT
<213> ORGANISM: Streptococcus pneumoniae

<400> SEQUENCE: 21

Met Val Tyr Leu Val Leu Gly Ile Leu Leu Leu Leu Tyr Val Phe
1               5                   10                  15
Ala Thr Pro Glu Ser Ile Lys Gly Thr Val Asn Ile Val Ala Met Val
            20                  25                  30
Cys Ile Leu Val Ala Leu Leu Ile Leu Leu Val Leu Ser Phe Leu Lys
        35                  40                  45
Ile Phe Gln Leu Pro Thr Glu Ile Phe Leu Ala Ile Ala Met Leu Ile
    50                  55                  60
Leu Ala Tyr Phe Ser Val Arg Asp Ile Thr Leu Met Pro Val Lys Lys
65                  70                  75                  80
Ser Lys Arg Arg

<210> SEQ ID NO 22
<211> LENGTH: 255
<212> TYPE: DNA
<213> ORGANISM: Streptococcus pneumoniae
```

-continued

<400> SEQUENCE: 22

```
atggtctatt tagtcctagg aattttactg ctcctactct atgtatttgc gacaccagaa      60
agcattaaag ggactgtcaa tatcgtcgct atggtatgta ttttagtggc actcttgatt    120
ttattggttc tatctttct gaaaattttt caattaccaa cagaaatatt cctagcaata     180
gccatgttga tcctagctta ctttagtgtt agagacatca cactcatgcc agtcaaaaaa    240
agtaaaagaa gataa                                                      255
```

<210> SEQ ID NO 23
<211> LENGTH: 779
<212> TYPE: PRT
<213> ORGANISM: Streptococcus pneumoniae

<400> SEQUENCE: 23

```
Ser Gly Leu Gly Leu Asn Phe Tyr Ala Leu Ser Ser Tyr Tyr Leu Gly
  1               5                  10                  15

Ser Phe Leu Ala Pro Leu Val Tyr Phe Phe Asp Leu Thr Asn Met Pro
                 20                  25                  30

Asp Ala Ile Tyr Leu Thr Thr Leu Leu Lys Phe Gly Leu Ile Gly Leu
             35                  40                  45

Ser Thr Phe Phe Ser Leu Asn Lys Leu Phe Gln Ser Ile Pro Gln Ile
         50                  55                  60

Leu Lys Leu Ala Leu Ser Thr Ser Tyr Ala Leu Met Ser Phe Thr Val
 65                  70                  75                  80

Ser Gln Leu Glu Ile Lys Thr Trp Leu Asp Val Phe Ile Leu Ile Pro
                 85                  90                  95

Leu Ile Ile Thr Gly Leu His Leu Leu Ile Thr Glu Lys Lys Leu Leu
            100                 105                 110

Leu Tyr Phe Thr Ser Leu Ser Ile Leu Phe Ile Gln Asn Tyr Tyr Phe
        115                 120                 125

Gly Tyr Met Thr Val Leu Phe Leu Ile Phe Trp Tyr Leu Cys Gln Ile
    130                 135                 140

Ser Trp Asp Phe Lys Thr Arg Lys Ser Ser Val Leu Asp Phe Ile Val
145                 150                 155                 160

Ile Ser Phe Leu Ala Gly Met Ala Ser Leu Ile Met Thr Leu Pro Thr
                165                 170                 175

Leu Phe Asp Leu Gln Thr His Gly Glu Lys Leu Thr Glu Val Thr Lys
            180                 185                 190

Phe Gln Thr Glu Ser Ser Trp Tyr Leu Asp Leu Phe Ala Lys Gln Phe
        195                 200                 205

Ile Gly Ser Phe Asp Thr Thr Lys Tyr Gly Ala Ile Pro Met Ile Phe
    210                 215                 220

Val Gly Leu Phe Pro Phe Ile Leu Thr Ile Leu Phe Phe Thr Leu Lys
225                 230                 235                 240

Ser Ile Lys Phe His Val Lys Leu Ile Tyr Val Ile Phe Phe Ala Phe
                245                 250                 255

Leu Ile Ala Ser Phe Tyr Ile Glu Ala Leu Asp Leu Phe Trp Gln Gly
            260                 265                 270

Met His Thr Pro Asn Met Phe Leu His Arg Tyr Ala Trp Ile Phe Ser
        275                 280                 285

Thr Leu Leu Ile Tyr Thr Ala Ala Glu Val Leu Lys Arg Leu Lys Glu
    290                 295                 300

Leu Lys Val Trp Asn Phe Leu Val Ser Leu Phe Leu Val Val Ala Gly
305                 310                 315                 320
```

-continued

Phe Leu Ala Thr Ile Tyr Leu Lys Ser His Tyr Ser Leu Thr Asp Leu
            325                 330                 335

Asn Ile Leu Leu Thr Leu Glu Phe Leu Val Val Tyr Ser Leu Leu Leu
        340                 345                 350

Leu Ala Val Ile Lys Lys Phe Ile Ser Val Asn Leu Phe Ala Ile Leu
    355                 360                 365

Ile Ser Leu Phe Ile Leu Val Glu Met Ser Leu Asn Ala Ser Ser Gln
370                 375                 380

Met Asp Gly Ile Ala Lys Glu Trp Gly Phe Ala Ser Arg Ser Ala Tyr
385                 390                 395                 400

Ser Arg Asp Ile Pro Ala Met Glu Ser Phe Ser Thr Tyr Ile Gly Asn
                405                 410                 415

Gln Phe Thr Arg Thr Glu Lys Leu Gln Thr Gln Thr Gly Asn Asp Ser
            420                 425                 430

Met Lys Phe Asn Tyr Asn Gly Ile Ser Gln Phe Ser Ser Val Arg Asn
        435                 440                 445

Arg Ser Ser Ser Thr Leu Asp Lys Leu Gly Phe Lys Ser Ser Gly
    450                 455                 460

Thr Asn Leu Asn Leu Arg Tyr Ala Asn Asn Ser Ile Leu Ala Asp Ser
465                 470                 475                 480

Leu Phe Gly Ile Gln Tyr Asn Ile Ser Asp Ser Pro Ile Asp Lys Tyr
                485                 490                 495

Gly Phe Lys Asp Ile Tyr Gln Lys Asp Asn Leu Thr Leu Tyr Glu Asn
            500                 505                 510

Gln Tyr Ser Leu Pro Ile Ala Val Ala Ser Gln Ser Val Tyr Asn Asp
        515                 520                 525

Val Lys Phe Asn Glu His Thr Leu Asp Asn Gln Ala Ser Phe Leu Asn
530                 535                 540

Gln Leu Ala Asn Val Asn Phe Asp Tyr Phe Ser Pro Ile Pro Tyr Glu
545                 550                 555                 560

Lys Thr Glu Lys Ile Glu Asn Thr Asn Asp Leu Ile Ser Val Thr Ser
                565                 570                 575

Ser Ser Asn Glu Asp Ala Ala Ile Gln Tyr Gln Ile Glu Val Pro Glu
            580                 585                 590

Asn Ser Gln Val Tyr Leu Ser Phe Ile Asn Leu His Phe Ser Asn Asp
        595                 600                 605

Lys Gln Lys Lys Val Asp Ile Leu Val Asn Gly Glu Lys Lys Thr Phe
    610                 615                 620

Thr Thr Asp Asn Val Phe Ser Phe Phe Asn Leu Gly Tyr Thr Lys Glu
625                 630                 635                 640

Lys Lys Thr Phe Asn Ile Asn Val Ser Phe Pro Gly Asn Ser Gln Val
                645                 650                 655

Ser Phe Glu Ser Pro Thr Phe Tyr Arg Leu Asp Thr Lys Thr Phe Thr
            660                 665                 670

Glu Ala Ile Gln Lys Ile Lys Glu Gln Pro Val Thr Val Ser Thr Ser
        675                 680                 685

Lys Asn Lys Val Phe Ala Thr Tyr Asp Val Gln Asp Thr Ser Ile
    690                 695                 700

Phe Phe Thr Ile Pro Tyr Asp Lys Gly Trp Ser Ala Tyr Gln Asp Gly
705                 710                 715                 720

Lys Lys Ile Glu Ile Lys Gln Ala Gln Thr Gly Phe Met Lys Val Asp
                725                 730                 735

Ile Pro Lys Gly Lys Gly Thr Ile Thr Leu Ser Phe Ile Pro Asn Gly
            740                 745                 750

```
                Phe Ile Thr Gly Ala Ile Cys Ser Phe Thr Ser Leu Leu Leu Phe Gly
                    755                 760                 765

Ile Tyr Asn His Arg Arg Lys Ser Ser Lys Ala
                    770                 775

<210> SEQ ID NO 24
<211> LENGTH: 2343
<212> TYPE: DNA
<213> ORGANISM: Streptococcus pneumoniae

<400> SEQUENCE: 24
agtggtctag ggctaaactt ctatgccta tctagttatt acttgggtag ttttctcgcg       60
cctctggttt acttttttga tctaacgaat atgccagatg ctatctatct gacaactctc     120
ttaaaatttg gattgattgg tctgtcaacc ttttttagtt tgaataaatt gtttcaatct     180
atccctcaga ttttaaaact agccttatct acttcctatg ctctgatgag tttcactgtc     240
agtcaattag ataaaaaac ctggctagat gttttatct tgattccttt aattataact       300
ggtttacatc tactgataac tgaaaagaaa ctcctattgt actttacaag tctgtcaatc     360
ttatttattc aaaattatta ttttggatat atgacagtat tgtttcttat tttctggtat     420
ctctgtcaaa tttcgtggga ctttaagact cgaaaatcat ctgttcttga tttcatagtt     480 atctccttt tagctggtat ggctagtttg attatgactc ttcccactct atttgattta      540
cagacacatg gggaaaaatt gactgaagtt acaaagtttc aaactgaaag tagctggtat     600
cttgatctct tgctaagca attcattggt tcctttgaca caacaaagta tggggccatc     660
ccaatgattt tgttggact atttcccttt attttgacca tttatttt tacgctgaaa       720 tctattaagt ttcacgtgaa actcatatat gtaatattct ttgcatttct aattgcaagc    780
ttttacatag aagctcttga cttattttgg caaggcatgc atactccaaa catgttttta    840
catcgctatg cttggatttt ctctaccttg ttaatttaca cagcagcaga agtcttaaag    900
cgtctgaaag aacttaaagt ctggaatttt ttagtttcgc ttttttctgt agtagcagga    960
tttttagcta ccatctatct aaaatcgcat tattcttttt taacagattt gaatattctg   1020
cttactcttg aatttttggt tgtctattct cttttactcc ttgcagttat caaaaagttt   1080
atatctgtga atctatttgc cattctaatc tctttattta tactggttga atgagtttta   1140
aatgcttcat ctcaaatgga cggaattgct aaggaatggg gatttgcttc tcgaagtgct   1200
tatagtcgag atatcccagc tatggaatct ttctcaacat atattggaaa tcaatttact   1260
cgtactgaaa aactacaaac tcagacagga aatgacagta tgaaattcaa ctacaatgga   1320
atctctcaat tttcatctgt tcgaaatcgt tcatcaagct ctactttaga taaacttggt   1380
tttaaatcct ctgggactaa tctcaatctc cgatatgcaa ataatagtat tttggctgat   1440
agtttatttg gtatccagta caatatctca gacagtccta ttgataagta tggctttaaa   1500
gatatctatc aaaagataa tcttacccta tatgaaaatc aatactctct tccgattgca   1560
gttgcgagtc aatctgttta caatgatgtc aagttcaatg aacataccttt ggataatcag   1620 gcctcatttt taaatcaact tgctaacgtc aattttgatt attttctcc aataccttat    1680 gaaaaaacag aaaaaataga aaatactaat gatttgatta gtgtcacaag ttcttcaaat   1740
gaagatgcag caatccagta tcaaattgaa gttccagaaa acagccaagt ttatctctct   1800
ttcataaacc ttcactttc taacgataaa caaaagaagg ttgacatcct tgtaaatggt   1860
gaaaaaaaga cttttacaac tgataatgtc ttctccttct ttaatctagg atatactaaa   1920
gagaaaaaaa ctttcaatat caatgttagt ttccctggaa attcacaagt atcatttgaa   1980
```

-continued

```
tctcctacct tctatcgttt agataccaaa actttcaccg aggcaattca aaaaattaaa    2040
gaacaacctg tcacagtatc aacttctaaa aacaaggttt ttgctacata tgatgtccaa    2100
caagatacat ctattttctt caccattcct tatgacaaag gttggtctgc ctaccaagat    2160
ggtaagaaaa tagaaattaa acaagctcaa actggattta tgaaagttga cattcccaag    2220
gggaaaggaa ctattacact ttccttcatt cccaatggtt ttattactgg agcaatctgt    2280
tcctttactt ctctcttact atttggaatc tataatcaca gacgaaagtc atctaaggca    2340
taa                                                                  2343
```

<210> SEQ ID NO 25
<211> LENGTH: 423
<212> TYPE: PRT
<213> ORGANISM: Streptococcus pneumoniae
<220> FEATURE:
<221> NAME/KEY: misc_feature
<222> LOCATION: (27)..(27)
<223> OTHER INFORMATION: X is Pro or Thr
<220> FEATURE:
<221> NAME/KEY: misc_feature
<222> LOCATION: (28)..(28)
<223> OTHER INFORMATION: X is Gln or Lys

<400> SEQUENCE: 25

```
Met Asn Glu Lys Val Phe Arg Asp Pro Val His Asn Tyr Ile His Val
1               5                   10                  15

Asn Asn Gln Ile Ile Tyr Asp Leu Ile Asn Xaa Xaa Glu Phe Gln Arg
                20                  25                  30

Leu Arg Arg Ile Lys Gln Leu Gly Thr Ser Ser Tyr Thr Phe His Gly
            35                  40                  45

Gly Glu His Ser Arg Phe Ser His Cys Leu Gly Val Tyr Glu Ile Ala
    50                  55                  60

Arg Arg Ile Thr Glu Ile Phe Glu Glu Lys Tyr Pro Glu Glu Trp Asn
65                  70                  75                  80

Pro Ala Glu Ser Leu Leu Thr Met Thr Ala Ala Leu Leu His Asp Leu
                85                  90                  95

Gly His Gly Ala Tyr Ser His Thr Phe Glu His Leu Phe Asp Thr Asp
            100                 105                 110

His Glu Ala Ile Thr Gln Glu Ile Ile Gln Asn Pro Glu Thr Glu Ile
        115                 120                 125

His Gln Val Leu Leu Gln Val Ala Pro Asp Phe Pro Glu Lys Val Ala
    130                 135                 140

Ser Val Ile Asp His Thr Tyr Pro Asn Lys Gln Val Val Gln Leu Ile
145                 150                 155                 160

Ser Ser Gln Ile Asp Ala Asp Arg Met Asp Tyr Leu Leu Arg Asp Ser
                165                 170                 175

Tyr Phe Thr Gly Ala Ser Tyr Gly Glu Phe Asp Leu Thr Arg Ile Leu
            180                 185                 190

Arg Val Ile Arg Pro Ile Glu Asn Gly Ile Ala Phe Gln Arg Asn Gly
        195                 200                 205

Met His Ala Ile Glu Asp Tyr Val Leu Ser Arg Tyr Gln Met Tyr Met
    210                 215                 220

Gln Val Tyr Phe His Pro Ala Thr Arg Ala Met Glu Val Leu Leu Gln
225                 230                 235                 240

Asn Leu Leu Lys Arg Ala Lys Glu Leu Tyr Pro Glu Asp Lys Asp Phe
                245                 250                 255

Phe Ala Arg Thr Ser Pro His Leu Leu Pro Phe Glu Lys Asn Val
            260                 265                 270
```

```
Thr Leu Thr Asp Tyr Leu Ala Leu Asp Asp Gly Val Met Asn Thr Tyr
        275                 280                 285
Phe Gln Leu Trp Met Thr Ser Pro Asp Lys Ile Leu Ala Asp Leu Ser
    290                 295                 300
His Arg Phe Val Asn Arg Lys Val Phe Lys Ser Ile Thr Phe Ser Gln
305                 310                 315                 320
Glu Asp Gln Asp Gln Leu Thr Ser Met Arg Lys Leu Val Glu Asp Ile
                325                 330                 335
Gly Phe Asp Pro Asp Tyr Tyr Thr Ala Ile His Lys Asn Phe Asp Leu
            340                 345                 350
Pro Tyr Asp Ile Tyr Arg Pro Glu Ser Glu Asn Pro Arg Thr Gln Ile
        355                 360                 365
Glu Ile Leu Gln Lys Asn Gly Glu Leu Ala Glu Leu Ser Ser Leu Ser
    370                 375                 380
Pro Ile Val Gln Ser Leu Ala Gly Ser Arg His Gly Asp Asn Arg Phe
385                 390                 395                 400
Tyr Phe Pro Lys Glu Met Leu Asp Gln Asn Ser Ile Phe Ala Ser Ile
                405                 410                 415
Thr Gln Gln Phe Leu His Leu
            420

<210> SEQ ID NO 26
<211> LENGTH: 1270
<212> TYPE: DNA
<213> ORGANISM: Streptococcus pneumoniae

<400> SEQUENCE: 26
atgaacgaaa aagtattccg tgaccctgtt cacaactaca tccatgtcaa taatcaaatc      60
atctatgact tgattaatmc amaagaattt cagcgtttgc gccggatcaa caactgggga     120
acttccagtt ataccttcca cggtggagaa cacagtcgct tctctcactg tctaggagtc     180
tatgaaattg cacgacgcat cacagagatt ttcgaagaaa atatcctga ggaatggaat      240 cctgccgagt ctctcttgac catgaccgct gctctcctac acgaccttgg catggtgcc     300 tactcccata ctttgaaca tctctttgat acagaccatg aagccattac tcaggagatt      360
attcaaaatc ctgagacaga gattcaccaa gtcctgctac aagtggcacc tgatttccca     420
gaaaaggtgg ccagtgtcat tgaccatacc tatcctaata gcaggtcgt gcagctcatt     480 tctagtcaga ttgacgcaga tcgcatggac tatctcttgc gcgactccta ttttacagga     540
gcatcctatg ggaatttga cctgactcga atcctccgag tcattcgtcc tatcgaaaat     600
ggtatcgcct ttcagcgcaa tggcatgcac gccatcgaag actacgtcct cagtcgctac     660
cagatgtaca tgcaggttta tttccacccc gcaacacgcg ccatggaagt tctcctacag     720
aatcttctca acgcgccaa ggaactctat cctgaggaca aggatttctt tgcccgaact      780
tctccacacc tcctgccttt cttcgaaaaa aatgtgacct tgactgacta tctggctctg     840
gatgatggcg tgatgaatac ctacttccag ctttggatga ccagtcctga caagattctt     900
gcagatttat cgcatcgctt tgtcaaccgc aaggtcttta atccattac cttttcacaa     960 gaggaccaag atcaacttac tagcatgaga aaattggttg aggatatcgg ctttgatccc    1020
gactactaca ctgccattca taagaacttt gacctccctt atgatatcta tcgtcccgaa   1080
tctgaaaacc cacggacaca gattgagatt ttacaaaaaa atggagaact ggccgaactc   1140
tctagcctgt ctcctatcgt ccaatccctt gctggcagtc gccacggaga taatcgcttt   1200
```

-continued

```
tattttccaa agaaatgtt ggaccaaaac agcatctttg caagcattac ccagcaattt    1260
ttacacttga                                                          1270
```

<210> SEQ ID NO 27
<211> LENGTH: 53
<212> TYPE: PRT
<213> ORGANISM: Streptococcus pneumoniae

<400> SEQUENCE: 27

```
Met Asn Pro Ser Leu Glu Asp Ile Asn Ala Thr Ile Ala Thr Gly Tyr
1               5                   10                  15

Ser Ser Asp Thr Ala Ile Lys Glu Ser Ile Asp Phe Phe Gln Asn Arg
            20                  25                  30

Thr Gln Thr Phe Leu Thr Asn Asn His Ala His Leu Glu His Thr Thr
        35                  40                  45

Lys Glu Val Arg Cys
    50
```

<210> SEQ ID NO 28
<211> LENGTH: 162
<212> TYPE: DNA
<213> ORGANISM: Streptococcus pneumoniae

<400> SEQUENCE: 28

```
atgaatccca gcttggagga tatcaatgca accatagcca ctggatacag ctcggacacg     60
gccatcaaag agagcattga tttcttccaa aaccgaactc aaacgttcct caccaacaac    120
catgctcatc ttgagcacac caccaaagag gtcagatgtt aa                       162
```

<210> SEQ ID NO 29
<211> LENGTH: 36
<212> TYPE: PRT
<213> ORGANISM: Streptococcus pneumoniae

<400> SEQUENCE: 29

```
Met Leu His Leu Lys Leu Val Lys Gln Glu Ile Glu Ala Glu Lys Pro
1               5                   10                  15

Ala Ser Val Glu Ala Trp Ile Ile Ser Val Lys Phe Lys Lys Gly Cys
            20                  25                  30

Tyr Arg His Ile
        35
```

<210> SEQ ID NO 30
<211> LENGTH: 111
<212> TYPE: DNA
<213> ORGANISM: Streptococcus pneumoniae

<400> SEQUENCE: 30

```
atgctacact taaaattagt aaaacaagaa atagaagctg aaaagccagc atctgtagaa     60
gcttggatca tttccgtcaa atttaaaaaa ggttgctacc gacatatata g             111
```

<210> SEQ ID NO 31
<211> LENGTH: 126
<212> TYPE: PRT
<213> ORGANISM: Streptococcus pneumoniae

<400> SEQUENCE: 31

```
Met Glu Leu Val Leu Pro Asn Asn Tyr Val Ala Leu Glu Gln Glu Glu
1               5                   10                  15

Met Met Tyr Leu Asp Gly Gly Gly Val Gly Arg Asn Trp Trp Asn Ser
            20                  25                  30
```

```
Arg Gly Ser Phe Ala Thr Val Leu Asp Val Asp Leu Ala Ile Tyr Ser
         35                  40                  45

Gly Gly Ala Thr Ile Tyr Ser Ala Tyr Ala Ile Lys Lys Ala Ile Ser
 50                  55                  60

Ala Asn Arg Gly Ala Ile Thr Arg Thr Leu Arg Ser Leu Ile Ile Lys
 65                  70                  75                  80

His Val Gly Ser Ala Ala Gly His Leu Val Asn Thr Ala Leu Asn Val
             85                  90                  95

Ala Leu Thr Val Thr Gly Phe Ser Leu Gly Gly Ala Ile Ala Tyr Gly
            100                 105                 110

Ala Asp Trp Ala Asp Gly Ser Leu Asp Gly Tyr Ile Phe Ala
            115                 120                 125

<210> SEQ ID NO 32
<211> LENGTH: 381
<212> TYPE: DNA
<213> ORGANISM: Streptococcus pneumoniae

<400> SEQUENCE: 32
atggaactcg tattaccaaa taattatgtt gctcttgagc aagaagagat gatgtatctt      60 gatggggtg gtggtggtcg taactggtgg aatagtagag gtagttttgc aacagttctg     120
gatgtagatt tggccatcta tagtggtggt gcaacaattt attctgctta tgcgataaaa     180
aaagctatct cagctaatag aggggctatt acgagaacat tacgtagttt aataattaaa     240
catgtaggta gtgcagctgg ccatttagtc aatactgcac taaacgttgc actaactgtt     300
actggatttt cactaggtgg agcaatcgca tatggggctg agtgggctga cggtagctta     360
gatggttata tttttgctta a                                                381

<210> SEQ ID NO 33
<211> LENGTH: 124
<212> TYPE: PRT
<213> ORGANISM: Streptococcus pneumoniae

<400> SEQUENCE: 33

Met Glu Leu Val Leu Pro Asn Asn Tyr Val Ala Leu Glu Gln Glu Glu
 1               5                  10                  15

Met Met Tyr Leu Asp Gly Gly Phe Ser Ile Leu Arg Trp Pro Val Ala
             20                  25                  30

Thr Ala Ile Asn Ile Ala Phe Asn Gly Val Leu Gly Gly Ala Ile
         35                  40                  45

Ser Leu Val Arg Asn Tyr Ile Arg Asn Tyr Gly Leu Gly Arg Val Thr
 50                  55                  60

Ser Ala Ile Ala Gly Ala Ala Arg Tyr Val Gly Val Arg Val Ala
 65                  70                  75                  80

Asn Arg Val Ala Gly Phe Ala Leu Ser Ala Ile Asn Gly Phe Ala Ala
             85                  90                  95

Trp Met Ser Ile Gly Asp Ala Ile Thr Thr Ile Trp Ala Asn Asn Asp
            100                 105                 110

Val Asn Arg Arg Asp Pro Asn Leu Asn Ala Leu Trp
            115                 120

<210> SEQ ID NO 34
<211> LENGTH: 375
<212> TYPE: DNA
<213> ORGANISM: Streptococcus pneumoniae
```

<400> SEQUENCE: 34

```
atggaactcg tattaccaaa taattatgtt gctcttgagc aagaagagat gatgtatctt      60
gatgggggat ttctattct gagatggcct gttgcaacag ccattaatat agcttttaat     120
ggtgttttag gtggaggagc aatcagtcta gttagaaatt atattcgtaa ttatggtttg    180
gggcgagtta caagcgcaat tgctggagca gctgcaagat atgttggggt acagttgca    240
aatagagtgg caggatttgc actgtctgct attaatggat ttgcagcttg gatgtcaatt    300
ggcgatgcta ttacaacaat ctgggccaac aatgatgtaa ataggagaga cccaaattta    360
aacgccttgt ggtaa                                                     375
```

<210> SEQ ID NO 35
<211> LENGTH: 117
<212> TYPE: PRT
<213> ORGANISM: Streptococcus pneumoniae

<400> SEQUENCE: 35

```
Met Glu Leu Val Leu Pro Asn Asn Tyr Val Val Ile Asp Glu Glu Glu
  1               5                  10                  15
Met Met Tyr Leu Asp Gly Gly Ala Tyr Leu Ser Lys Arg Ala Cys Gln
             20                  25                  30
Gly Ile Cys Ala Ala Leu Ala Met Ser Pro Gly Thr Phe Ile Ala Leu
         35                  40                  45
Ala Gly Ala Ala Val Leu Thr Lys Lys Leu Ile Asn Tyr Ile Lys Val
     50                  55                  60
Gly Gly Leu Gly Gly Trp Leu Ile Gly Ala Ala Ala Gly Val Leu Ala
 65                  70                  75                  80
Gly Ala Ala Gly Arg Ile Ala Tyr Cys Ile Gly Tyr Gly Ala Leu Asn
                 85                  90                  95
Arg Gly Cys Asp Ile Ser Gly Asn Pro Tyr Pro Trp Asp Gly Phe Ile
            100                 105                 110
Ser Ala Thr Val Arg
        115
```

<210> SEQ ID NO 36
<211> LENGTH: 354
<212> TYPE: DNA
<213> ORGANISM: Streptococcus pneumoniae

<400> SEQUENCE: 36

```
atggaacttg tattaccaaa taattatgtt gtgattgatg aagaagagat gatgtacctt      60
gatgggggag cttatttaag caagcgtgct tgtcaaggaa tttgcgcagc tttagctatg    120
agtccaggaa cttttatagc attagctgga gctgcagttt taaccaaaaa actaataaac    180
tatattaaag ttggaggcct tggaggttgg cttattggtg cagcagcagg tgtattggct    240
ggggcggcag gaagaatagc ttactgtatt ggatatggtg ctcttaatag aggttgtgat    300
attagcggga acccttatcc ttgggatgga ttcatatctg cgacagtaag atga          354
```

<210> SEQ ID NO 37
<211> LENGTH: 117
<212> TYPE: PRT
<213> ORGANISM: Streptococcus pneumoniae

```
<400> SEQUENCE: 37

Met Glu Leu Val Leu Pro Asn Asn Tyr Val Ile Asp Glu Glu
1               5                   10                  15

Met Met Tyr Leu Asp Gly Glu Ala Tyr Leu Ser Lys Arg Ala Cys Gln
            20                  25                  30

Gly Ile Cys Ala Ala Leu Ala Met Ser Ser Gly Thr Phe Ile Ala Leu
        35                  40                  45

Ala Gly Ala Ala Val Leu Thr Lys Lys Leu Ile Asn Tyr Ile Lys Val
50                  55                  60

Gly Gly Leu Gly Gly Trp Leu Ile Gly Ala Ala Gly Val Leu Ala
65                  70                  75                  80

Thr Ala Ala Gly Lys Ile Ala Tyr Tyr Ile Gly Tyr Gly Val Leu Asn
                85                  90                  95

Arg Gly Cys Asp Ile Asn Gly Asn Pro Tyr Pro Trp Asp Gly Phe Ile
            100                 105                 110

Ser Ala Thr Val Arg
        115

<210> SEQ ID NO 38
<211> LENGTH: 363
<212> TYPE: DNA
<213> ORGANISM: Streptococcus pneumoniae

<400> SEQUENCE: 38
atggaacttg tattaccaaa taattatgtt gtgattgatg aagaagaaat gatgtatctt      60
gatggggaag cttatttaag caagcgtgct tgtcaaggaa tttgcgcagc tttagctatg     120
agttcaggca ctttttatagc attagctgga gctgcagttt taaccaaaaa actaataaac    180
tatattaagg ttggaggtct tggaggctgg cttattggtg cagcagcagg tgtattggct     240
acagcagcag ggaaaatagc ttactatatt ggatatggtg ttcttaatag aggttgtgat     300
attaacggga accettatcc ttgggatgga ttcatatctg cgacagtaag atgagtaatg     360
tag                                                                  363

<210> SEQ ID NO 39
<211> LENGTH: 128
<212> TYPE: PRT
<213> ORGANISM: Streptococcus pneumoniae

<400> SEQUENCE: 39

Met Lys Gln Phe Gln Leu Arg Arg Lys Gln Met Glu Leu Val Leu
1               5                   10                  15

Pro Asn Asn Tyr Val Val Ile Asp Glu Glu Met Met Tyr Leu Asp
            20                  25                  30

Gly Gly Ala Tyr Leu Ser Lys Arg Ala Cys Gln Gly Ile Cys Val Ala
        35                  40                  45

Leu Ala Met Ser Pro Gly Ile Phe Ile Ala Leu Ala Gly Ala Ala Val
50                  55                  60

Leu Thr Lys Lys Leu Ile Asn Tyr Ile Lys Val Gly Gly Leu Gly Gly
65                  70                  75                  80

Trp Leu Ile Gly Ala Ala Gly Val Leu Ala Thr Ala Ala Gly Lys
                85                  90                  95

Ile Ala Tyr Cys Ile Gly Tyr Gly Ala Leu Asn Arg Gly Cys Asp Ile
            100                 105                 110

Ser Gly Asn Pro Tyr Pro Trp Asp Gly Phe Ile Ser Ala Thr Val Arg
        115                 120                 125
```

<210> SEQ ID NO 40
<211> LENGTH: 354
<212> TYPE: DNA
<213> ORGANISM: Streptococcus pneumoniae

<400> SEQUENCE: 40

```
atggaacttg tattaccaaa taattatgtt gtgattgatg aagaagaaat gatgtatctt        60
gatgggggag cttatttaag caagcgtgct tgtcaaggaa tttgcgtagc tttagctatg       120
agtccaggaa ttttatagc attagctgga gctgcagttt taaccaaaaa actaataaac        180
tatattaagg ttggaggtct tggaggctgg cttattggtg cagcagcagg tgtattggct       240
acagcagcag gaaaaatagc ttactgtatt ggatatggtg ctcttaatag aggttgtgat       300
attagcggga acccttatcc ttgggatgga ttcatatctg cgacagtaag atga            354
```

<210> SEQ ID NO 41
<211> LENGTH: 123
<212> TYPE: PRT
<213> ORGANISM: Streptococcus pneumoniae

<400> SEQUENCE: 41

```
Met Glu Leu Val Leu Pro Asn Asn Tyr Val Val Ile Asp Glu Glu
1               5                  10                  15

Met Met Tyr Leu Asp Gly Gly Ala Ile Tyr Ile Pro Arg Trp Ala Ile
            20                  25                  30

Thr Gly Ala Ile Thr Gly Ala Ala Tyr Ala Ala Leu Ala Ala Ala Gly
        35                  40                  45

Gly Gly Gly Leu Gln Leu Val Leu Ala Ser Tyr Gly Leu Arg Ser Ala
    50                  55                  60

Leu Val Ala Gly Ile Val Lys Gly Leu Gly Val Leu Gly Ile His Ile
65                  70                  75                  80

Gly Asn Ala Phe Ala Asn Thr Val Ile Arg Ser Ile Ala Ser Ala Gly
                85                  90                  95

Ile Gly Ala Gly Ala Asp Trp Ile Phe Thr Asn Ile Ile Asp Gly Trp
            100                 105                 110

Asp Gly Arg Arg Asp Asn Gln Leu Arg Ile Gly
        115                 120
```

<210> SEQ ID NO 42
<211> LENGTH: 372
<212> TYPE: DNA
<213> ORGANISM: Streptococcus pneumoniae

<400> SEQUENCE: 42

```
atggaacttg tattaccaaa taattatgtt gtgattgatg aagaagagat gatgtaccctt       60
gatggggggg ctatatatat acccaggtgg gcaattacag gagccattac tggtgcagca       120
tatgcagcat agcagcagc aggaggtgga ggccttcaac tagttcttgc atcttatgga        180
ttacgctccg cactggtagc tgggattgtt aaaggtttag gagtattagg aattcatatt       240
ggaaatgctt ttgcaaatac tgttattaga agtattgcat ctgctggaat tggtgctgga       300
gctgattgga ttttaccaa tattattgat ggctgggatg gcgacgtgaa taatcaattg        360
agaataggtt aa                                                           372
```

<210> SEQ ID NO 43
<211> LENGTH: 126
<212> TYPE: PRT
<213> ORGANISM: Streptococcus pneumoniae

<400> SEQUENCE: 43

```
Met Glu Leu Val Leu Pro Asn Asn Tyr Val Asp Leu Glu Gln Glu Glu
1               5                   10                  15
Met Met Tyr Leu Asp Gly Gly Val Gly Arg Asn Trp Trp Asn Ser
            20                  25                  30
Arg Gly Ser Phe Ala Thr Val Leu Asp Val Gly Leu Ala Ile Tyr Ser
        35                  40                  45
Gly Gly Ala Thr Ile Tyr Ser Ala Tyr Ala Ile Lys Lys Ala Ile Ser
    50                  55                  60
Ala Asn Arg Gly Ala Ile Thr Arg Thr Leu Arg Ser Leu Ile Ile Lys
65                  70                  75                  80
His Val Gly Ser Ala Ala Gly His Leu Val Asn Thr Ala Leu Asn Val
                85                  90                  95
Ala Leu Thr Val Thr Gly Phe Ser Leu Gly Gly Ala Ile Ala Tyr Gly
            100                 105                 110
Ala Asp Trp Ala Asp Gly Ser Leu Asp Gly Tyr Ile Phe Ala
        115                 120                 125
```

<210> SEQ ID NO 44
<211> LENGTH: 381
<212> TYPE: DNA
<213> ORGANISM: Streptococcus pneumoniae

<400> SEQUENCE: 44

```
atggaactcg tattaccaaa taattatgtt gatcttgagc aagaagagat gatgtatctt      60
gatggggtg  tgttggtcg  taactggtgg aatagtagag gtagttttgc aacagttctg     120
gatgtaggtt tggccatcta tagtggtggt gcaacaattt attctgctta tgcgataaaa     180
aaagctatct cagctaatag aggggctatt acgagaacat acgtagtttt aataattaaa    240
catgtaggta gtgcagctgg ccatttagtc aatactgcac taaacgttgc actaactgtt    300
actggatttt cactaggtgg agcaatcgca tatgggctga ttgggctga cggtagctta    360
gatggttata ttttgctta  a                                              381
```

<210> SEQ ID NO 45
<211> LENGTH: 23
<212> TYPE: PRT
<213> ORGANISM: Streptococcus pneumoniae
<220> FEATURE:
<221> NAME/KEY: misc_feature
<222> LOCATION: (11)..(11)
<223> OTHER INFORMATION: X is Val, Ala or Asp
<220> FEATURE:
<221> NAME/KEY: misc_feature
<222> LOCATION: (12)..(12)
<223> OTHER INFORMATION: X is Ile or Leu
<220> FEATURE:
<221> NAME/KEY: misc_feature
<222> LOCATION: (13)..(13)
<223> OTHER INFORMATION: X is Asp or Glu
<220> FEATURE:
<221> NAME/KEY: misc_feature
<222> LOCATION: (14)..(14)
<223> OTHER INFORMATION: X is Gln or Glu
<220> FEATURE:
<221> NAME/KEY: misc_feature
<222> LOCATION: (23)..(23)
<223> OTHER INFORMATION: X is Glu or Gly -continued

<400> SEQUENCE: 45

Met Glu Leu Val Leu Pro Asn Asn Tyr Val Xaa Xaa Xaa Xaa Glu Glu
1               5                   10                  15

Met Met Tyr Leu Asp Gly Xaa
            20

<210> SEQ ID NO 46
<211> LENGTH: 40
<212> TYPE: DNA
<213> ORGANISM: Artificial sequence
<220> FEATURE:
<223> OTHER INFORMATION: Primer

<400> SEQUENCE: 46
cgagatctga tatctcacaa acagataacg gcgtaaatag          40

<210> SEQ ID NO 47
<211> LENGTH: 43
<212> TYPE: DNA
<213> ORGANISM: Artificial sequence
<220> FEATURE:
<223> OTHER INFORMATION: Primer

<400> SEQUENCE: 47
gaagatcttc cccgggatca caaacagata acggcgtaaa tag          43

<210> SEQ ID NO 48
<211> LENGTH: 42
<212> TYPE: DNA
<213> ORGANISM: Artificial sequence
<220> FEATURE:
<223> OTHER INFORMATION: Primer

<400> SEQUENCE: 48
cgagatctga tatccatcac aaacagataa cggcgtaaat ag          42

<210> SEQ ID NO 49
<211> LENGTH: 32
<212> TYPE: DNA
<213> ORGANISM: Artificial sequence
<220> FEATURE:
<223> OTHER INFORMATION: Primer

<400> SEQUENCE: 49
cgggatcctt atggacctga atcagcgttg tc          32

<210> SEQ ID NO 50
<211> LENGTH: 23
<212> TYPE: DNA
<213> ORGANISM: Artificial sequence
<220> FEATURE:
<223> OTHER INFORMATION: Primer

<400> SEQUENCE: 50
ggatgctttg tttcaggtgt atc          23

<210> SEQ ID NO 51
<211> LENGTH: 82
<212> TYPE: DNA
<213> ORGANISM: Artificial sequence
<220> FEATURE:
<223> OTHER INFORMATION: Primer -continued

```
<400> SEQUENCE: 51
catgatatcg gtacctcaag ctcatatcat tgtccggcaa tggtgtgggc ttttttttgtt    60 ttagcggata acaatttcac ac                                              82

<210> SEQ ID NO 52
<211> LENGTH: 81
<212> TYPE: DNA
<213> ORGANISM: Artificial sequence
<220> FEATURE:
<223> OTHER INFORMATION: Primer

<400> SEQUENCE: 52
gcggatcccc cgggcttaat taatgtttaa acactagtcg aagatctcgc gaattctcct    60
gtgtgaaatt gttatccgct a                                              81

<210> SEQ ID NO 53
<211> LENGTH: 24
<212> TYPE: DNA
<213> ORGANISM: Artificial sequence
<220> FEATURE:
<223> OTHER INFORMATION: Primer

<400> SEQUENCE: 53
cgccagggtt ttcccagtca cgac                                           24

<210> SEQ ID NO 54
<211> LENGTH: 20
<212> TYPE: DNA
<213> ORGANISM: Artificial sequence
<220> FEATURE:
<223> OTHER INFORMATION: Primer

<400> SEQUENCE: 54 tcagggggggc ggagcctatg                                               20

<210> SEQ ID NO 55
<211> LENGTH: 22
<212> TYPE: DNA
<213> ORGANISM: Artificial sequence
<220> FEATURE:
<223> OTHER INFORMATION: Primer

<400> SEQUENCE: 55
tcgtatgttg tgtggaattg tg                                             22

<210> SEQ ID NO 56
<211> LENGTH: 26
<212> TYPE: DNA
<213> ORGANISM: Artificial sequence
<220> FEATURE:
<223> OTHER INFORMATION: Primer

<400> SEQUENCE: 56
tccggctcgt atgttgtgtg gaattg                                         26

<210> SEQ ID NO 57
<211> LENGTH: 35
<212> TYPE: DNA
<213> ORGANISM: Artificial sequence
<220> FEATURE:
<223> OTHER INFORMATION: Primer

<400> SEQUENCE: 57
ggcggatcca taaacgaaga aataagcaag gaagc                               35
```

```
<210> SEQ ID NO 58
<211> LENGTH: 30
<212> TYPE: DNA
<213> ORGANISM: Artificial sequence
<220> FEATURE:
<223> OTHER INFORMATION: Primer

<400> SEQUENCE: 58
ggcaagcttt tagatttctc tggtcatatc                                    30

<210> SEQ ID NO 59
<211> LENGTH: 30
<212> TYPE: DNA
<213> ORGANISM: Artificial sequence
<220> FEATURE:
<223> OTHER INFORMATION: Primer

<400> SEQUENCE: 59
ggcggatcca aacaatttca actaaggagg                                    30

<210> SEQ ID NO 60
<211> LENGTH: 31
<212> TYPE: DNA
<213> ORGANISM: Artificial sequence
<220> FEATURE:
<223> OTHER INFORMATION: Primer

<400> SEQUENCE: 60
ggcaagcttt catcttactg tcgcagatat g                                  31
```